US009149427B2

(12) United States Patent
Ling et al.

(10) Patent No.: US 9,149,427 B2
(45) Date of Patent: Oct. 6, 2015

(54) CELL LINES THAT SECRETE ANTI-ANGIOGENIC ANTIBODY-SCAFFOLDS AND SOLUBLE RECEPTORS AND USES THEREOF

(75) Inventors: Vincent Ling, Walpole, MA (US); Arne M. Nystuen, Brookline, MA (US); Weng Tao, Lincoln, RI (US); Paul Stabila, Coventry, RI (US); Konrad Kauper, Sutton, MA (US)

(73) Assignee: Neurotech USA, Inc., Cumberland, RI (US)

( * ) Notice: Subject to any disclaimer, the term of this patent is extended or adjusted under 35 U.S.C. 154(b) by 0 days.

(21) Appl. No.: 13/308,264

(22) Filed: Nov. 30, 2011

(65) Prior Publication Data

US 2012/0141573 A1    Jun. 7, 2012

Related U.S. Application Data

(60) Provisional application No. 61/419,138, filed on Dec. 2, 2010.

(51) Int. Cl.
*C12N 5/02*        (2006.01)
*C12N 5/10*        (2006.01)
*A61K 9/00*        (2006.01)
*A61L 27/38*       (2006.01)
*A61K 38/17*       (2006.01)
*A61K 35/12*       (2015.01)
*C07K 14/71*       (2006.01)
*A61K 48/00*       (2006.01)

(52) U.S. Cl.
CPC .............. *A61K 9/0051* (2013.01); *A61K 35/12* (2013.01); *A61K 38/179* (2013.01); *A61L 27/38* (2013.01); *C07K 14/71* (2013.01); *A61K 48/005* (2013.01); *A61L 2430/16* (2013.01); *C07K 2319/30* (2013.01); *C12N 2830/46* (2013.01)

(58) Field of Classification Search
CPC ... A61K 35/12; A61K 38/179; A61K 48/005; A61K 9/0051; A61L 2430/16; A61L 27/38
See application file for complete search history.

(56) References Cited

U.S. PATENT DOCUMENTS

| | | | |
|---|---|---|---|
| 3,615,024 A | 10/1971 | Michaels | |
| 4,409,331 A | 10/1983 | Lim | |
| 4,652,833 A | 3/1987 | Batts | |
| 4,744,933 A | 5/1988 | Rha et al. | |
| 4,892,538 A | 1/1990 | Aebischer et al. | |
| 4,968,733 A | 11/1990 | Muller et al. | |
| 4,976,859 A | 12/1990 | Wechs | |
| 4,997,929 A | 3/1991 | Collins et al. | |
| 5,002,661 A | 3/1991 | Chick et al. | |
| 5,141,856 A | 8/1992 | Collins et al. | |
| 5,156,844 A | 10/1992 | Aebischer et al. | |
| 5,158,881 A | 10/1992 | Aebischer et al. | |
| 5,283,138 A | 2/1994 | Ferrando | |
| 5,283,187 A | 2/1994 | Aebischer et al. | |
| 5,284,761 A | 2/1994 | Aebischer et al. | |
| 5,364,769 A | 11/1994 | Rosenthal | |
| 5,453,361 A | 9/1995 | Yancopoulos et al. | |
| 5,512,600 A | 4/1996 | Mikos et al. | |
| 5,550,050 A | 8/1996 | Holland et al. | |
| 5,639,275 A | 6/1997 | Baetge et al. | |
| 5,653,688 A | 8/1997 | Mills et al. | |
| 5,653,975 A | 8/1997 | Baetge et al. | |
| 5,713,887 A | 2/1998 | Mills et al. | |
| 5,738,673 A | 4/1998 | Mills et al. | |
| 5,762,798 A | 6/1998 | Wenthold et al. | |
| 5,932,460 A | 8/1999 | Mills et al. | |
| 6,123,700 A | 9/2000 | Mills et al. | |
| 6,306,136 B1 | 10/2001 | Baccelli | |
| 6,361,771 B1 | 3/2002 | Tao et al. | |
| 6,627,422 B1 | 9/2003 | Li et al. | |
| 6,653,687 B1 | 11/2003 | Yamazaki | |
| 2005/0175610 A1 | 8/2005 | Wiegand et al. | |

(Continued)

FOREIGN PATENT DOCUMENTS

| | | |
|---|---|---|
| WO | WO-9100119 A1 | 1/1991 |
| WO | WO-9219195 A1 | 11/1992 |

(Continued)

OTHER PUBLICATIONS

"Expression of Cloned Genes in Cultured Mammalian Cells." *Molecular Cloning: A Laboratory Manual.* Sambrook et al., eds. Cold Spring Harbor, New York: Cold Spring Harbor Laboratory Press. 2nd ed. Chapter 16 (1989):1-81.
"Expression of Cloned Genes in *Escherichia coli.*" *Molecular Cloning: A Laboratory Manual.* Sambrook et al., eds. Cold Spring Harbor, New York: Cold Spring Harbor Laboratory Press. 2nd ed. Chapter 17 (1989):1-44.
Aebischer et al. " Transplantation in Humans of Encapsulated Xenogeneic Cells Without Immunosuppression." *Transplantation.* 58.12(1994):1275-1276.
ATCC Accession No. CRL-2302, retrieved May 4, 2012.
Ausubel et al. "Using DNA Fragments as Probes." *Current Protocols in Molecular Biology.* New York: Wiley & Sons. 1(1989):6.3.1-6.3.6.

(Continued)

*Primary Examiner* — Deborah Crouch
*Assistant Examiner* — Magdalene Sgagias
(74) *Attorney, Agent, or Firm* — Cooley LLP; Ivor R. Elrifi; Christina K. Stock

(57) ABSTRACT

The invention provides nucleic acid and polypeptide sequences encoding antibody based scaffolds such as full antibodies, antibody Fab fragments, single chain antibodies, soluble VEGF receptor-Fc fusion proteins, and/or anti-angiogenic PDGF receptors. Also encompassed are cell lines encoding such anti-angiogenic antibody scaffolds, VEGF receptors, and/or PDGF receptors. The invention also provides encapsulated cell therapy devices that are capable of delivering such anti-angiogenic antibody scaffolds, VEGF receptors, and/or PDGF receptors as well as methods of using these devices to deliver the anti-angiogenic antibody scaffolds, VEGF receptors, and/or PDGF receptors to medically treat disorders in patients, including ophthalmic, vascular, inflammatory, and cell proliferation diseases.

39 Claims, 16 Drawing Sheets

(56) References Cited

U.S. PATENT DOCUMENTS

| | | | | |
|---|---|---|---|---|
| 2006/0239966 | A1* | 10/2006 | Tornoe et al. | 424/93.2 |
| 2009/0136465 | A1 | 5/2009 | Merenick et al. | |
| 2009/0269319 | A1* | 10/2009 | Tao et al. | 424/93.7 |
| 2010/0272780 | A1* | 10/2010 | Ling et al. | 424/427 |

FOREIGN PATENT DOCUMENTS

| | | |
|---|---|---|
| WO | WO-9300128 A1 | 1/1993 |
| WO | WO-9303901 A1 | 3/1993 |
| WO | WO-9306116 A1 | 4/1993 |
| WO | WO-9505452 A2 | 2/1995 |
| WO | WO-9530686 A1 | 11/1995 |
| WO | WO-9602646 A2 | 2/1996 |
| WO | WO-9805304 A1 | 2/1998 |
| WO | WO-9952573 A1 | 10/1999 |
| WO | WO-2007078922 A2 | 7/2007 |
| WO | WO-2009149205 A2 | 12/2009 |

OTHER PUBLICATIONS

Baetge et al. "Complete Nucleotide and Deduced Amino Acid Sequence of Bovine Phenylethanolamine N-Methyltransferase: Partial Amino Acid Homology With Rat Tyrosine Hydroxylase." *PNAS*. 83.15(1986):5454-5458.

Christenson et al. "Tissue Reaction to Intraperitoneal Polymer Implants: Species Difference and Effects of Corticords and Doxorubicin." *J. Biomed. Mater. Res*. 23(1989):705-718.

Colton et al. "Chapter 47: Hemodialysis: Physical Principles and Technical Considerations." *The Kidney*. Brenner et al., eds. Philadelphia: W.B. Saunders Co. 2(1981):2425-2489.

Colton. "Engineering Challenges in Cellencapsulation Technology." *Trends Biotechnol*. 14.5(1996):158-162.

Dionne et al. "Diffusion Coefficient of Proteins Through High Flux Ultra-Filtration Membranes." *ASAIO Abstracts. 39th Annual Meeting*. (Apr. 29, 30 and May 1, 1993):99.

DrugBank DB00112, retrieved May 4, 2012.

DrugBank DB01270, retrieved May 4, 2012.

Dunn et al. "ARPE-19, A Human Retinal Pigment Epithelial Cell Line With Differentiated Properties." *Exp. Eye Res*. 62.2(1996):155-169.

Dunn et al. "Use of the ARPE-19 Cell Line as a Model of RPE Polarity: Basolateral Secretion of FGF5." *IOVS*. 39.13(1998):2744-2749.

Faithfull. "Fluorocarbons: Current Status and Future Applications." *Anaesthesia*. 42(1987):234-242.

Finnemann et al. "Phagocytosis of Rod Outer Segments by Retinal Pigment Epithelial Cells Requires αvβ5 Integrin for Binding but not for Internalization." *PNAS*. 94.24(1997):12932-12937.

Fumia et al. "Human F(ab')$_2$-Containing Immune Complexes Together With Anti-Hinge Natural Antibodies Stimulate Complement Amplification in vitro and in vivo." *Mol. Immunol*. 45.10(2008):2951-2961.

GenBank Accession No. AF063658, May 16, 1998.

GenBank Accession No. BC032224, Jul. 15, 2006.

GenBank Accession No. NM_006206, Apr. 22, 2012.

GenBank Accession No. U01134, Feb. 2, 1994.

Handa et al. "The Advanced Glycation Endproduct Pentosidine Induces the Expression of PDGF-B in Human Retinal Pigment Epithelial Cells." *Exp. Eye Res*. 66.4(1998):411-419.

Holtkamp et al. "Polarized Secretion of IL-6 and IL-8 by Human Retinal Pigment Epithelia Cells." *Clin. Exp. Immunol*. 112.1(1998):34-43.

Ju et al. "Emulsions Containing Perfluorocarbon Support Cell Cultures." *NASA Tech Briefs MSC-21480*. 14.9(1990):99.

Khosla et al. "Cloned Hemoglobin Genes Enhance Growth of Cells." *NASA Tech Briefs NPO-17517*. 15.1(1991):54.

Lacy et al. "Maintenance of Normoglycemia in Diabetic Mice by Subcutaneous Xenografts of Encapsulated Islets." *Science*. 254(1991):1782-1784.

Lim et al. "Microencapsulated Islets as Bioartificial Endocrine Pancreas." *Science*. 210(1980):908-910.

Lutz et al. "Stimulation of COmplement AMplification by F(ab')2-Containing Immune Complexes and Naturally Occuring Anti-Hinge Antibodies, Possible Role in Systemic Inflammation." *Autoinflamm. Rev*. 7(2008):508-513.

Lysaght et al. "Recent Progress in Immunoisolated Cell Therapy." *J. Cell. Biochem*. 56.2(1994):196-203.

Maidji et al. "Accessory Human Cytomegalovirus Glycoprotein US9 in the Unique Short Component of of the Viral Genome Promotes Cell-to-Cell Transmission of Virus in Polarized Epithelial Cells." *J. Virol*. 70.12(1996):8402-8410.

Needleman et al. "A General Method Applicable to the Search for Similarities in the Amino Acid Sequence of Two Proteins." *J. Mol. Biol*. 48.3(1970):443-453.

Scharp et al. "Islet Immuno-Isolation: The Use of Hybrid Artificial Organs to Prevent Islet Tissue Rejection." *World J. Surg*. 8(1984):221-229.

Shilo et al. "DNA Sequences Homologous to Vertebrate Oncogenes are Conserved in *Drosophila melanogaster*." *PNAS*. 78.11(1981):6789-6792.

Siliprandi et al. "Nerve Growth Factor Promotes Functional Recovery of Retinal Ganglion Cells After Ischemia." *IOVS*. 34.12(1993):3232-3245.

Southern et al. "Transformation of Mammalian Cells to Antibiotic Resistance With a Bacterial Gene Under Control of the SV40 Early Region Promoter." *J. Mol. Appl. Genet*. 1.4(1982):327-341.

Southern. "Mammalian Cell Transformation With SV40 Hybrid Plasmid Vectors." *In Vitro*. 18.3(1981):315. (Abstract #167).

Sun. "Microencapsulated of Pancreatic Islet Cells: A Bioartifical Endocrine Pancreas." *Meth. Enzymol*. 137(1988):575-580.

Wilson et al. "The Oxygen Dependence of Mitochondrial Oxidative Phosphorylation Measured by a New Optical Method for Measuring Oxygen Concentration." *J. Biol. Chem*. 263.6(1988):2712-2718.

Girod, P-A et al., "Fast generation of high producer cho cell lines by an iterative transfection process", Microbial Cell Factories, 5(Suppl 1):S41 (2006).

* cited by examiner

Diagram of pCpGfree Expression Vector

|  | | | | | | | Section1 |
|---|---|---|---|---|---|---|---|
| Translation of p834 actual sequence | (1) | 1 | 10 | 20 | 30 | 40 | 50 | 69 |
| Translation of p873_aflibercept | (1) | MVSYWDTGVLLCALLSCLLLTGSSSSGSRSDTGRPFVEMYSEIPEIIHMTEGRELVIPCRVTSPNITVTL |
| Translation of Aflibercept R5 | (1) | MVSYWDTGVLLCALLSCLLLTGSSSSGS--DTGRPFVEMYSEIPEIIHMTEGRELVIPCRVTSPNITVTL |
|  | (1) | MVSYWDTGVLLCALLSCLLLTGSSSSGSRSDTGRPFVEMYSEIPEIIHMTEGRELVIPCRVTSPNITVTL |

P917 → Translation of Aflibercept R5

|  |  | | | | | | | Section2 138 |
|---|---|---|---|---|---|---|---|---|
| Translation of p834 actual sequence | (70) | 70 | 80 | 90 | 100 | 110 | 120 | |
| | (70) | KKFPLDTLIPDGKRIIWDSRKGFIISNATYKEIGLLTCEATVNGHLYKTNYLTHRQTNTIIDVVLSPSH |
| Translation of p873_aflibercept | (68) | KKFPLDTLIPDGKRIIWDSRKGFIISNATYKEIGLLTCEATVNGHLYKTNYLTHRQTNTIIDVVLSPSH |
| Translation of Aflibercept R5 | (70) | KKFPLDTLIPDGKRIIWDSRKGFIISNATYKEIGLLTCEATVNGHLYKTNYLTHRQTNTIIDVVLSPSH |

|  | | | | | | | | Section3 207 |
|---|---|---|---|---|---|---|---|---|
| Translation of p834 actual sequence | (139) | 139 | 150 | 160 | 170 | 180 | 190 | |
| | (139) | GIELSVGEKLVLNCTARTELNVGIDFNWEYPSSKHQHKKLVNRDLKTQSGSEMKKFLSTLTIDGVTRSD |
| Translation of p873_aflibercept | (137) | GIELSVGEKLVLNCTARTELNVGIDFNWEYPSSKHQHKKLVNRDLKTQSGSEMKKFLSTLTIDGVTRSD |
| Translation of Aflibercept R5 | (139) | GIELSVGEKLVLNCTARTELNVGIDFNWEYPSSKHQHKKLVNRDLKTQSGSEMKKFLSTLTIDGVTRSD |

|  | | | | | | | | Section4 276 |
|---|---|---|---|---|---|---|---|---|
| Translation of p834 actual sequence | (208) | 208 | 220 | 230 | 240 | 250 | 260 | |
| | (208) | QGLYTCAASSGLMTKKNSTFVRVHEK*EFEPK*SCDKTHTCPPCPAPELLGGPSVFLFPPKPKDTLMISRT |
| Translation of p873_aflibercept | (206) | QGLYTCAASSGLMTKKNSTFVRVHEK------DKTHTCPPCPAPELLGGPSVFLFPPKPKDTLMISRT |
| Translation of Aflibercept R5 | (208) | QGLYTCAASSGLMTKKNSTFVRVHEK------DKTHTCPPCPAPELLGGPSVFLFPPKPKDTLMISRT |

|  | | | | | | | | Section5 345 |
|---|---|---|---|---|---|---|---|---|
| Translation of p834 actual sequence | (277) | 277 | 290 | 300 | 310 | 320 | 330 | |
| | (277) | PEVTCVVVDVSHEDPEVKFNWYVDGVEVHNAKTKPREEQYNSTYRVVSVLTVLHQDWLNGKEYKCKVSN |
| Translation of p873_aflibercept | (268) | PEVTCVVVDVSHEDPEVKFNWYVDGVEVHNAKTKPREEQYNSTYRVVSVLTVLHQDWLNGKEYKCKVSN |
| Translation of Aflibercept R5 | (270) | PEVTCVVVDVSHEDPEVKFNWYVDGVEVHNAKTKPREEQYNSTYRVVSVLTVLHQDWLNGKEYKCKVSN |

|  | | | | | | | | Section6 414 |
|---|---|---|---|---|---|---|---|---|
| Translation of p834 actual sequence | (346) | 346 | 360 | 370 | 380 | 390 | 400 | |
| | (346) | KALPAPIEKTISKAKGQPREPQVYTLPPSRDELTKNQVSLTCLVKGFYPSDIAVEWESNGQPENNYKTT |
| Translation of p873_aflibercept | (337) | KALPAPIEKTISKAKGQPREPQVYTLPPSRDELTKNQVSLTCLVKGFYPSDIAVEWESNGQPENNYKTT |
| Translation of Aflibercept R5 | (339) | KALPAPIEKTISKAKGQPREPQVYTLPPSRDELTKNQVSLTCLVKGFYPSDIAVEWESNGQPENNYKTT |

|  | | | | | Section7 467 |
|---|---|---|---|---|---|---|
| Translation of p834 actual sequence | (415) | 415 | 430 | 440 | 450 | |
| | (415) | PPVLDSDGSFFLYSKLTVDKSRWQQGNVFSCSVMHEALHNHYTQKSLSLSPGK |
| Translation of p873_aflibercept | (406) | PPVLDSDGSFFLYSKLTVDKSRWQQGNVFSCSVMHEALHNHYTQKSLSLSPG- |
| Translation of Aflibercept R5 | (408) | PPVLDSDGSFFLYSKLTVDKSRWQQGNVFSCSVMHEALHNHYTQKSLSLSPG- |

FIG. 15

```
                                            Signal                                              Chimeric Receptor Domains                                                        100
Aflibercept VEGF-trap WHO         (1)   ------------------------------------SDTGRPFVEMYSEIPEIIHMTEGRELVIPCRVTSPNITVTLKKFPLDTLIPDGKRIIWDSRKGFIISNATYK
VEGFR1R2-FcdeltaC1 from patent 7531173  (1)   MVSYWDTGVLLCALLSCLLLTGSSSG--SDTGRPFVEMYSEIPEIIHMTEGRELVIPCRVTSPNITVTLKKFPLDTLIPDGKRIIWDSRKGFIISNATYK
Translation of p834 actual sequence (1)   MVSYWDTGVLLCALLSCLLLTGSSSGSRSDTGRPFVEMYSEIPEIIHMTEGRELVIPCRVTSPNITVTLKKFPLDTLIPDGKRIIWDSRKGFIISNATYK
                                                                                                                                                                                  200
Aflibercept VEGF-trap WHO        (73)   EIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTI
VEGFR1R2-FcdeltaC1 from patent 7531173 (99)   EIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTI
Translation of p834 actual sequence (101)  EIGLLTCEATVNGHLYKTNYLTHRQTNTIIDVVLSPSHGIELSVGEKLVLNCTARTELNVGIDFNWEYPSSKHQHKKLVNRDLKTQSGSEMKKFLSTLTI
                                                                                                                                                                                  300
Aflibercept VEGF-trap WHO       (173)   DGVTRSDQGLYTCAASSGLMTKKNSTFVRVHEK------DKTHTCPPCPAPELLGGPSVFLFPPKPKDTLMISRTPEVTCVVVDVSHEDPEVKFNWYVD
VEGFR1R2-FcdeltaC1 from patent 7531173 (199)  DGVTRSDQGLYTCAASSGLMTKKNSTFVRVHEK------DKTHTCPPCPAPELLGGPSVFLFPPKPKDTLMISRTPEVTCVVVDVSHEDPEVKFNWYVD
Translation of p834 actual sequence (201)  DGVTRSDQGLYTCAASSGLMTKKNSTFVRVHEKEFPKSCDKTHTCPPCPAPELLGGPSVFLFPPKPKDTLMISRTPEVTCVVVDVSHEDPEVKFNWYVD
                                                                                                                                                                                  400
Aflibercept VEGF-trap WHO       (266)   GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVE
VEGFR1R2-FcdeltaC1 from patent 7531173 (292)  GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVE
Translation of p834 actual sequence (301)  GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVE
                                                                                                                               467
Aflibercept VEGF-trap WHO       (366)   WESNGQPENNYKTTPPVLDSDGSFFLYSKLTVDKSRWQQGNVFSCSVMHEALHNHYTQKSLSLSPG-
VEGFR1R2-FcdeltaC1 from patent 7531173 (392)  WESNGQPENNYKTTPPVLDSDGSFFLYSKLTVDKSRWQQGNVFSCSVMHEALHNHYTQKSLSLSPGK
Translation of p834 actual sequence (401)  WESNGQPENNYKTTPPVLDSDGSFFLYSKLTVDKSRWQQGNVFSCSVMHEALHNHYTQKSLSLSPGK
                                                                         Fc-Domain
```

FIG. 16

CELL LINES THAT SECRETE ANTI-ANGIOGENIC ANTIBODY-SCAFFOLDS AND SOLUBLE RECEPTORS AND USES THEREOF

RELATED APPLICATIONS

This application claims priority to U.S. Ser. No. 61/419,138, filed Dec. 2, 2010, which is incorporated herein by reference in its entirety.

INCORPORATION-BY-REFERENCE OF SEQUENCE LISTING

The contents of the text file named "NETE-059/001US_SeqList_ST25.txt", which was created on Jun. 10, 2015 and is 99 KB in size, are hereby incorporated by reference in their entirety.

FIELD OF THE INVENTION

The present invention relates generally to the field of encapsulated cell therapy.

BACKGROUND OF THE INVENTION

Many clinical conditions, deficiencies, and disease states can be remedied or alleviated by supplying to the patient one or more biologically active molecules produced by living cells or by removing from the patient deleterious factors which are metabolized by living cells. In many cases, these molecules can restore or compensate for the impairment or loss of organ or tissue function. Accordingly, many investigators have attempted to reconstitute organ or tissue function by transplanting whole organs, organ tissue, and/or cells, which provide secreted products or affect metabolic functions. However, while such transplantation can provide dramatic benefits, it is limited in its application by the relatively small number of organs that are suitable and available for grafting. Moreover, in general, transplantation patients must be immunosuppressed in order to avert immunological rejection of the transplant, which results in loss of transplant function and eventual necrosis of the transplanted tissue or cells. Likewise, in many cases, the transplant must remain functional for a long period of time, even for the remainder of the patient's lifetime. It is both undesirable and expensive to maintain a patient in an immunosuppressed state for a substantial period of time.

In one example where additional effective therapies are still need are vision-threatening disorders of the eye. One major problem in treatment of such diseases is the inability to deliver them there at therapeutically effective concentrations.

Many growth factors have shown promise in the treatment of ocular disease. For example, BDNF and CNTF have been shown to slow degeneration of retinal ganglion cells and decrease degeneration of photoreceptors in various animal models. See, e.g., Genetic Technology News, vol. 13, no. 1 (January 1993). Additionally, nerve growth factor has been shown to enhance retinal ganglion cell survival after optic nerve section and has also been shown to promote recovery of retinal neurons after ischemia. See, e.g., Siliprandi, et al., Invest. Ophthalmol. & Vis. Sci., 34, pp. 3232-3245 (1993). More recently, antibody scaffold based biologics have been designed and used for eye disorders including, for example, full antibodies (e.g., Bevacizumab) and antibody scaffold Fab fragments (e.g., Ranibizumab), and immunoglobulin Fc (e.g., Aflibercept).

A desirable alternative to transplantation procedures is the implantation of cells or tissues within a physical barrier which will allow diffusion of nutrients, metabolites, and secreted products, but will block the cellular and molecular effectors of immunological rejection. A variety of devices which protect tissues or cells producing a selected product from the immune system have been explored. See, e.g., U.S. Pat. No. 5,158,881; WO92/03327; WO91/00119; and WO93/00128, each of which is incorporated herein by reference in its entirety. These devices include, for example, extravascular diffusion chambers, intravascular diffusion chambers, intravascular ultrafiltration chambers, and implantation of microencapsulated cells. See Scharp, D. W., et al., World J. Surg., 8, pp. 221-9 (1984). See, e.g., Lim et al., Science 210: 908-910 (1980); Sun, A. M., Methods in Enzymology 137: 575-579 (1988); WO 93/03901; and U.S. Pat. No. 5,002,661. The use of such devices would alleviate the need to maintain the patient in an immunosuppressed state. However, none of these approaches have been satisfactory for providing long-term transplant function.

Thus, methods of delivering appropriate quantities of needed substances, such as, for example, neurotrophic factors, anti-angiogenic factors, anti-inflammatory factors, enzymes, hormones, or other factors, or of providing other needed metabolic functions, to the eye or other parts of the body for an extended period of time are needed.

SUMMARY OF THE INVENTION

Provided herein are isolated nucleic acids encoding anti-angiogenic proteins including antibody-scaffolds, soluble Vascular Endothelial Growth Factor (VEGF) receptors, and/or Platelet Derived Growth Factors (PDGF) receptors wherein the nucleic acids comprise or consist of a sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO: 19, SEQ ID NO: 21, SEQ ID NO:23, SEQ ID NO:25, SEQ ID NO:27, SEQ ID NO:29, and SEQ ID NO:31. The invention also provides nucleic acid molecules encoding a polypeptide comprising or consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO: 20, SEQ ID NO: 22, SEQ ID NO:24, SEQ ID NO:26, SEQ ID NO:28, SEQ ID NO:28, SEQ ID NO:30, and SEQ ID NO:32.

Also provided are nucleic acid molecules encoding a polypeptide having a sequence that is at least 95% identical to any of SEQ ID NOs: 2, 4, 6, 8, 10, 12, 14, 16, 18, 20, 22, 24, 26, 28, 30, or 32. Alternatively, the nucleic acid molecules may be the complement of such a nucleic acid molecule. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

As used herein, an "isolated" nucleic acid molecule is one that is separated from other nucleic acid molecules which are present in the source of the nucleic acid. Preferably, an "isolated" nucleic acid is free of sequences which flank the nucleic acid (i.e., sequences located at the 5' and 3' ends of the nucleic acid) in the genomic DNA of the organism from which the nucleic acid is derived. For example, in various embodiments, the nucleic acid molecules of the invention can contain less than about 5 kb, 4 kb, 3 kb, 2 kb, 1 kb, 0.5 kb, or 0.1 kb of nucleotide sequences which flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized. For example, those skilled in the art will recognize that the "isolated" nucleic acid may be a completely synthetic molecule that originally comes from phage display screening. Thus, in this context, an "isolated" nucleic acid could be a synthetic molecule substantially free of other cellular material, culture medium, chemical precursors, chemicals, etc.

A nucleic acid molecule of the present invention (e.g., a nucleic acid molecule having a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO:15, SEQ ID NO:17, SEQ ID NO: 19, SEQ ID NO: 21, SEQ ID NO:23, SEQ ID NO:25, SEQ ID NO:27, SEQ ID NO:29, and SEQ ID NO:31, encoding a polypeptide having a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO:18, SEQ ID NO: 20, SEQ ID NO: 22, SEQ ID NO:24, SEQ ID NO:26, SEQ ID NO:28, SEQ ID NO:30, and SEQ ID NO:32 or a complement of any of these nucleotide sequences) can be made using standard molecular biology techniques and the sequence information provided herein. Using all or a portion of these nucleic acid sequences a hybridization probe, or soluble VEGF receptor or PDGF receptor molecules can be isolated using standard hybridization and cloning techniques (e.g., as described in Sambrook et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

Any of the nucleic acids of the invention can be amplified using cDNA, mRNA or, alternatively, genomic DNA, as a template and appropriate oligonucleotide primers according to standard PCR amplification and assembly techniques. The nucleic acid so amplified can be cloned into an appropriate vector and characterized by DNA sequence analysis. Furthermore, oligonucleotides corresponding to anti-angiogenic antibody-scaffold or soluble VEGFR or PDGFR nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at least 6 contiguous nucleotides of SEQ ID NO: 1, 3, 5, 7, 9, 11, 13, 15, 17, 19, 21, 23, 25, 27, 29, or 31 or a complement thereof. Oligonucleotides may be chemically synthesized and may be used as probes.

In other embodiments, an isolated nucleic acid molecule of the invention comprises a nucleic acid molecule that is a complement of the nucleotide sequence shown in SEQ ID NO: 1, 3, 5, 7, 9, 11, 13, 15, 17, 19, 21, 23, 25, 27, 29, or 31. A nucleic acid molecule that is complementary to these nucleotide sequences is one that is sufficiently complementary to the nucleotide sequence that it can hydrogen bond with little or no mismatches, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO: 1, 3, 5, 7, 9, 11, 13, 15, 17, 19, 21, 23, 25, 2, 29, or 31, e.g., a fragment that can be used as a probe or primer or a fragment encoding a biologically active portion of any of the anti-angiogenic antibody-scaffolds or soluble VEGF receptors or PDGF receptors of the invention. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 50-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

The invention further encompasses nucleic acid molecules that differ from the nucleotide sequence shown in SEQ ID NO: 1, 3, 5, 7, 9, 11, 13, 15, 17, 19, 21, 23, 25, 27, 29, or 31 due to degeneracy of the genetic code and, thus, encode the same anti-angiogenic antibody-scaffolds or soluble VEGFR or PDGFR proteins as that encoded by the nucleotide sequence shown in SEQ ID NO: 1, 3, 5, 7, 9, 11, 13, 15, 17, 19, 21, 23, 25, 27, 29, or 31.

In another embodiment, an isolated nucleic acid molecule of the invention is at least 6 nucleotides in length and hybridizes under stringent conditions to the nucleic acid molecule comprising the nucleotide sequence of SEQ ID NO: 1, 3, 5, 7, 9, 11 13, 15, 17, 19, 21, 23, 25, 27, 29, or 31. In another embodiment, the nucleic acid is at least 10, 25, 50, 100, 250, 500, 1000, 1500, 2000, or more nucleotides in length. In another embodiment, an isolated nucleic acid molecule of the invention hybridizes to the coding region, for example SEQ ID NO: 1, 3, 5, 7, 9, 11, 13, 15, 17, 19, 21, 23, 25, 27, 29, or 31.

As used herein, the term "hybridizes under stringent conditions" is intended to describe conditions for hybridization and washing under which nucleotide sequences at least 60% homologous to each other typically remain hybridized to each other. Moreover, as used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), CURRENT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789-6792.

Also provided are polypeptides encoded by any of the nucleic acid molecules described herein. For example, these polypeptides can be anti-angiogenic antibody-scaffolds and/or soluble VEGF receptors or PDGF receptors. In some embodiments, the anti-angiogenic antibody-scaffolds and/or soluble VEGF receptors or PDGF receptors described herein bind (e.g., preferentially) to VEGF. The binding of these anti-angiogenic antibody-scaffolds and/or soluble VEGF receptors to VEGF, or in conjunction with PDGF receptors to PDGF inhibits endothelial cell proliferation and vascular permeability.

The invention also involves an isolated polypeptide that is at least 80% identical to a polypeptide having an amino acid sequence of SEQ ID NOs: 2, 4, 6, 8, 10, 12, 14, 16, 18, 20, 22, 24, 26, 28, 30, or 32. Alternatively, the isolated polypeptide is at least 80% homologous to a fragment (i.e., at least 6 contiguous amino acids) of a polypeptide having an amino acid sequence of SEQ ID NOs: 2, 4, 6, 8, 10, 12, 14, 16, 18, 20, 22, 24, 26, 28, 30, or 32. Moreover, the invention also includes isolated polypeptides that are at least 80% homologous to a derivative, analog, or homolog of a polypeptide having an amino acid sequence of SEQ ID NOs: 2, 4, 6, 8, 10, 12, 14, 16, 18, 20, 22, 24, 26, 28, 30, or 32. Similarly, the invention also provides an isolated polypeptide that is at least 80% identical to an allelic variant of a polypeptide having an amino acid sequence of SEQ ID NOs: 2, 4, 6, 8, 10, 12, 14, 16, 18, 20 22, 24, 26, 28, 30, or 32. Those skilled in the art will recognize that such polypeptides should be encoded by a nucleic acid molecule capable of hybridizing to a nucleic acid molecule of SEQ ID NOs: 1, 3, 5, 7, 9, 11, 13, 15, 17, 19, 21, 23, 25, 27, 29, or 31 under stringent conditions.

As used herein, the terms "protein" and "polypeptide" are intended to be interchangeable. The novel polypeptides of the invention include the anti-angiogenic antibody-scaffolds and soluble VEGF receptor or PDGF receptor polypeptides whose sequence is provided in SEQ ID NOs: 2, 4, 6, 8, 10, 12, 14, 16, 18, 20, 22, 24, 26, 28, 30, or 32. The invention also includes mutant or variant polypeptides any of whose residues may be changed from the corresponding residue shown in SEQ ID NOs: 2, 4, 6, 8, 10, 12, 14, 16, 18, 20, 22, 24, 26, 28, 30, or 32, while still encoding a polypeptide that maintains its anti-angiogenic antibody-scaffold and/or soluble VEGF receptor or PDGF receptor activities and physiological functions, or functional fragment(s) thereof. In the mutant or variant protein, up to 20% or more of the residues may be so changed.

In general, an anti-angiogenic antibody-scaffold or a soluble VEGF receptor or PDGF receptor variant that preserves anti-angiogenic or soluble VEGFR-like or PDGFR-like function includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution(s), insertion(s), or deletion(s) is encompassed by the invention. In favorable circumstances, the substitution is a conservative substitution.

Those skilled in the art will recognize that the invention also pertains to isolated anti-angiogenic antibody-scaffolds and soluble VEGFR or PDGFR polypeptides, and biologically active portions thereof, or derivatives, fragments, analogs or homologs thereof. Anti-angiogenic antibody-scaffolds and soluble VEGFR or PDGFR constructs described herein can be isolated from cells or tissue sources by an appropriate purification scheme using standard protein purification techniques. In another embodiment, the anti-angiogenic antibody-scaffolds and soluble VEGFR or PDGFR polypeptides of the invention are produced by recombinant DNA techniques. As an alternative to recombinant expression, an anti-angiogenic antibody-scaffold or a soluble VEGFR or PDGFR protein or polypeptide can be synthesized chemically using standard peptide synthesis techniques.

An "isolated" or "purified" polypeptide or biologically active portion thereof is substantially free of cellular material or other contaminating proteins or polypeptides from the cell or tissue source from which the anti-angiogenic antibody-scaffold or soluble VEGFR or PDGFR polypeptide is derived, or substantially free from chemical precursors or other chemicals when chemically synthesized. The language "substantially free of cellular material" includes preparations of anti-angiogenic antibody-scaffolds or soluble VEGFR or PDGFR polypeptides in which the polypeptide is separated from cellular components of the cells from which it is isolated or recombinantly produced. For example, the language "substantially free of cellular material" includes preparations of anti-angiogenic antibody-scaffold or VEGFR or PDGFR polypeptide having less than about 30% (by dry weight) of non-anti-angiogenic antibody-scaffold or non-VEGFR or PDGFR protein (also referred to herein as a "contaminating protein"), more preferably less than about 20% of non-anti-angiogenic antibody-scaffold or non-VEGFR or non-PDGFR protein, still more preferably less than about 10% of non-anti-angiogenic antibody-scaffold or non-VEGFR or non-PDGFR protein, and most preferably less than about 5% non-anti-angiogenic antibody-scaffold or non-VEGFR non-PDGFR protein. When the anti-angiogenic antibody-scaffold or VEGFR or PDGFR polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

Similarly, the language "substantially free of chemical precursors or other chemicals" includes preparations of anti-angiogenic antibody-scaffold or soluble VEGFR or PDGFR polypeptide in which the polypeptide is separated from chemical precursors or other chemicals that are involved in the synthesis of the polypeptide. For example, the language "substantially free of chemical precursors or other chemicals" includes preparations of anti-angiogenic antibody-scaffolds or soluble VEGFR or PDGFR polypeptide having less than about 30% (by dry weight) of chemical precursors or non-anti-angiogenic antibody-scaffolds or non-VEGFR or non-PDGFR chemicals, more preferably less than about 20% chemical precursors or non-anti-angiogenic antibody-scaffolds or non-VEGFR or non-PDGFR chemicals, still more preferably less than about 10% chemical precursors or non-anti-angiogenic antibody-scaffold or non-VEGFR or non-PDGFR chemicals, and most preferably less than about 5% chemical precursors or non-anti-angiogenic antibody-scaffolds or non-VEGFR non-PDGFR chemicals.

Biologically active portions of an anti-angiogenic antibody-scaffold or a soluble VEGFR or PDGFR polypeptide construct of the invention include peptides comprising amino acid sequences sufficiently homologous to or derived from the amino acid sequence of the anti-angiogenic antibody-scaffolds or soluble VEGFR or PDGFR polypeptides, e.g., the amino acid sequence shown in SEQ ID NOs: 2, 4, 6, 8, 10, 12, 14, 16, 18, 20, 22, 24, 26, 28, 30, or 32 that include fewer amino acids than the full length anti-angiogenic antibody-scaffolds or soluble VEGFR or PDGFR constructs described herein, and exhibit at least one activity of an anti-angiogenic antibody-scaffold or a soluble VEGFR or PDGFR polypeptide of the invention. Typically, biologically active portions comprise a domain or motif with at least one activity of the anti-angiogenic antibody-scaffold or soluble VEGFR or PDGFR polypeptide.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443-453. The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

The invention also provides for anti-angiogenic antibody-scaffold or soluble VEGF or PDGFR receptor chimeric or fusion proteins. An anti-angiogenic antibody-scaffold or a soluble VEGFR or PDGFR chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide).

The invention further provides vectors containing any of the nucleic acid molecules of the invention. Specifically, the invention also pertains to vectors, preferably expression vectors, containing a nucleic acid encoding the anti-angiogenic antibody-scaffolds or soluble VEGFR or PDGFR polypeptides of the invention, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, adeno-associated viruses, and transposon based recombination systems), which serve equivalent functions.

The recombinant expression vectors of the invention comprise any of the nucleic acids of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., anti-angiogenic antibody-scaffolds, soluble VEGFR or PDGFR polypeptides, mutant forms of anti-angiogenic antibody-scaffolds, mutant forms of soluble VEGFR or PDGFR polypeptides, fusion proteins, etc.).

The recombinant expression vectors of the invention can be designed for expression of anti-angiogenic antibody-scaffolds or soluble VEGFR or PDGFR constructs of the invention in prokaryotic or eukaryotic cells. Other suitable expression systems for both prokaryotic and eukaryotic cells are known in the art. (See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989).

In addition, the invention also provides host cells or cell lines containing such vectors (or any of the nucleic acid molecules described herein). As used herein, the terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. By way of non-limiting example, the host cell may be an ARPE-19 cell. However, other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, methotrexate, and/or blasticidin. Nucleic acid encoding a selectable marker can be introduced into a host cell on the same vector as that encoding the anti-angiogenic antibody-scaffold or soluble VEGF or PDGF receptor construct or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) any of the anti-angiogenic antibody-scaffolds or soluble VEGFR or PDGFR polypeptide constructs described herein. Accordingly, the invention further provides methods for producing these anti-angiogenic antibody-scaffolds or soluble VEGFR or PDGFR polypeptides using the host cells of the invention. In one embodiment, the method comprises culturing the host cell of invention (into which a recombinant expression vector encoding anti-angiogenic antibody-scaffolds or soluble VEGFR or PDGFR has been introduced) in a suitable medium such that anti-angiogenic antibody-scaffold or soluble VEGFR or PDGFR polypeptide is produced. In another embodiment, the method further comprises isolating anti-angiogenic antibody-scaffold or soluble VEGFR or PDGFR from the medium or the host cell.

Likewise, the invention also provides cell lines of ARPE-19 cells genetically engineered to produce a therapeutic amount of an anti-angiogenic antibody-scaffold or a soluble VEGF receptor or PDGF receptor, wherein the anti-angiogenic antibody-scaffold or soluble VEGF receptor or PDGF receptor is encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO: 19, SEQ ID NO:21, SEQ ID NO:23, SEQ ID NO:25, SEQ ID NO:27, SEQ ID NO:29 and SEQ ID NO:31. Similarly, the invention also provides cell lines of ARPE-19 cells genetically engineered to produce an anti-angiogenic antibody-scaffold or a soluble VEGF or PDGF receptor comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

Preferably, the therapeutic amount is at least 1 pg to 1000 μg/day/6 mm device. Those skilled in the art will recognize that the therapeutic amount can be any amount falling within this range (inclusive). Moreover, the cells lines and devices of the instant invention are able to express this therapeutic amount for a period of at least three weeks. In some embodiments, the therapeutic amount is at least 100-10,000 ng/day. In one non-limiting embodiment, the amount is at least 4 μg/day.

Also described herein are implantable cell culture devices containing a containing one or more of the cell lines of the invention (i.e., ARPE-19 cells that are genetically engineered to produce a therapeutic amount of any of the anti-angiogenic antibody-scaffolds and/or the soluble VEGF receptors or PDGFR receptor described herein) and a semipermeable membrane surrounding the core, wherein the membrane permits the diffusion of the anti-angiogenic antibody-scaffold or soluble VEGF receptor or PDGF receptor there through. The terms "capsule" and "device" are used interchangeably herein to refer to any bioartificial organ containing genetically engineered cells and cell lines (e.g., ARPE-19 cells or cell lines).

In some embodiments, the core additionally contains a matrix disposed within the semipermeable membrane. By way of non-limiting example, the matrix may include a hydrogel or extracellular matrix components. For example, the hydrogel may contain alginate cross-linked with a multivalent ion. In other embodiments, the matrix includes a plurality of monofilaments, wherein the monofilaments are twisted into a yarn or woven into a mesh or are twisted into a yarn that is in non-woven strands, and wherein the cells or tissue are distributed thereon. Those skilled in the art will recognize that the filamentous cell-supporting matrix can be made from a biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, and/or biocompatible metals. As used herein, an "internal scaffold" is one, non-limiting example of a "matrix" suitable for use in any of the devices of the invention.

In some embodiments, the cell encapsulation devices described herein also have a tether anchor. For example, the tether anchor may be an anchor loop that is adapted for anchoring the capsule to an ocular structure. Ay of the devices described herein are suitable for implantation into the eye or another target region of the body selected from the spleen, ear, heart, colon, liver, kidney, breast, joint, bone marrow, subcutaneous, and peritoneal spaces. By way of non-limiting example, the capsules can be implanted into the vitreous, the aqueous humor, the Subtenon's space, the periocular space, the posterior chamber, and/or the anterior chamber of the eye.

The jackets of the devices described herein preferably are made from a permselective, immunoisolatory membrane. For example, the jackets are made from an ultrafiltration membrane or a microfiltration membrane. Those skilled in the art will recognize that an ultrafiltration membrane typically has a pore size of 1-100 nm, whereas a microfiltration membrane typically has a pore size of 0.1-10 μM. In other embodiments, the jacket may be made from a non-porous membrane material (e.g., a hydrogel or a polyurethane). The terms "jacket" and "semi-permeable membrane" are used interchangeably herein.

In any of the devices described herein, the capsule can be configured as a hollow fiber or a flat sheet. Moreover, in various embodiments, at least one additional biologically active molecule can be co-delivered from these devices. For example, the at least one additional biologically active molecule can be from a non-cellular or a cellular source (i.e., the at least one additional biologically active molecule is produced by one or more genetically engineered ARPE-19 cell in the core).

Also provided herein are methods for treating ophthalmic disorders by implanting the implantable cell culture devices of the invention into the eye of a patient and allowing the anti-angiogenic antibody-scaffold or soluble VEGF receptor or PDGF receptor to diffuse from the device and bind to VEGF and/or PDGF in the eye, thereby treating the ophthalmic disorder. For example, the ophthalmic disorder to be treated can be selected from the group consisting of retinopathy of prematurity, diabetic macular edema, diabetic retinopathy, age-related macular degeneration, glaucoma, retinitis pigmentosa, cataract formation, retinoblastoma and retinal ischemia. In one preferred embodiment, age-related macular degeneration is wet form age-related macular degeneration. In another preferred embodiment, the ophthalmic disorder is diabetic retinopathy.

The invention further provides methods for inhibiting endothelial cell proliferation by implanting the implantable cell culture devices of the invention into a patient suffering from a cell proliferation disorder and allowing the anti-angiogenic antibody-scaffold or soluble VEGF receptor or PDGF receptor to diffuse from the device and bind to VEGF or PDGF, wherein the binding inhibits endothelial cell proliferation in the patient. For example, the disorder is selected from the group consisting of hematologic disorders, atherosclerosis, inflammation, increased vascular permeability and malignancy.

Also provided are methods of delivering an anti-angiogenic antibody-scaffold or a soluble VEGF receptor or PDGF receptor to a recipient host by implanting the implantable cell culture device described herein into a target region of the recipient host, wherein the encapsulated one or more ARPE-19 cells secrete the anti-angiogenic antibody-scaffold or soluble VEGF receptor or PDGF receptor at the target region. Preferred target regions include the central nervous system, including the brain, ventricle, spinal cord, or the aqueous and vitreous humors of the eye. Other target regions may include, but are not limited to, whole body for systemic delivery and/or localized target sites within or near organs in the body such as breast, colon, spleen, ovary, testicle, and/or bone marrow.

Those skilled in the art will recognize that in any of the methods described herein with regard to ocular implantation and/or disorders, between 0.1 pg and 1000 µg per patient per day of the anti-angiogenic antibody-scaffold or soluble VEGF receptors or PDGF receptor of the invention can diffuse from the implantable cell culture devices. However, for systemic implantation into other target regions of the body, the therapeutically effective amount could be upwards of 1000 mg per patient per day. For such systemic indications, those skilled in the art will recognize that far larger ECT devices would have to be employed.

Preferably, for ocular implantation, the therapeutic amount is any amount between 1 pg to 1000 µg/day/6 mm device (inclusive). In some embodiments, the therapeutic amount is at least 1000 ng/day (1.0 pcd). Moreover, the cells lines and devices of the instant invention are able to express this therapeutic amount for a period of at least three weeks.

In addition, the invention also provides methods for making the implantable cell culture devices of the invention. In one method, at least one ARPE-19 cell is genetically engineered to secrete an anti-angiogenic antibody-scaffold or a soluble VEGF receptor or PDGF receptor encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31 and the genetically modified ARPE-19 cells are encapsulated within a semipermeable membrane, wherein said membrane allows the diffusion of the anti-angiogenic antibody-scaffold or soluble VEGF receptor or PDGF receptor there through. In another method, at least one ARPE-19 cell is genetically engineering to secrete an anti-angiogenic antibody-scaffold or a soluble VEGF receptor or PDGF receptor comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32, and the genetically modified ARPE-19 cells are encapsulated within a semipermeable membrane, wherein said membrane allows the diffusion of the anti-angiogenic antibody-scaffold or the soluble VEGF receptor or PDGF receptor there through.

The invention also describes the use of one or more ARPE-19 cells that are genetically engineered to produce any of the polypeptides of the invention (e.g., SEQ ID NOs: 2, 4, 6, 8, 10, 12, 14, 16, 18, 20, 22, 24, 26, 28, 30, or 32) in the manufacture of any of the implantable cell culture devices according to the invention for treating vascular disorders including those in the eye, for example, by implantation of the device into the eye of the patient, or at other diseased site for localized and targeted anti-angiogenic factor delivery.

Moreover, any of the implantable cell culture devices described herein can be used for treating ophthalmic disorders by implantation of the device into the eye of a patient and by allowing the anti-angiogenic antibody-scaffolds or the soluble VEGF receptors or PDGF receptors of the invention to diffuse from the device and bind to VEGF and/or PDGF in the eye.

Also provided are one or more ARPE-19 cells that are genetically engineered to produce any of the polypeptides of the invention for treating ophthalmic disorders by implantation of any of the implantable cell culture devices of the invention into the eye of a patient and by allowing the anti-angiogenic antibody-scaffold or the soluble VEGF receptor or PDGF receptor to diffuse from the device and bind to VEGF or PDGF in the eye.

Any of the isolated nucleic acid molecules described herein can also be used in the manufacture of one or more ARPE-19 cells that are genetically engineered to produce one of the polypeptides of the invention for treating ophthalmic disorders by implantation into the eye of a patient an implantable cell culture device of the invention and by allowing the anti-angiogenic antibody-scaffold or the soluble VEGF receptor or PDGF receptor to diffuse from the device and bind to VEGF or PDGF in the eye. Moreover, any of the isolated nucleic acid molecules of the invention can also be used for treating ophthalmic disorders where treating comprises implanting into the eye of a patient an implantable cell culture device according to the instant invention and allowing the anti-angiogenic antibody-scaffold or the soluble VEGF receptor or PDGF receptor to diffuse from the device and bind to VEGF and/or PDGF in the eye, wherein said one or more ARPE-19 cells in said device have been genetically engineered with said isolated nucleic acid molecule to thereby produce any of the isolated polypeptides described herein.

In any of the embodiments described herein, the vascular disorder is selected from, but not limited to, for example, retinopathy of the prematurity, diabetic macular edema, diabetic retinopathy, age-related macular degeneration (e.g. wet form age-related macular degeneration), glaucoma, retinitis pigmentosa, cataract formation, retinoblastoma and retinal ischemia. Those skilled in the art will recognize that any of the devices described herein can also be used to treat a variety of non-ocular vascular disorders.

The invention also provides for the use of one or more ARPE-19 cells that are genetically engineered to produce a polypeptide of the invention (e.g., an anti-angiogenic-antibody scaffold or an anti-angiogenic molecule) in the manufacture of an implantable cell culture device according to the invention for inhibiting endothelial cell proliferation by implantation of the device into the eye of a patient suffering from a cell proliferation disorder and by allowing the anti-angiogenic antibody-scaffold or the soluble VEGF receptor or PDGF receptor to diffuse from the device and bind to VEGF and/or PDGF in the eye and to thereby inhibit endothelial cell proliferation in said patient. Likewise, the invention also provides implantable cell culture devices of the invention for inhibiting endothelial cell proliferation by implantation of the device into the eye of a patient suffering from a cell proliferation disorder and by allowing the anti-angiogenic antibody-scaffold or the soluble VEGF receptor or PDGF receptor to diffuse from the device and bind to VEGF and/or PDGF in the eye and thereby inhibit endothelial cell proliferation in said patient.

In other embodiments, the invention provides one or more ARPE-19 cells that are genetically engineered to produce any of the polypeptides of the invention for inhibiting endothelial cell proliferation by implantation of any of the implantable cell culture devices described herein into the eye of a patient suffering from a cell proliferation disorder and by allowing the anti-angiogenic antibody-scaffold or the soluble VEGF receptor or PDGF receptor to diffuse from the device and bind to VEGF or PDGF in the eye and thereby inhibit endothelial cell proliferation in said patient.

The use of any of the isolated nucleic acid molecules described herein in the manufacture of one or more ARPE-19 cells that are genetically engineered to produce the polypeptide(s) of the invention for inhibiting endothelial cell proliferation by implantation into the eye of a patient suffering from a cell proliferation disorder an implantable cell culture device according to the instant invention and by allowing the anti-angiogenic antibody-scaffold or the soluble VEGF receptor or PDGF receptor to diffuse from the device and bind to VEGF or PDGF in the eye and to thereby inhibit endothelial cell proliferation in said patient is also contemplated.

Moreover, the invention also provides any of the isolated nucleic acid molecules according to the invention for inhibiting endothelial cell proliferation, the treating comprising implanting into the eye of a patient suffering from a cell proliferation disorder an implantable cell culture device according to the invention and allowing the anti-angiogenic antibody-scaffold or the soluble VEGF receptor or PDGF receptor to diffuse from the device and bind to VEGF and/or PDGF in the eye and to thereby inhibit endothelial cell proliferation in said patient, and wherein said one or more ARPE-19 cells in said device have been genetically engineered with said isolated nucleic acid molecule to thereby produce a polypeptide of the invention.

Those skilled in the art will recognize that the cell proliferation disorder may be selected from the group consisting of hematologic disorders, atherosclerosis, inflammation, increased vascular permeability and malignancy and may be localized in various portions of the body, including, but not limited to, the eye. The ECT device, therefore, may be placed in proximity to those localized regions to treat the disorder mentioned.

Also provided herein is the use of one or more ARPE-19 cells that are genetically engineered to produce any of the polypeptides described herein in the manufacture of an implantable cell culture device according of the invention for delivering an anti-angiogenic antibody-scaffold or a soluble VEGF receptor or PDGF receptor to a recipient host by implantation of the device into a target region of the recipient host and wherein the encapsulated one or more ARPE-19 cells secrete the anti-angiogenic antibody-scaffold or the soluble VEGF receptor or PDGF receptor at the target region. Similarly, any of the implantable cell culture devices of the invention can be used for delivering an anti-angiogenic antibody-scaffold or a soluble VEGF receptor or PDGF receptor to a recipient host by implantation of the device into a target region of the recipient host and wherein the encapsulated one or more ARPE-19 cells secrete the anti-angiogenic antibody-scaffold or the soluble VEGF receptor or PDGF receptor at the target region.

Moreover, one or more ARPE-19 cells that are genetically engineered to produce any of the polypeptides described herein can be used for delivering an anti-angiogenic antibody-scaffold or a soluble VEGF receptor or PDGF receptor to a recipient host by implantation of any implantable cell culture devices of the invention into a target region of the recipient host and wherein the encapsulated one or more ARPE-19 cells secrete the anti-angiogenic antibody-scaffold or the soluble VEGF receptor or PDGF receptor at the target region.

Likewise, any of the isolated nucleic acid molecules described herein can be used in the manufacture of one or more ARPE-19 cells that are genetically engineered to produce any of the polypeptides described herein for delivering an anti-angiogenic antibody-scaffold or a soluble VEGF receptor or PDGF receptor to a recipient host by implantation into a target region of the recipient host an implantable cell culture device of the invention, wherein the encapsulated one or more ARPE-19 cells secrete the anti-angiogenic antibody-scaffold or the soluble VEGF receptor or PDGF receptor at the target region.

Any of the isolated nucleic acid molecules described herein can also be used for delivering an anti-angiogenic antibody-scaffold or a soluble VEGF receptor or PDGF receptor to a recipient host, said delivering comprising implanting into a target region of the recipient host an implantable cell culture device of the invention, wherein the encapsulated one or more ARPE-19 cells secrete the anti-angiogenic antibody-scaffold or the soluble VEGF receptor or PDGF receptor at the target region, and wherein said one or more ARPE-19 cells in said device have been genetically engineered with said isolated nucleic acid molecule to thereby produce any of the polypeptides of the invention.

Those skilled in the art will recognize that the target region is selected from the central nervous system, including the brain, ventricle, spinal cord, and the aqueous and vitreous humors of the eye. Other target regions may be situated elsewhere in the body, and ECT devices placed in proximity to those regions. Regions may include, but are not limited to, spleen, ear, heart, colon, liver, kidney, breast, joint, bone marrow, subcutaneous, and peritoneal spaces.

In addition, the invention also provides methods of producing an isolated polypeptide, the method comprising expressing any of the isolated nucleic acid molecules described herein and harvesting the expressed polypeptide.

The instant invention also provides cell lines comprising an ARPE-19 cell genetically engineered to produce a therapeutically effective amount of one or more anti-angiogenic antibody-scaffolds or anti-angiogenic molecules (e.g., at least 10,000 ng/day/$10^6$ cells). Preferably, the cell lines produce the therapeutically effective amount for a period of at least 3 months (i.e., 3, 6, 9, 12, 15, 18, 21, 24, or more months).

In some, non-limiting embodiments, the one or more anti-angiogenic antibody-scaffolds or anti-angiogenic molecules can be introduced into the ARPE-19 cell using an iterative transfection process. Specifically, the iterative transfection can be one transfection, two transfections, three transfections, or more transfections (e.g., 1, 2, 3, 4, 5, 6, 7, 8, 9, 10, or more transfections). When the iterative transfection process is one transfection, the cell line will contain one anti-angiogenic antibody-scaffold or anti-angiogenic molecule. When the iterative transfection process is two transfections, the cell line will contain two anti-angiogenic antibody-scaffolds or anti-angiogenic molecules. These may be the same or different anti-angiogenic antibody-scaffolds or anti-angiogenic molecules. When the iterative transfection process is three transfections, the cell line will contain three anti-angiogenic antibody-scaffolds or anti-angiogenic molecules. These may be the same or different anti-angiogenic antibody-scaffolds or anti-angiogenic molecules. Those skilled in the art will recognize that the number of transfections in the iterative transfection process will determine the number of (same or different) anti-angiogenic antibody-scaffolds and/or anti-angiogenic molecules in the resulting cell line.

In some embodiments, the cell line produces between 10,000 and 30,000 ng/day/$10^6$ cells of the one or more anti-angiogenic antibody-scaffold or anti-angiogenic molecules when the iterative transfection is one transfection. Preferably, the cell line produces about or at least 15,000 ng/day/$10^6$ cells of the one or more anti-angiogenic antibody-scaffold or anti-angiogenic molecules. In other embodiments, the cell line produces between 30,000 and 50,000 ng/day/$10^6$ cells of the one or more anti-angiogenic antibody-scaffold or anti-angiogenic molecules when the iterative transfection is two transfections. Preferably, the cell line produces about or at least 35,000 ng/day/$10^6$ cells of the one or more anti-angiogenic antibody-scaffold or anti-angiogenic molecules. In still other embodiments, the cell line produces between 50,000 and 75,000 ng/day/$10^6$ cells of the one or more anti-angiogenic antibody-scaffold or anti-angiogenic molecules when the iterative transfection is three transfections. Preferably, the cell line produces about or at least 70,000 ng/day/$10^6$ cells of the one or more anti-angiogenic antibody-scaffold or anti-angiogenic molecules.

The anti-angiogenic molecules can be, for example, a soluble VEGF receptor and/or a soluble PDGF receptor.

The iterative transfection process can be used to introduce multiple copies of the same anti-angiogenic antibody-scaffold(s) and/or anti-angiogenic molecule(s) into the ARPE-19 cells. Alternatively, the iterative transfection process can also be used to introduce multiple copies of different anti-angiogenic antibody-scaffold(s) and/or anti-angiogenic molecule(s) into the ARPE-19 cells.

In one embodiment, the ARPE-19 cell is genetically engineered using a vector comprising a soluble VEGF receptor encoded by a nucleic acid sequence of SEQ ID NO. 1 or a soluble VEGF receptor comprising an amino acid sequence of SEQ ID NO. 2.

The invention further provides any cell lines comprising an ARPE-19 cell genetically engineered to produce a therapeutically effective amount of one or more anti-angiogenic antibody-scaffolds or anti-angiogenic molecules, wherein the therapeutically effective amount is at least 10,000 ng/day/$10^6$ cells (e.g., at least 15,000, 20,000, 25,000, 30,000, 35,000, 40,000, 45,000, 50,000, 55,000, 60,000, 65, 000, 70,000, 75,000, or more ng/day/$10^6$ cells. Such cell lines are capable of producing this therapeutically effective amount for at least 3 months (e.g., at least 6, 9, 12, 15, 18, 21, or 24 months) or longer. Those skilled in the art will recognize that, such cell lines can, in some embodiments, be produced using an iterative transfection process, as described herein. However, other methods known in the art can also be used to obtain production of the therapeutically effective amount of the one or more anti-angiogenic antibody-scaffolds or anti-angiogenic molecules.

Any of the cell lines described herein can be genetically engineered to secrete an anti-angiogenic antibody-scaffold or a soluble VEGF receptor or PDGF receptor encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. Likewise, any of the cell lines described herein can be genetically engineered to secrete an anti-angiogenic antibody-scaffold or a soluble VEGF receptor or PDGF receptor comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30 and SEQ ID NO:32.

Also described herein are implantable cell culture devices containing a core containing one or more of the cell lines of the invention (i.e., ARPE-19 cells that are genetically engineered using an iterative transfection process to produce a therapeutically effective amount of any of the anti-angiogenic antibody-scaffolds and/or the anti-angiogenic molecules described herein or ARPE-19 cells genetically engineered to secrete at least 10,000 ng/day/$10^6$ cells) and a semipermeable membrane surrounding the core, wherein the membrane permits the diffusion of the one or more anti-angiogenic antibody-scaffolds and/or anti-angiogenic molecules there through.

In some embodiments, the core contains 0.5-1.0×$10^6$ cells.

The core may additionally contain a matrix disposed within the semipermeable membrane. In other embodiments, the matrix includes a plurality of monofilaments, wherein the monofilaments are twisted into a yarn or woven into a mesh or are twisted into a yarn that is in non-woven strands, and wherein the cells or tissue are distributed thereon. Those skilled in the art will recognize that the monofilaments can be made from a biocompatible material selected from acrylic, polyester, polyethylene, polypropylene polyacetonitrile, polyethylene terephthalate, nylon, polyamides, polyurethanes, polybutester, silk, cotton, chitin, carbon, and/or biocompatible metals. For example, the monofilaments are polyethylene terephthalate (PET) fibers that comprises between 40-85% of internal volume of the device.

The cell encapsulation devices described herein can also have a tether anchor. For example, the tether anchor may be an anchor loop that is adapted for anchoring the device to an ocular structure.

Any of the devices described herein can be implanted into (or are for implantation) the eye or another target region of the body, such as, for example, the spleen, ear, heart, colon, liver, kidney, breast, joint, bone marrow, subcutaneous, and/or peritoneal spaces. By way of non-limiting example, the devices can be implanted into (or are for implantation in) the vitreous, the aqueous humor, the Subtenon's space, the periocular space, the posterior chamber, and/or the anterior chamber of the eye.

The semi-permeable membrane of the devices described herein preferably is made from a permselective, immunoprotective membrane. In other embodiments, the semi-permeable membrane is made from an ultrafiltration membrane or a microfiltration membrane. Those skilled in the art will recognize that a semi-permeable membrane typically has a median pore size of about 100 nm.

In still other embodiments, the semi-permeable membrane may be made from a non-porous membrane material (e.g., a hydrogel or a polyurethane). In any of the devices described herein, the nominal molecule weight cutoff (MWCO) of the semi-permeable membrane is 500 kD. Preferably, the semi-permeable membrane is between about 90-120 um thick. Any of the devices described herein can be configured as a hollow fiber or a flat sheet. The length of the device can be between about 4 mm-11 mm. In some embodiments, the device has an internal diameter of between about 0.9 mm-1.2 mm. In one preferred embodiment, the ends of the device are sealed using methyl methacrylate.

Any device of the instant invention may include one, two, three, four, five, six, seven or all of the following additional characteristics:

a. the core contains between 0.5-1.0×$10^6$ ARPE-19 cells;
b. the length of the device is between 4 mm-11 mm;
c. the internal diameter of the device is between 0.9-1.2 mm;
d. the ends of the device are sealed using methyl methacrylate;
e. the semi-permeable membrane has a median pore size of about 100 nm;
f. the nominal molecular weight cut off (MWCO) of the semi-permeable membrane is 500 kD;
g. the semi-permeable membrane is between 90-120 μm thick;

h. the core contains comprises an internal scaffold, wherein the scaffold comprises polyethylene terephthalate (PET) fibers that comprises between 40-85% of internal volume of the device; and i. any combination(s) thereof.

Moreover, in various embodiments, at least one additional biologically active molecule can be co-delivered from these devices. For example, the at least one additional biologically active molecule can be from a non-cellular or a cellular source (i.e., the at least one additional biologically active molecule is produced by one or more genetically engineered ARPE-19 cell in the core).

The invention further provides uses of any of the implantable cell culture devices of the invention to deliver an appropriate therapeutic dose of the one or more anti-angiogenic antibody-scaffolds or anti-angiogenic molecules to an eye of a subject, wherein the therapeutic dose is at least 100 ng/day/eye (e.g., at least 100, 200, 300, 400, 500, 1000, 1500, 2000, 2500, 3000, 3500, 4000, or more ng/day/eye). Likewise, the invention also provides one or more anti-angiogenic antibody-scaffolds or anti-angiogenic molecules for use in treating a subject in need thereof by delivering an appropriate therapeutic dose of the one or more anti-angiogenic antibody-scaffolds or anti-angiogenic molecules to an eye of the subject, wherein the therapeutic dose is at least 100 ng/day/eye (e.g., at least 100, 200, 300, 400, 500, 1000, 1500, 2000, 2500, 3000, 3500, 4000, or more ng/day/eye).

Also provided herein are methods for treating ophthalmic disorders by implanting any of the implantable cell culture devices of the invention into the eye of a patient and allowing the anti-angiogenic antibody-scaffolds or anti-angiogenic molecules to diffuse from the device and bind to VEGF and/or PDGF in the eye, thereby treating the ophthalmic disorder. In some embodiments, the invention provides cell lines (i.e., any of the cell lines described herein) for use in treating ophthalmic disorders, wherein the cell lines are incorporated in an implantable cell culture device, wherein the devices are implanted into the eye of a patient, and wherein the anti-angiogenic antibody-scaffolds or anti-angiogenic molecules to diffuse from the device and bind to VEGF and/or PDGF in the eye, thereby treating the ophthalmic disorder. For example, the ophthalmic disorder to be treated can be selected from retinopathy of prematurity, diabetic macular edema, diabetic retinopathy, age-related macular degeneration, glaucoma, retinitis pigmentosa, cataract formation, retinoblastoma and retinal ischemia. In one preferred embodiment, age-related macular degeneration is wet form age-related macular degeneration. In one preferred embodiment, the ophthalmic disorder is diabetic retinopathy.

The invention further provides methods for inhibiting endothelial cell proliferation or vascularization by implanting the implantable cell culture devices of the invention into a patient suffering from a cell proliferation disorder and allowing the anti-angiogenic antibody-scaffold or the anti-angiogenic molecule to diffuse from the device and bind to VEGF and/or PDGF, wherein the binding inhibits endothelial cell proliferation or vascularization in the patient. For example, the disorder may be selected from hematologic disorders, atherosclerosis, inflammation, increased vascular permeability and malignancy. In such methods, the therapeutically effective amount per patient per day of the anti-angiogenic antibody-scaffold(s) or the anti-angiogenic molecule(s) diffuses from the device.

Also provided are methods of delivering an anti-angiogenic antibody-scaffold or an anti-angiogenic molecule to a recipient host by implanting any of the implantable cell culture devices described herein into a target region of the recipient host, wherein the encapsulated one or more ARPE-19 cells secrete the anti-angiogenic antibody-scaffold or the anti-angiogenic molecule at the target region. Preferred target regions can include, but are not limited to, the central nervous system, including the brain, ventricle, spinal cord, the aqueous and vitreous humors of the eye, spleen, ear, heart, colon, liver, kidney, breast, joint, bone marrow, subcutaneous, and/or peritoneal spaces. Other target regions may include, but are not limited to, whole body for systemic delivery and/or localized target sites within or near organs in the body such as breast, colon, spleen, ovary, testicle, and/or bone marrow. In such methods, the therapeutically effective amount per patient per day of the anti-angiogenic antibody-scaffold or the anti-angiogenic molecule diffuses into the target region.

Those skilled in the art will recognize that in any of the methods described herein with regard to ocular implantation and/or disorders, a therapeutically effective amount per patient per day of the anti-angiogenic antibody-scaffold or the anti-angiogenic molecule of the invention diffuses from the implantable cell culture devices. For example, between 0.1 pg and 1000 µg per patient per day of the anti-angiogenic antibody-scaffold or the anti-angiogenic molecule of the invention can diffuse from the implantable cell culture devices (e.g., into the target region(s)).

The invention also provides methods for making the implantable cell culture devices of the invention. For example, by genetically engineering at least one ARPE-19 cell to secrete one or more anti-angiogenic antibody-scaffolds or anti-angiogenic molecules (e.g., those encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 SEQ ID NO:29 and SEQ ID NO:31), and encapsulating the genetically modified ARPE-19 cells within a semipermeable membrane, wherein said membrane allows the diffusion of the anti-angiogenic antibody-scaffold or the anti-angiogenic molecule there through. In one preferred example, the anti-angiogenic molecule of the instant invention is a soluble VEGF receptor and/or a soluble PDGF receptor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 15 is a sequence alignment of p834, p873, and p917.

FIG. 16 is a sequence alignment of p834 and Aflibercept.

DETAILED DESCRIPTION OF THE INVENTION

Figure 1:
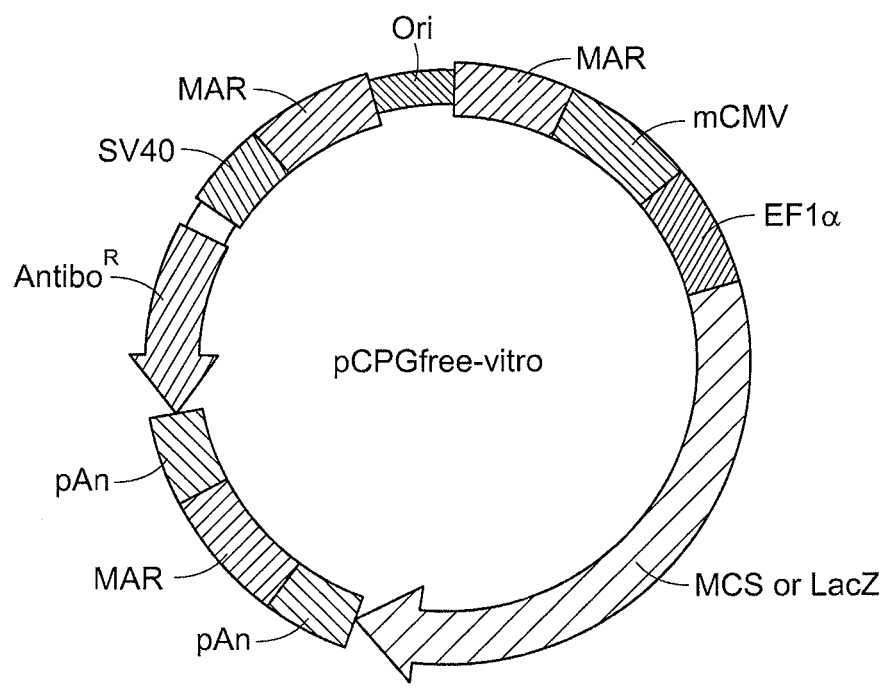
FIG. 1 is a schematic showing the pCpGfree-vitro Expression Vector (InvivoGen) Map.

Proteins are a dominant class of therapeutics used in the treatment of eye diseases. However, large antibody based protein drugs are unable to bypass the blood-retinal barrier and, thus, require repeated intraocular administration for treatment. It has previously been demonstrated encapsulated cell technology (ECT) intraocular devices can deliver a biotherapeutic directly to the eye consistently over the course of 2 years in human clinical trials, thereby suggesting this technology may be extended to other ophthalmic biologics as well, for example those related to wet AMD.

cDNA sequences representing the major classes of antibody scaffold biologics were synthesized, including, for example, full antibody, antibody Fab fragments, single chain (ScFv) antibodies, and fusion receptor-Fc molecules. cDNA expression vectors were used to create stable human cell lines secreting desired antibody-based biologics. Cell lines were subsequently encapsulated to create ocular ECT implants. The rate of protein secretion was determined by ELISA.

Cultured clonal cell lines secreted all classes of antibody scaffold proteins, many on par with CHO-cell line based manufacturing systems. Clonal cell lines exhibited robust recombinant protein secretion, with levels of some cell lines approaching 200-20,000 ng/million cells/day (20 pcd). In some embodiments, an iterative transfection process of one, two, three or more transfections can be used to genetically engineer the cells. Surprisingly, an iterative DNA transfection and selection significantly increases the ability of cell lines to produce recombinant protein secretion from 50,000 to greater than 70,000 ng/million cells/day (70 pcd). The iterative transfection process can be used to introduce multiple copies of the same or different anti-angiogenic antibody-scaffolds and/or anti-angiogenic molecules into the cells (e.g., ARPE-19 cells). Molecules produced with an iterative transfection process involving one transfection can be referred to as "first generation" molecules. Molecules produced with an iterative transfection process involving two transfections can be referred to as "second generation" molecules. Molecules produced with an iterative transfection process involving three transfections can be referred to as "third generation" molecules.

Cell lines producing active antibody scaffold based biologics and receptor fusion proteins were successfully encapsulated, and initial production of recombinant proteins from individual ECT devices were initially detected at levels up to 50-1000 ng/day. Subsequent iterative DNA transfected cell lines, in association with media optimization, increased ophthalmic ECT device levels up to 4,000 to 10,000 ng/day.

Thus, these ECT devices may be an effective drug delivery platform for large biologic molecules including antibodies, antibody scaffolds, and/or receptor fusion proteins for ophthalmic indications, as well as localized and/or systemic indications.

Vascular endothelial growth factor (VEGF) is a signaling protein involved in both vasculogenesis, the formation of the embryonic circulatory system, and angiogenesis, the growth of blood vessels from pre-existing vasculature. While VEGF is mostly known for its effects on cells of the vascular endothelium, it also affects a broad range of other cells types, e.g., stimulation monocyte/macrophage migration, neurons, cancer cells, kidney epithelial cells, etc.

There are a number of proteins within the VEGF family, which arise as a result of alternate splicing of mRNA. The various splice variants impact the function of VEGF, as they determine whether the resulting proteins are pro- or anti-angiogenic. Additionally, the splice variants also effect the interaction of VEGF with heparin sulfate proteoglycans (HSPGs) and neuripilin co-receptors on the cell surface, which, in turn, enhances the ability of VEGF to bind to and activate VEGF signaling receptors (VEGFRs).

The VEGF splice variants are released from cells as glycosylated disulfide-bonded dimers. Structurally, VEGF belongs to the PDGF family of cysteine-knot growth factors, and, thus, several closely-related proteins exist, i.e., placenta growth factor (P1GF), VEGF-B, VEGF-C and VEGF-D, which together comprise the VEGF sub-family of growth factors. VEGF itself is commonly referred to as VEGF-A in order to differentiate it from these other, related growth factors.

The VEGF family of proteins stimulates cellular response by binding to the VEGFRs or to the tyrosine kinase receptors present on a cell surface. VEGF receptors have an extracellular portion consisting of seven immunoglobulin-like domains, a single transmembrane spanning region, and an intracellular portion containing a split tyrosine-kinase domain. VEGF-A binds to both VEGFR-1 (Flt-1) and VEGFR-2 (KDR/Flk-1). VEGFR1 is expressed as a full-length receptor tyrosine kinase (RTK) as well as in a soluble form, which carries only the extracellular domain. VEGFR-2 appears to mediate almost all of the known cellular responses to VEGF and is expressed in mesodermal progenitor cells that are destined to differentiate into hemangioblasts and angioblasts. The function of VEGFR-1 is less well-defined, although it is thought to modulate VEGFR-2 signaling. VEGF-C and VEGF-D, but not VEGF-A, are also ligands for a third receptor (VEGFR-3), which mediates lymphangiogenesis.

Platelet Derived Growth Factor (PDGF) is a growth factor that also plays a role in angiogenesis. Multiple forms of PDGF exists, composed dimers containing two A chains (AA), two B chains (BB), or a mixed A/B chain (AB). PDGF is a potent mitogen for pericytes, a class of cells that serve as support for endothelial cell growth. PDGF receptor (PDGFR) exists in two forms, alpha and beta. PDGFR beta has the highest affinity for PDGF-BB and has been shown to exert anti-angiogenic biological effect as a secreted protein in either fusion protein—Fc form or as an extracellular soluble receptor. Recently, potent synergistic anti-angiogenic activity has been demonstrated in mouse ocular vascular neogenesis models involving the combination of anti-VEGF molecules and antagonistic PDGF molecules. Thus a combination anti-PDGF, anti-VEGF therapy may exert a higher anti-angiogenic activity than anti-VEGF therapy alone.

A gene of interest (i.e., a gene that encodes a given anti-angiogenic antibody-scaffold or an anti-angiogenic molecule, such as VEGF receptor or PDGF receptor construct according to the invention) can be inserted into a cloning site of a suitable expression vector using standard techniques known in the art. The nucleic acid and amino acid sequences of the human (and other mammalian) genes encoding VEGF receptor molecules are known. See, e.g., U.S. Pat. Nos. 4,997,929; 5,141,856; 5,364,769; 5,453,361; WO 93/06116; WO 95/30686, incorporated herein by reference.

Various specific truncated VEGF receptor and/or PDGF receptor constructs are contemplated by the instant invention. Also contemplated are anti-angiogenic antibody-scaffolds (i.e., antibodies and antigen-binding fragments and derivatives thereof, single chain antibodies, etc.) that disrupt the binding of VEGF to its receptors or PDGF to its receptors. For example, the soluble VEGFR receptor proteins described herein comprise fragments of secretory VEGF receptor 1 (sVR1), secretory VEGF receptor 2 (sVR2), and/or a chimera of VEGF binding domains of VEGF receptor 1 and secretory VEGF receptor 2. These secretory proteins bind VEGF and contain multiple Ig-like domains. Several immunoglobulin-like domains from both VR1 and VR2 are used in the soluble VEGF receptor constructs disclosed herein. Those skilled in the art will recognize that domain 2 (D2) is the VEGF-binding domain ("VBD") of sVR1, but it requires domain 3 (D3) for high affinity binding of VEGF. Truncations of sVR1 containing domains 1 through 3 (D1-3) or domains 2-3 (D-3) bind VEGF with higher affinity than domain 2 alone. Moreover, these truncations also neutralize the angiogenic effects of VEGF. VR2 has similar requirements for high affinity VEGF-binding but additionally must be dimeric, since the monomeric version binds with very low affinity. The various receptor constructs described herein include domains 1, 2, and 3 of VR2 and a chimera of domain 2 of VR1 and domain 3 of VR2. Versions may be monomeric or dimeric in form. The dimerizing component of the soluble VEGF receptor constructs described herein is the full length Fc region.

In another example, PDGFR beta extracellular domains 1-5 have been shown to bind PDGF. Truncation of PDGFR beta extracellular domains to 1-3 also binds PDGF. Thus combinations of these soluble native extracellular domains, or as fusion proteins will allow the creation of a soluble antagonist to PDGF. The use of PDGFR beta antagonists may supplement the anti-angiogenic effects of VEGF antagonists as shown in multiple models of ocular neovascularization. (Jo et al. 2006).

The invention also provides anti-angiogenic antibody-scaffolds and receptor fusion proteins that are derived from (and/or are biosimilar to) known anti-VEGF compounds and bioreactive fragments thereof. For example, the known anti-VEGF compounds include, but are not limited to, anti-VEGF receptor fragments (i.e., Aflibercept) and/or anti-VEGF antibodies (or antigen binding fragments thereof) (i.e., Bevacizumab, DrugBank DB00112; or Ranibizumab DrugBank DB01270)). The sequences of these known anti-VEGF compounds are known in the art. In other examples, bioactive antagonistic PDGF receptor fragments have also been described in the literature (Heidaran et al., 1990; Heidaran et al., 1995; Nakamura et al. 2001)

The specific anti-angiogenic antibody-scaffolds and VEGF receptor constructs of the invention include:
1) p834 (VEGFR-Fc#1, [RS-VEGF Receptor 1, Domain 2 and VEGF Receptor 2, Domain 3 (R1D2-R2D3)]-EFEPKSC-hIgG1 Fc)
2) p838 (VEGFR-Fc#2, [VEGF Receptor 2, Domains 1, 2, and 3 (R2D1-R2D2-R2D3)])
3) p876 (VEGF antibody ScFv#1, with His-tag)
4) p913 (VEGF antibody ScFv#2, without His-tag)
5) p873 (Aflibercept, VEGFR-Fc#3, VEGF Receptor 1, Domain 2 and VEGF Receptor 2, Domain 3 (R1D2-R2D3) hIgG1 Fc)
6) p874/p875 (Bevacizumab, VEGF full antibody #1, heavy chain/light chain)
7) p915/p914 (Ranibizumab, VEGF antibody Fab, heavy chain fragment/light chain)
8) p916/p914 (Ranibizumab, VEGF full antibody #2, heavy chain/light chain)
9) p917 (VEGFR-Fc#1, [RS-VEGF Receptor 1, Domain 2 and VEGF Receptor 2, Domain 3 (R1D2-R2D3)]-hIgG1 Fc)

The VEGF constructs described for the first time herein are superior to those VEGF receptor constructs described in WO 09/149,205. Specifically, VEGF receptor constructs lacking the Fc tail (See, e.g., SEQ ID NO: 12 of WO 09/149,205) were either highly inflammatory in animal models or could not be made into stable cell lines. Each of the constructs in the WO09/149,205 application included the IgG hinge region but not the Fc tail. As a result, these constructs are all F(ab)-2-like molecules. Those skilled in the art will recognize that F(ab)'2 proteins have been reported to show immunogenicity. (See Fumia et al., Molecular Immunology 45:2951-61 (2008); Lutz et al., Autoinflammatory Reviews 7:508-13 (2008), each of which is herein incorporated by reference in its entirety).

One surprising discovery of the instant invention is that VEGF receptor constructs containing the IgG hinge region plus the Fc tail, such as, for example construct p834 (SEQ ID NO: 1), produced far less immunological response in rabbits and none in clinical settings.

Three of the constructs described herein, p834 (VEGF-Fc), p873 (Aflibercept), and p917 (Aflibercept RS) have slightly different amino acid sequences. For example, the differences between p834 and p873 include the following:
a. 834 contains RS amino acid between signal peptide and mature protein
b. 834 contains EFEPKSC at hinge
c. 834 contains terminal K (natural)
d. 873 contains 5' attB1 and 3' attB2 recomb sites (not translated)

Figure 14:
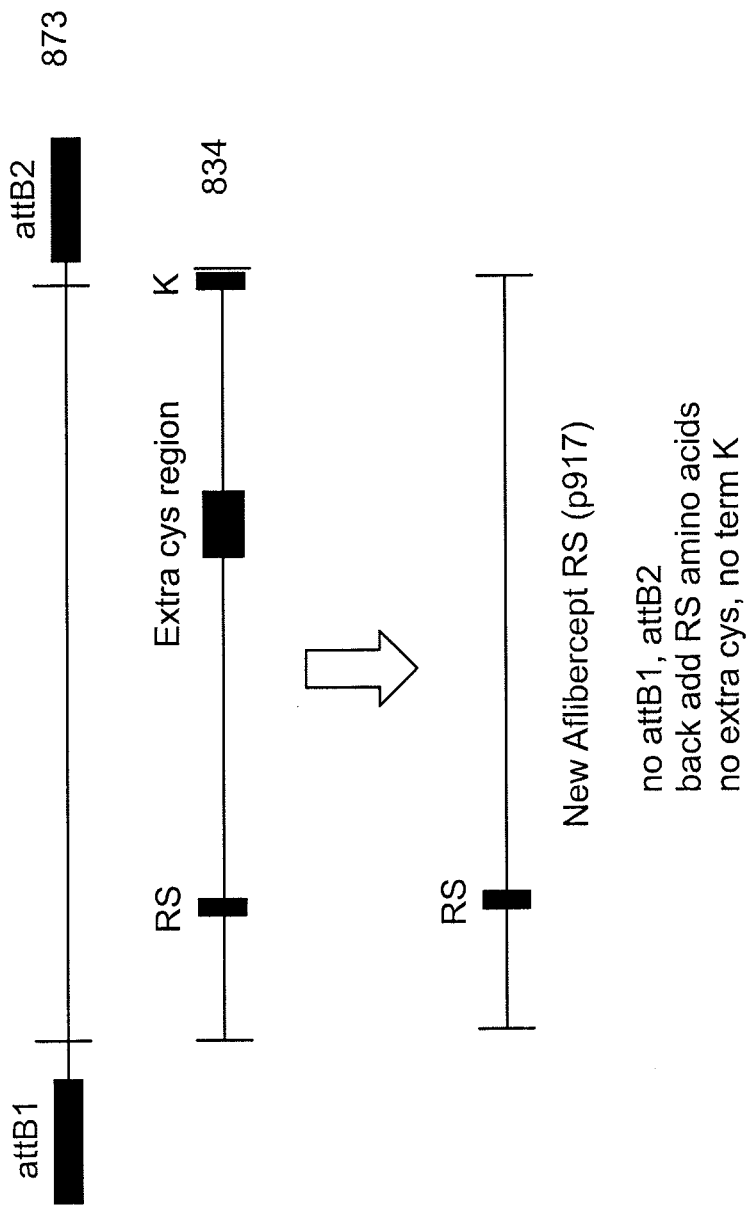
FIG. 14 is a schematic showing the relative structures of p834, p873, and p917.

In addition, a new Aflibercept RS molecule (p917) was created that based on p873 but removes attB1 and attB2 and adds back in RS amino acid between signal peptide and mature protein. These sequences differences are schematically illustrated in FIG. 14, and a sequence alignment is shown in FIG. 15. A sequence alignment of p834 and Aflibercept is shown in FIG. 16.

Surprisingly, p834 unexpectedly outperformed (i.e., produced more of the anti-angiogenic antibody-scaffold) both the p873 and p917 constructs.

Thus, p834 is both structurally different from and exhibits surprising and unexpected advantages over other constructs known in the art (i.e., p873) and constructs that were generated based on these known constructs (i.e., p917).

Cell lines were generated based on the 834, 873, and 917 and anti-angiogenic antibody-scaffold output was measured. The results are summarized below.

| Derived Cell Lines | PCD | Comment |
|---|---|---|
| 834-10-5 | ~15 PCD | Became the basis for second and third generation ECT devices |
| 873 (true Aflibercept biosimilar) | ~2 PCD | Could not get high expression cell line using standard techniques |
| 917 ("Aflibercept RS" (half-way between true Aflibercept and 834) | NONE | Unstable. Unable to generate cell line |

Transfecting p834 (also p910, p969) results in the generation of high expressing clones each time. Thus, there is apparently some advantage about p834 that is absent from 873 or 917—potentially being a longer hinge with extra cysteine conferring additional molecule stability.

The specific anti-angiogenic PDGF receptor constructs of the invention include:

10) p964 (PDGFR-Beta domains 1-5 receptor-IgG4 Fc fusion)

11) p963 (PDGFR-Beta domains 1-5 receptor-IgG1 Fc fusion)

12) p974 (PDGFR-Beta domains 1-3 receptor-IgG1 Fc fusion)

13) p978 (PDGFR-Beta domains 1-5 receptor)

14) p977 (PDGFR-Beta domains 1-5 receptor plus His6 tag)

The specific nucleotide and amino acid sequences of each of these constructs are shown below.

For the purpose of clarity, the constructs, cell lines and anti-angiogenic antibody-scaffolds and/or anti-angiogenic molecules of the instant invention are identified as follows in the instant application: "pXXX" refers to a plasmid (for example, plasmid p834), "XXX-X-XX" refers to a cell line (for example, cell line 834-10-5), and "XXX" refers to a molecule (for example, molecule 834). However, those skilled in the art will recognize that any of the scaffolds and constructs and cell lines based on the invention may be referred to, identified, and/or demarcated interchangeably herein.

In some embodiments, the same molecule can be introduced into different expression vectors, thereby making different plasmids. For example, molecule 834 cDNA can be introduced into pCpG vitro free blasticidin resistant vector to make plasmid p834 cDNA. Alternatively, molecule 834 can also be introduced into pCpG vitro free neomycin resistant vector to make plasmid p910; or into pCpG hygromycin resistant vector to make plasmid p969 (See, Example 7).

Using the iterative transfection process described herein, multiple copies of the same (or different) anti-angiogenic antibody-scaffolds and/or anti-angiogenic molecules can be incorporated into a cell (e.g., an ARPE-19 cell). For example, when the iterative transfection process introduces two transfections, a second generation construct (910) is generated, which contains two copies of the 834 cDNA. Similarly, when the iterative transfection process introduces three transfections, a third generation construct (969) is generated, which contains three copies of the 834 cDNA.

Figure 17:
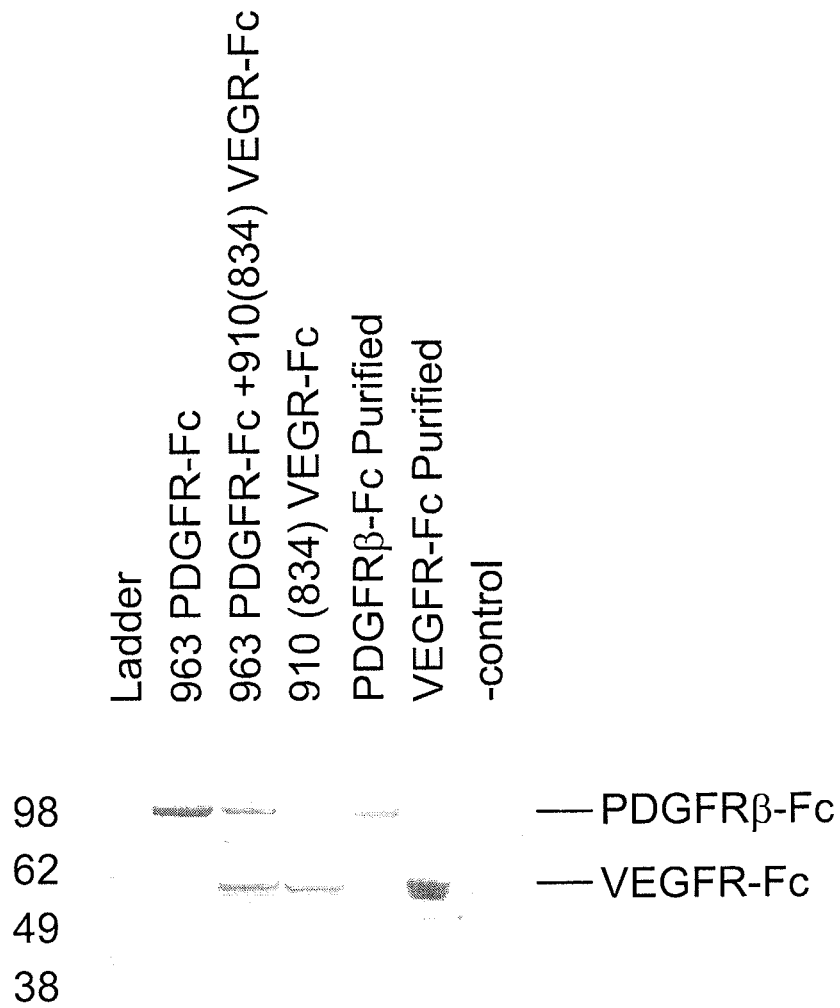
FIG. 17 is a Western blot showing anti-PDGFR plus anti-Fc detection of PDGFR-Fc and VEGFR-Fc secreted from a combined-loading device.

As shown in FIG. 17, 963 PDGFR-Fc cell line and 910 (834) second generation VEGFR-Fc cell lines were encapsulated either as single cell lines or as a mixture of cell lines ("combined-load") in a single ECT device. Western blot analysis of device condition media after 2 hour culture reveals that the combined-loaded devices secrete both the 963 PDGFR-Fc and 910(834) VEGFR-Fc proteins simultaneously.

p834

(SEQ ID NO: 1)

```
atggtcagctactgggacaccggggtcctgctgtgcgcgctgctcagctgtctgcttctcacaggatcta gttcaggttcgcgaagtgatacaggtagacctttcgtagagatgtacagtgaaatccccgaaattataca catgactgaaggaagggagctcgtcattccctgccgggttacgtcacctaacatcactgttactttaaaa aagtttccacttgacactttgatccctgatggaaaacgcataatctgggacagtagaaagggcttcatca tatcaaatgcaacgtacaaagaaatagggcttctgacctgtgaagcaacagtcaatgggcatttgtataa gacaaactatctcacacatcgacaaaccaatacaatcatcgatgtggttctgagtccgtctcatggaatt gaactatctgttggagaaaagcttgtcttaaattgtacagcaagaactgaactaaatgtggggattgact tcaactgggaatacccttcttcgaagcatcagcataagaaacttgtaaaccgagacctaaaaacccagtc tgggagtgagatgaagaaattttttgagcaccttaactatagatggtgtaacccggagtgaccaaggattg tacacctgtgcagcatccagtgggctgatgaccaagaagaacagcacatttgtcagggtccatgaaaaag aattcgagcccaaatcttgtgacaaaactcacacatgcccaccgtgcccagcacctgaactcctgggggg accgtcagtcttcctcttccccccaaaacccaaggacaccctcatgatctcccggacccctgaggtcaca tgcgtggtggtggacgtgagccacgaagaccctgaggtcaagttcaactggtacgtggacggcgtggagg tgcataatgccaagacaaagccgcgggaggagcagtacaacagcacgtaccgtgtggtcagcgtcctcac cgtcctgcaccaggactggctgaatggcaaggagtacaagtgcaaggtctccaacaaagccctcccagcc cccatcgagaaaaccatctccaaagccaaagggcagccccgagaaccacaggtgtacaccctgcccccat cccgggatgagctgaccaagaaccaggtcagcctgacctgcctggtcaaaggcttctatcccagcgacat cgccgtggagtgggagagcaatgggcagccggagaacaactacaagaccacgcctcccgtgctggactcc
```

-continued gacggctccttcttcctctacagcaagctcaccgtggacaagagcaggtggcagcaggggaacgtcttct catgctccgtgatgcatgaggctctgcacaaccactacacgcagaagagcctctccctgtctccgggtaa a (SEQ ID NO: 2)
mvsywdtgvllcallsclllltgsssgsrsdtgrpfvemyseipeiihmtegrelvipcrvtspnitvtlk kfpldtlipdgkriiwdsrkgfiisnatykeiglltceatvnghlyktnylthrqtntiidvvlspshgi elsvgeklvinctartelnvgidfnweypsskhqhkklvnrdlktqsgsemkkflstltidgvtrsdqgl ytcaassglmtkknstfvrvhekefepkscdkthtcppcpapellggpsvflfppkpkdtlmisrtpevt cvvvdvshedpevkfnwyvdgvevhnaktkpreeqynstyrvvsvltvlhqdwlngkeykckvsnkalpa piektiskakgqprepqvytlppsrdeltknqvsltclvkgfypsdiavewesngqpennykttppvlds dgsfflyskltvdksrwqqgnvfscsvmhealhnhytqkslslspgk p838

(SEQ ID NO: 3)
atggagagcaaggtgctgctggccgtcgccctgtggctctgcgtggagacccgggccgcctctgtgggtt tgcctagtgtttctcttgatctgcccaggctcagcatacaaaaagacatacttacaattaaggctaatac aactcttcaaattacttgcaggggacagagggacttggactggctttggcccaataatcagagtggcagt gagcaaagggtggaggtgactgagtgcagcgatggcctcttctgtaagacactcacaattccaaaagtga tcggaaatgacactggagcctacaagtgcttctaccgggaaactgacttggcctcggtcatttatgtcta tgttcaagattacagatctccatttattgcttctgttagtgaccaacatggagtcgtgtacattactgag aacaaaaacaaaactgtggtgattccatgtctcgggtccatttcaaatctcaacgtgtcactttgtgcaa gatacccagaaaagagatttgttcctgatggtaacagaatttcctgggacagcaagaagggctttactat tcccagctacatgatcagctatgctggcatggtcttctgtgaagcaaaaattaatgatgaaagttaccag tctattatgtacatagttgtcgttgtagggtataggatttatgatgtggttctgagtccgtctcatggaa ttgaactatctgttggagaaaagcttgtcttaaattgtacagcaagaactgaactaaatgtggggattga cttcaactgggaataccccttcttcgaagcatcagcataagaaacttgtaaaccgagacctaaaaacccag tctgggagtgagatgaagaaattttttgagcaccttaactatagatggtgtaacccggagtgaccaaggat tgtacacctgtgcagcatccagtgggctgatgaccaagaagaacagcacatttgtcagggtccatgaaaa acctttgttgcttttggaagtggcgaattcgagcccaaatcttgtgacaaaactcacacatgcccaccg tgcccagcacctgaactcctgggggaccgtcagtcttcctcttccccccaaaacccaaggacaccctca tgatctcccggacccctgaggtcacatgcgtggtggtggacgtgagccacgaagaccctgaggtcaagtt caactggtacgtggacggcgtggaggtgcataatgccaagacaaagccgcgggaggagcagtacaacagc acgtaccgtgtggtcagcgtcctcaccgtcctgcaccaggactggctgaatggcaaggagtacaagtgca aggtctccaacaaagccctcccagcccccatcgagaaaaccatctccaaagccaaagggcagccccgaga accacaggtgtacaccctgcccccatcccgggatgagctgaccaagaaccaggtcagcctgacctgcctg gtcaaaggcttctatcccagcgacatcgccgtggagtgggagagcaatgggcagccggagaacaactaca agaccacgcctcccgtgctggactccgacggctccttcttcctctacagcaagctcaccgtggacaagag caggtggcagcaggggaacgtcttctcatgctccgtgatgcatgaggctctgcacaaccactacacgcag aagagcctctccctgtctccgggtaaa (SEQ ID NO: 4)
meskvllavalwlcvetraasvglpsysldlprlsiqkdiltikanttlqitcrgqrdldwlwpnnqsgs eqrvevtecsdglfcktltipkvigndtgaykcfyretdlasviyvyvqdyrspfiasysdqhgvvyite nknktvvipclgsisnlnvslcarypekrfvpdgnriswdskkgftipsymisyagmvfceakindesyq simyivvvvgyriydvvlspshgielsvgeklvlnctartelnvgidfnweypsskhqhkklvnrdlktq -continued sgsemkkflstltidgvtrsdqglytcaassglmtkknstfvrvhekpfvafgsgefepkscdkthtcpp
cpapellggpsvflfppkpkdtlmisrtpevtcvvvdvshedpevkfnwyvdgvevhnaktkpreeqyns
tyrvvsvltvlhqdwlngkeykckvsnkalpapiektiskakgqprepqvytlppsrdeltknqvsltcl
vkgfypsdiavewesngqpennykttppvldsdgsfflyskltvdksrwqqgnvfscsvmhealhnhytq
kslslspgk p876

(SEQ ID NO: 5)
atggacatgcgggtgccagctcagctgctgggactgctgctgctgtggctgcccggcaccagatgcgaca
tccagctgacccagtccccctccagcctgtccgcctctgtgggcgacagagtgaccatcacctgttccgc
ctcccaggacatcagcaactacctgaactggtatcagcagaagcccggcaaggcccccaaggtgctgatc
tacttcaccagcagcctgcactccggcgtgccctcccggttctccggctccggctccggcaccgacttca
ccctgaccatctccagcctgcagcccgaggacttcgccacctactactgccagcagtacagcaccgtgcc
ctggaccttcggccagggcaccaaggtggaaatcaagggaggtggaggaagcggtggaggaggtagcgga
ggcggcggcagcgaggtgcagctggtggaatccggcggaggactggtgcagcctggcggctccctgagac
tgtcttgcgccgcctccggctacgacttcacccactacggcatgaactgggtccgacaggcccctggcaa
gggactggaatgggtgggctggatcaacacctacaccggcgagcccacctacgccgccgacttcaagcgg
cggttcaccttcagcctggacaccagcaagagcaccgcctacctgcagatgaactccctgcgggccgagg
acaccgccgtgtactactgcgccaagtaccccactactacggcaccagccactggtacttcgacgtgtg
gggccagggcaccctggtcaccgtctcctcacaccatcaccaccaccac (SEQ ID NO: 6)
mdmrvpaqllglllllwlpgtrcdiqltqspsslsasvgdrvtitcsasqdisnylnwYqqkpgkapkvli
yftsslhsgvpsrfsgsgsgtdftltisslqpedfatyycqqystvpwtfgqgtkveikggggsggggsg
gggsevqlvesgggIvqpggsIrIscaasgydfthygmnwvrqapgkglewvgwintytgeptYaadfkr
rftfsldtskstaylqmnslraedtavyycakypyyygtshwyfdvwgqgtlvtvsshhhhhh p913

(SEQ ID NO: 19)
atggacatgcgggtgccagctcagctgctgggactgctgctgctgtggctgcccggcaccagatgcgaca
tccagctgacccagtccccctccagcctgtccgcctctgtgggcgacagagtgaccatcacctgttccgc
ctcccaggacatcagcaactacctgaactggtatcagcagaagcccggcaaggcccccaaggtgctgatc
tacttcaccagcagcctgcactccggcgtgccctcccggttctccggctccggctccggcaccgacttca
ccctgaccatctccagcctgcagcccgaggacttcgccacctactactgccagcagtacagcaccgtgcc
ctggaccttcggccagggcaccaaggtggaaatcaagggaggtggaggaagcggtggaggaggtagcgga
ggcggcggcagcgaggtgcagctggtggaatccggcggaggactggtgcagcctggcggctccctgagac
tgtcttgcgccgcctccggctacgacttcacccactacggcatgaactgggtccgacaggcccctggcaa
gggactggaatgggtgggctggatcaacacctacaccggcgagcccacctacgccgccgacttcaagcgg
cggttcaccttcagcctggacaccagcaagagcaccgcctacctgcagatgaactccctgcgggccgagg
acaccgccgtgtactactgcgccaagtaccccactactacggcaccagccactggtacttcgacgtgtg
gggccagggcaccctggtcaccgtctcctca (SEQ ID NO: 20)
mdmrvpaqllglllllwlpgtrcdiqltqspsslsasvgdrvtitcsasqdisnylnwyqqkpgkapkvli
yftsslhsgvpsrfsgsgsgtdftltisslqpedfatyycqqystvpwtfgqgtkveikggggsggggsg
gggsevqlvesgggIvqpggsIrIscaasgydfthygmnwvrqapgkglewvgwintYtgeptYaadfkr
rftfsldtskstaylqmnslraedtavyycakypyyygtshwyfdvwgqgtlvtvss -continued p873

(SEQ ID NO: 7)
atggtcagctactgggacaccggggtcctgctgtgcgcgctgctcagctgtctgcttctcacaggatcta gttcaggtagtgatacaggtagacctttcgtagagatgtacagtgaaatccccgaaattatacacatgac tgaaggaagggagctcgtcattccctgccgggttacgtcacctaacatcactgttactttaaaaaagttt ccacttgacactttgatccctgatggaaaacgcataatctgggacagtagaaagggcttcatcatatcaa atgcaacgtacaaagaaatagggcttctgacctgtgaagcaacagtcaatgggcatttgtataagacaaa ctatctcacacatcgacaaaccaatacaatcatcgatgtggttctgagtccgtctcatggaattgaacta tctgttggagaaaagcttgtcttaaattgtacagcaagaactgaactaaatgtggggattgacttcaact gggaataccctt cttcgaagcatcagcataagaaacttgtaaaccgagacctaaaaacccagtctgggag tgagatgaagaaattttttgagcaccttaactatagatggtgtaacccggagtgaccaaggattgtacacc tgtgcagcatccagtgggctgatgaccaagaagaacagcacatttgtcagggtccatgaaaaagacaaaa ctcacacatgcccaccgtgcccagcacctgaactcctggggggaccgtcagtcttcctcttccccccaaa acccaaggacacc ctcatgatctcccggacccctgaggtcacatgcgtggtggtggacgtgagccacgaa gaccctgaggtcaagttcaactggtacgtggacggcgtggaggtgcataatgccaagacaaagccgcggg aggagcagtacaacagcacgtaccgtgtggtcagcgtcctcaccgtcctgcaccaggactggctgaatgg caaggagtacaagtgcaaggtctccaacaaagcccctcccagcccccatcgagaaaaccatctccaaagcc aaagggcagccccgagaaccacaggtgtacaccctgcccccatcccgggatgagctgaccaagaaccagg tcagcctgacctgcctggtcaaaggcttctatcccagcgacatcgccgtggagtgggagagcaatgggca gccggagaacaactacaagaccacgcctcccgtgctggactccgacggctccttcttcctctacagcaag ctcaccgtggacaagagcaggtggcagcaggggaacgtcttctcatgctccgtgatgcatgaggctctgc acaaccactacacgcagaagagcctctccctgtctccgggt (SEQ ID NO: 8)
mvsywdtgvllcallsclllt gsssgsdtgrpfvemyseipeiihmtegrelvipcrvtspnitvtlkkf pldtlipdgkriiwdsrkgfiisnatykeiglltceatvnghlyktnylthrqtntiidvvlspshgiel svgeklvinctartelnvgidfnweypsskhqhkklvnrdlktqsgsemkkflstltidgvtrsdqglyt caassglmtkknstfvrvhekdkthtcppcpapellggpsvflfppkpkdtlmisrtpevtcvvvdvshe dpevkfnwyvdgvevhnaktkpreeqynstyrvvsvltvlhqdwlngkeykckvsnkalpapiektiska kgqprepqvytlppsrdeltknqvsltclvkgfypsdiavewesngqpennykttppvldsdgsfflysk ltvdksrwqqgnvfscsvmhealhnhytqkslslspg p874

(SEQ ID NO: 9)
atggactggacctggtctatcctgttcctggtggccgctgcaaccggcacctactccgaggtgcagctgg tggaatccggcggaggactggtgcagcctggcggctccctgagactgtcttgcgccgcctccggctacac cttcaccaactacggcatgaactgggtccgacaggcccctggcaagggactggaatgggtgggctggatc aacacctacaccggcgagcccacctacgccgccgacttcaagcggcggttcaccttcagcctggacacca gcaagagcaccgcctacctgcagatgaactccctgcgggccgaggacaccgccgtgtactactgcgccaa gtaccccactactacggcagcagccactggtacttcgacgtgtggggccagggcaccctggtcaccgtc tcctcagcctccaccaagggcccatcggtcttccccctggcaccctcctccaagagcacctctgggggca cagcggccctgggctgcctggtcaaggactacttccccgaaccggtgacggtgtcgtggaactcaggcgc cctgaccagcggcgtgcacaccttcccggctgtcctacagtcctcaggactctactccctcagcagcgtg gtgaccgtgccctccagcagcttgggcacccagacctacatctgcaacgtgaatcacaagcccagcaaca ccaaggtggacaagaaagttgagcccaaatcttgtgacaaaactcacacatgcccaccgtgcccagcacc -continued tgaactcctggggggaccgtcagtcttcctcttcccccaaaacccaaggacaccctcatgatctcccgg acccctgaggtcacatgcgtggtggtggacgtgagccacgaagaccctgaggtcaagttcaactggtacg tggacggcgtggaggtgcataatgccaagacaaagccgcgggaggagcagtacaacagcacgtaccgtgt ggtcagcgtcctcaccgtcctgcaccaggactggctgaatggcaaggagtacaagtgcaaggtctccaac aaagcccccagcccccatcgagaaaaccatctccaaagccaaagggcagccccgagaaccacaggtgt acaccctgcccccatcccgggatgagctgaccaagaaccaggtcagcctgacctgcctggtcaaaggctt ctatcccagcgacatcgccgtggagtgggagagcaatgggcagccggagaacaactacaagaccacgcct cccgtgctggactccgacggctccttcttcctctacagcaagctcaccgtggacaagagcaggtggcagc aggggaacgtcttctcatgctccgtgatgcatgaggctctgcacaaccactacacgcagaagagcctctc cctgtctccgggtaaa (SEQ ID NO: 10)
mdwtwsilflvaaatgtysevqlvesggglvqpggslrlscaasgytftnygmnwvrqapgkglewvgwi ntytgeptyaadfkrrftfsldtskstaylqmnslraedtavyycakyphyygsshwyfdvwgqgtivtv ssastkgpsvfplapsskstsggtaalgclvkdyfpepvtvswnsgaltsgvhtfpavlqssglyslssv vtvpssslgtqtyicnvnhkpsntkvdkkvepkscdkthtcppcpapellggpsvflfppkpkdtlmisr tpevtcvvvdvshedpevkfnwyvdgvevhnaktkpreeqynstyrvvsvltvlhqdwlngkeykckvsn kalpapiektiskakgqprepqvytlppsrdeltknqvsltclvkgfypsdiavewesngqpennYkttp pvldsdgsfflyskltvdksrwqqgnvfscsvmhealhnhytqkslslspgk p875

(SEQ ID NO: 11)
atggacatgcgggtgccagctcagctgctgggactgctgctgctgtggctgcccggcaccagatgcgaca tccagatgacccagtcccctccagcctgtccgcctctgtgggcgacagagtgaccatcacctgttccgc ctcccaggacatcagcaactacctgaactggtatcagcagaagcccggcaaggcccccaaggtgctgatc tacttcaccagcagcctgcactccggcgtgccctcccggttctccggctccggcaccgacttca ccctgaccatctccagcctgcagcccgaggacttcgccacctactactgccagcagtacagcaccgtgcc ctggaccttcggccagggcaccaaggtggaaatcaagcggaccgtggccgctcccctccgtgttcatcttc ccaccctccgacgagcagctgaagtccggcaccgcctccgtcgtctgcctgctgaacaacttctacccc gcgaggccaaggtgcagtggaaggtggacaacgccctgcagtccggcaactcccaggaatccgtcaccga gcaggactccaaggacagcacctactccctgtcctccaccctgaccctgtccaaggccgactacgagaag cacaaggtgtacgcctgcgaagtgacccaccagggcctgtccagccccgtgaccaagtccttcaaccggg gcgagtgc (SEQ ID NO: 12)
mdmrvpaqllglllllwlpgtrcdiqmtqspsslsasvgdrvtitcsasqdisnylnwyqqkpgkapkvli yftsslhsgvpsrfsgsgsgtdftltisslqpedfatyycqqystvpwtfgqgtkveikrtvaapsvfif ppsdeqlksgtasvvcllnnfypreakvqwkvdnalqsgnsqesvteqdskdstYslsstltlskadyek hkvyacevthqglsspvtksfnrgec p915

(SEQ ID NO: 13)
atggactggacctggtctatcctgttcctggtggccgctgcaaccggcacctactccgaggtgcagctgg tggaatccggcggaggactggtgcagcctggcggctccctgagactgtcttgcgccgcctccggctacga cttcacccactacggcatgaactgggtccgacaggcccctggcaagggactggaatgggtgggctggatc aacacctacaccggcgagcccacctacgccgccgacttcaagcggcggttcaccttcagcctggacacca gcaagagcaccgcctacctgcagatgaactccctgcgggccgaggacaccgccgtgtactactgcgccaa gtaccccctactactacggcaccagccactggtacttcgacgtgtggggccagggcaccctggtcaccgtc -continued

```
tcctcagcctccaccaagggcccatcggtcttccccctggcaccctcctccaagagcacctctgggggca cagcggccctgggctgcctggtcaaggactacttccccgaaccggtgacggtgtcgtggaactcaggcgc cctgaccagcggcgtgcacaccttcccggctgtcctacagtcctcaggactctactccctcagcagcgtg gtgaccgtgccctccagcagcttgggcacccagacctacatctgcaacgtgaatcacaagcccagcaaca ccaaggtggacaagaaagttgagcccaaatcttgtgacaaaactcacctg
```

(SEQ ID NO: 14)
```
mdwtwsilflvaaatgtysevqlvesggglvqpggslrlscaasgydfthygmnwvrqapgkglewvgwi ntytgeptyaadfkrrftfsldtskstaylqmnslraedtavyycakypYyygtshwyfdvwgqgtivtv ssastkgpsvfplapsskstsggtaalgclvkdyfpepvtvswnsgaltsgvhtfpavlqssglyslssv vtvpssslgtqtyicnvnhkpsntkvdkkvepkscdkthl
``` p914

(SEQ ID NO: 15)
```
atggacatgcgggtgccagctcagctgctgggactgctgctgctgtggctgcccggcaccagatgcgaca tccagctgacccagtccccctccagcctgtccgcctctgtgggcgacagagtgaccatcacctgttccgc ctcccaggacatcagcaactacctgaactggtatcagcagaagcccggcaaggccccaaggtgctgatc tacttcaccagcagcctgcactccggcgtgccctcccggttctccggctccggctccggcaccgacttca ccctgaccatctccagcctgcagcccgaggacttcgccacctactactgccagcagtacagcaccgtgcc ctggaccttcggccagggcaccaaggtggaaatcaagcggaccgtggccgctcccctccgtgttcatcttc ccaccctccgacgagcagctgaagtccggcaccgcctccgtcgtctgcctgctgaacaacttctaccccc gcgaggccaaggtgcagtggaaggtggacaacgccctgcagtccggcaactcccaggaatccgtcaccga gcaggactccaaggacagcacctactccctgtcctccaccctgaccctgtccaaggccgactacgagaag cacaaggtgtacgcctgcgaagtgacccaccagggcctgtccagcccgtgaccaagtccttcaaccggg gcgagtgc
```

(SEQ ID NO: 16)
```
mdmrvpaqllglllllwlpgtredrediqltqspsslsasvgdrvtitcsasqdisnylnwyqqkpgkapkvli yftsslhsgvpsrfsgsgsgtdftltisslqpedfatyycqqystvpwtfgqgtkveikrtvaapsvfif ppsdeqlksgtasvvcllnnfypreakvqwkvdnalqsgnsqesvteqdskdstyslsstltlskadyek hkvyacevthqglsspvtksfnrgec
``` p916

(SEQ ID NO: 17)
```
atggactggacctggtctatcctgttcctggtggccgctgcaaccggcacctactccgaggtgcagctgg tggaatccggcggaggactggtgcagcctggcggctccctgagactgtcttgcgccgcctccggctacga cttcacccactacggcatgaactgggtccgacaggcccctggcaagggactggaatgggtgggctggatc aacacctacaccggcgagcccacctacgccgccgacttcaagcggcggttcaccttcagcctggacacca gcaagagcaccgcctacctgcagatgaactccctgcgggccgaggacaccgccgtgtactactgcgccaa gtacccctactactacggcaccagccactggtacttcgacgtgtggggccagggcaccctggtcaccgtc tcctcagcctccaccaagggcccatcggtcttccccctggcaccctcctccaagagcacctctgggggca cagcggccctgggctgcctggtcaaggactacttccccgaaccggtgacggtgtcgtggaactcaggcgc cctgaccagcggcgtgcacaccttcccggctgtcctacagtcctcaggactctactccctcagcagcgtg gtgaccgtgccctccagcagcttgggcacccagacctacatctgcaacgtgaatcacaagcccagcaaca ccaaggtggacaagaaagttgagcccaaatcttgtgacaaaactcacacatgcccaccgtgcccagcacc tgaactcctggggggaccgtcagtcttcctcttccccccaaaacccaaggacaccctcatgatctcccgg acccctgaggtcacatgcgtggtggtggacgtgagccacgaagaccctgaggtcaagttcaactggtacg
```

-continued tggacggcgtggaggtgcataatgccaagacaaagccgcggggaggagcagtacaacagcacgtaccgtgt ggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgt acaccctgcccccatcccgggatgagctgaccaagaaccaggtcagcctgacctgcctggtcaaaggctt ctatcccagcgacatcgccgtggagtgggagagcaatgggcagccggagaacaactacaagaccacgcct cccgtgctggactccgacggctccttcttcctctacagcaagctcaccgtggacaagagcaggtggcagc aggggaacgtcttctcatgctccgtgatgcatgaggctctgcacaaccactacacgcagaagagcctctc cctgtctccgggtaaa (SEQ ID NO: 18)
mdwtwsilflvaaatgtysevqlvesggglvqpggslrlscaasgydfthygmnwvrqapgkglewvgwi ntytgeptyaadfkrrftfsldtskstaylqmnslraedtavyycakypyyygtshwyfdvwgqgtlvtv ssastkgpsvfplapsskstsggtaalgclvkdyfpepvtvswnsgaltsgvhtfpavlqssglyslssv vtvpssslgtqtyicnvnhkpsntkvdkkvepkscdkthtcppcpapellggpsvflfppkpkdtlmisr tpevtcvvvdvshedpevkfnwyvdgvevhnaktkpreeqynstyrvvsvltvlhqdwlngkeykckvsn kalpapiektiskakgqprepqvytlppsrdeltknqvsltclvkgfypsdiavewesngqpennykttp pvldsdgsfflyskltvdksrwqqgnvfscsvmhealhnhytqkslslspgk p917

(SEQ ID NO: 21)
atggtcagctactgggacaccggggtcctgctgtgcgcgctgctcagctgtctgcttctcacaggatcta gttcaggttcgcgaagtgatacaggtagacctttcgtagagatgtacagtgaaatccccgaaattataca catgactgaaggaagggagctcgtcattccctgccgggttacgtcacctaacatcactgttactttaaaa aagtttccacttgacactttgatccctgatggaaaacgcataatctgggacagtagaaagggcttcatca tatcaaatgcaacgtacaaagaaatagggcttctgacctgtgaagcaacagtcaatgggcatttgtataa gacaaactatctcacacatcgacaaaccaatacaatcatcgatgtggttctgagtccgtctcatggaatt gaactatctgttggagaaaagcttgtcttaaattgtacagcaagaactgaactaaatgtggggattgact tcaactgggaataccccttcttcgaagcatcagcataagaaacttgtaaaccgagacctaaaaacccagtc tgggagtgagatgaagaaattttttgagcacccttaactatagatggtgtaacccggagtgaccaaggattg tacacctgtgcagcatccagtgggctgatgaccaagaagaacagcacatttgtcagggtccatgaaaaag acaaaactcacacatgcccaccgtgcccagcacctgaactcctggggggaccgtcagtcttcctcttccc cccaaaacccaaggacaccctcatgatctcccggacccctgaggtcacatgcgtggtggtggacgtgagc cacgaagaccctgaggtcaagttcaactggtacgtggacggcgtggaggtgcataatgccaagacaaagc cgcggggaggagcagtacaacagcacgtaccgtgtggtcagcgtcctcaccgtcctgcaccaggactggct gaatggcaaggagtacaagtgcaaggtctccaacaaagccctcccagcccccatcgagaaaaccatctcc aaagccaaagggcagccccgagaaccacaggtgtacaccctgcccccatcccgggatgagctgaccaaga accaggtcagcctgacctgcctggtcaaaggcttctatcccagcgacatcgccgtggagtgggagagcaa tgggcagccggagaacaactacaagaccacgcctcccgtgctggactccgacggctccttcttcctctac agcaagctcaccgtggacaagagcaggtggcagcaggggaacgtcttctcatgctccgtgatgcatgagg ctctgcacaaccactacacgcagaagagcctctccctgtctccgggt (SEQ ID NO: 22)
mvsywdtgvllcallsclllltgsssgsrsdtgrpfvemyseipeiihmtegrelvipervtspnitvtlk kfpldtlipdgkriiwdsrkgfiisnatykeiglltceatvnghlyktnylthrqtntiidvvlspshgi elsvgeklvinctartelnvgidfnweypsskhqhkklvnrdlktgsgsemkkflstltidgvtrsdqgl ytcaassglmtkknstfvrvhekdkthtcppcpapellggpsvflfppkpkdtlmisrtpevtcvvvdvs -continued hedpevkfnwyydgvevhnaktkpreeqynstyrvvsvltvlhqdwlngkeykckvsnkalpapiektis
kakggprepqvytlppsrdeltknqvsltclvkgfypsdiavewesngqpennykttppvldsdgsffly
skltvdksrwqqgnvfscsvmhealhnhytqkslslspg p964

(SEQ ID NO: 23)
atgcggcttccgggtgcgatgccagctctggccctcaaaggcgagctgctgttgctgtctcctgttac
ttctggaaccacagatctctcagggcctggtcgtcacaccccgggccagagcttgtcctcaatgtctc
cagcaccttcgttctgacctgctcgggttcagctccggtggtgtgggaacggatgtcccaggagcccca
caggaaatggccaaggcccaggatggcaccttctccagcgtgctcacactgaccaacctcactgggctag
acacgggagaatactttttgcacccacaatgactcccgtggactggagaccgatgagcggaaacggctcta
catctttgtgccagatcccaccgtgggcttcctccctaatgatgccgaggaactattcatctttctcacg
gaaataactgagatcaccattccatgccgagtaacagacccacagctggtggtgacactgcacgagaaga
aaggggacgttgcactgcctgtcccctatgatcaccaacgtggcttttctggtatctttgaggacagaag
ctacatctgcaaaaccaccattggggacagggaggtggattctgatgcctactatgtctacagactccag
gtgtcatccatcaacgtctctgtgaacgcagtgcagactgtggtccgccagggtgagaacatcaccctca
tgtgcattgtgatcgggaatgaggtggtcaacttcgagtggacataccccgcaaagaaagtgggcggct
ggtggagccggtgactgacttcctcttggatatgccttaccacatccgctccatcctgcacatccccagt
gccgagttagaagactcggggacctacacctgcaatgtgacggagagtgtgaatgaccatcaggatgaaa
aggccatcaacatcaccgtggttgagagcggctacgtgcggctcctgggagaggtgggcacactacaatt
tgctgagctgcatcggagccggacactgcaggtagtgttcgaggcctacccaccgcccactgtcctgtgg
ttcaaagacaaccgcaccctgggcgactccagcgctggcgaaatcgccctgtccacgcgcaacgtgtcgg
agacccggtatgtgtcagagctgacactggttcgcgtgaaggtggcagaggctggccactacaccatgcg
ggccttccatgaggatgctgaggtccagctctccttccagctacagatcaatgtccctgtccgagtgctg
gagctaagtgagagccaccctgacagtggggaacagacagtccgctgtcgtggccggggcatgccccagc
cgaacatcatctggtctgcctgcagagacctcaaaaggtgtccacgtgagctgccgcccacgctgctggg
gaacagttccgaagaggagagccagctggagactaacgtgacgtactgggaggaggagcaggagtttgag
gtggtgagcacactgcgtctgcagcacgtggatcggccactgtcggtgcgctgcacgctgcgcaacgctg
tgggccaggacacgcaggaggtcatcgtggtgccacactccttgcccttcaagcccccatgcccatcatg
cccagcacctgagttcctggggggaccatcagtcttcctgttccccccaaaacccaaggacactctcatg
atctcccggacccctgaggtcacgtgcgtggtggtggacgtgagccaggaagaccccgaggtccagttca
actggtacgtggatggcgtggaggtgcataatgccaagacaaagccgcgggaggagcagttcaacagcac
gtaccgtgtggtcagcgtcctcaccgtcctgcaccaggactggctgaacggcaaggagtacaagtgcaag
gtctccaacaaggcctcccgtcctccatcgagaaaaccatctccaaagccaaagggcagccccgagagc
cacaggtgtacaccctgcccccatcccaggaggagatgaccaagaaccaggtcagcctgacctgcctggt
caaaggcttctaccccagcgacatcgccgtggagtgggagagcaatgggcagccggagaacaactacaag
accacgcctcccgtgctggactccgacggctccttcttcctctacagcaggctaaccgtggacaagagca
ggtggcaggaggggaatgtcttctcatgctccgtgatgcatgaggctctgcacaaccactacacacagaa
gagcctctccctgtctctgggtaaa (SEQ ID NO: 24)
mrlpgampalalkgellllslllllepqisqglvvtppgpelvlnvsstfvltcsgsapvvwermsqepp
gemakaqdgtfssvltltnltgldtgeyfcthndsrgletderkrlyifvpdptvgflpndaeelfiflt
eiteitipervtdpqlvvtlhekkgdvalpvpydhqrgfsgifedrsyickttigdrevdsdayyvyrlq -continued vssinvsvnavqtvvrqgenitlmcivignevvnfewtyprkesgrlvepvtdflldmpyhirsilhips aeledsgtytcnvtesvndhqdekainitvvesgyvrllgevgtlqfaelhrsrtlqvvfeayppptvlw fkdnrtlgdssageialstrnvsetryvseltivrvkvaeaghytmrafhedaevqlsfqlqinvpvrvl elseshpdsgeqtvrcrgrgmpqpniiwsacrdlkrcprelpptllgnsseeesqletnvtyweeeqefe vvstlrlqhvdrplsvrctlrnavgqdtqevivvphslpfkppcpscpapeflggpsvflfppkpkdtlm isrtpevtcvvvdvsqedpevqfnwyvdgvevhnaktkpreeqfnstyrvvsvltvlhqdwingkeykck vsnkglpssiektiskakgqprepqvytlppsqeemtknqvsltclvkgfypsdiavewesngqpennyk ttppvldsdgsfflysrltvdksrwqegnvfscsvmhealhnhytqkslslslgk p963

(SEQ ID NO: 25)

atgcggcttccgggtgcgatgccagctctggccctcaaaggcgagctgctgttgctgtctcctgttac ttctggaaccacagatctctcagggcctggtcgtcacaccccggggccagagcttgtcctcaatgtctc cagcaccttcgttctgacctgctcgggttcagctccggtggtgtgggaacggatgtcccaggagccccca caggaaatggccaaggcccaggatggcaccttctccagcgtgctcacactgaccaacctcactgggctag acacgggagaatacttttgcacccacaatgactcccgtggactggagaccgatgagcggaaacggctcta catctttgtgccagatcccaccgtgggcttcctccctaatgatgccgaggaactattcatctttctcacg gaaataactgagatcaccattccatgccgagtaacagacccacagctggtggtgacactgcacgagaaga aggggacgttgcactgcctgtccctatgatcaccaacgtggcttttctggtatctttgaggacagaag ctacatctgcaaaaccaccattggggacaggaggtggattctgatgcctactatgtctacagactccag gtgtcatccatcaacgtctctgtgaacgcagtgcagactgtggtccgccagggtgagaacatcaccctca tgtgcattgtgatcgggaatgaggtggtcaacttcgagtggacatacccccgcaaagaaagtgggcggct ggtggagccggtgactgacttcctcttggatatgccttaccacatccgctccatcctgcacatccccagt gccgagttagaagactcggggacctacacctgcaatgtgacggagagtgtgaatgaccatcaggatgaaa aggccatcaacatcaccgtggttgagagcggctacgtgggctcctgggagaggtgggcacactacaatt tgctgagctgcatcggagccggacactgcaggtagtgttcgaggcctacccaccgcccactgtcctgtgg ttcaaagacaaccgcaccctgggcgactccagcgctggcgaaatcgccctgtccacgcgcaacgtgtcgg agacccggtatgtgtcagagctgacactggttcgcgtgaaggtggcagaggctggccactacaccatgcg ggccttccatgaggatgctgaggtccagctctccttccagctacagatcaatgtccctgtccgagtgctg gagctaagtgagagccaccctgacagtggggaacagacagtccgctgtcgtggccggggcatgccccagc cgaacatcatctggtctgcctgcagagacctcaaaaggtgtccacgtgagctgccgcccacgctgctggg gaacagttccgaagaggagagccagctggagactaacgtgacgtactgggaggaggagcaggagtttgag gtggtgagcacactgcgtctgcagcacgtggatcggccactgtcggtgcgctgcacgctgcgcaacgctg tgggccaggacacgcaggaggtcatcgtggtgccacactccttgcccttcaaggaccccgagcccaaatc ttgtgacaaaactcacacatgcccaccgtgcccagcacctgaactcctggggggaccgtcagtcttcctc ttcccccccaaaacccaaggacacactcatgatctcccggacccctgaggtcacatgcgtggtggtggacg tgagccacgaagaccctgaggtcaagttcaactggtacgtggacggcgtggaggtgcataatgccaagac aaagccgcgggaggagcagtacaacagcacgtaccgtgtggtcagcgtcctcaccgtcctgcaccaggac tggctgaatggcaaggagtacaagtgcaaggtctccaacaaagccctcccagcccccatcgagaaaacca tctccaaagccaaagggcagccccgagaaccacaggtgtacaccctgcccccatcccgggatgagctgac caagaaccaggtcagcctgacctgcctggtcaaaggcttctatcccagcgacatcgccgtggagtgggag agcaatgggcagccggagaacaactacaagaccacgcctcccgtgctggactccgacggctccttcttcc -continued tctacagcaagctcaccgtggacaagagcaggtggcagcaggggaacgtcttctcatgctccgtgatgca tgaggctctgcacaaccactacacgcagaagagcctctccctgtctccgggtaaa (SEQ ID NO: 26)
mrlpgampalalkgellllslllllepqisqglvvtppgpelvinvsstfvltcsgsapvvwermsqepp qemakaqdgtfssvltltnitgldtgeyfcthndsrgletderkrlyifvpdptvgflpndaeelfiflt eiteitipcrvtdpqlvvtlhekkgdvalpvpydhqrgfsgifedrsyickttigdrevdsdayyvyrlq vssinvsvnavqtvvrqgenitlmcivignevvnfewtyprkesgrlvepvtdflldmpyhirsilhips aeledsgtytcnvtesvndhqdekainitvvesgyvrllgevgtlqfaelhrsrtlqvvfeayppptvlw fkdnrtlgdssageialstrnvsetryvseltivrvkvaeaghYtmrafhedaevqlsfqlqinvpvrvl elseshpdsgeqtvrcrgrgmpqpniiwsacrdlkrcprelpptllgnsseeesqletnvtyweeeqefe vvstlrlqhvdrplsvrctlrnavgqdtqevivvphslpfkdpepkscdkthtcppcpapellggpsvfl fppkpkdtlmisrtpevtcvvvdvshedpevkfnwyvdgvevhnaktkpreeqynstyrvvsvltvlhqd wingkeykckvsnkalpapiektiskakgqprepqvytlppsrdeltknqvsltclvkgfypsdiavewe sngqpennykttppvldsdgsfflyskltvdksrwqqgnvfscsvmhealhnhytqkslslspgk p974
(SEQ ID NO: 27)
atgcggcttccgggtgcgatgccagctctggccctcaaaggcgagctgctgttgctgtctcctgttac ttctggaaccacagatctctcagggcctggtcgtcacaccccgggcccagagcttgtcctcaatgtctc cagcaccttcgttctgacctgctcggggttcagctccggtggtgtgggaacggatgtcccaggagcccca caggaaatggccaaggcccaggatggcaccttctccagcgtgctcacactgaccaacctcactgggctag acacgggagaatacttttgcacccacaatgactcccgtggactggagaccgatgagcggaaacggctcta catctttgtgccagatcccaccgtgggcttcctccctaatgatgccgaggaactattcatctttctcacg gaaataactgagatcaccattccatgccgagtaacagacccacagctggtggtgacactgcacgagaaga aggggacgttgcactgcctgtcccctatgatcaccaacgtggcttttctggtatctttgaggacagaag ctacatctgcaaaaccaccattggggacagggaggtggattctgatgcctactatgtctacagactccag gtgtcatccatcaacgtctctgtgaacgcagtgcagactgtggtccgccagggtgagaacatcacccctca tgtgcattgtgatcgggaatgaggtggtcaacttcgagtggacataccccgcaaagaaagtgggcggct ggtggagccggtgactgacttcctcttggatatgccttaccacatccgctccatcctgcacatccccagt gccgagttagaagactcggggacctacacctgcaatgtgacggagagtgtgaatgaccatcaggatgaaa aggccatcaacatcaccgtggttgagagcggctacgtgcggctcctgggagagcccaaatcttgtgacaa aactcacacatgcccaccgtgcccagcacctgaactcctgggggaccgtcagtcttcctcttccccca aaacccaaggacaccctcatgatctcccggacccctgaggtcacatgcgtggtggtggacgtgagccacg aagaccctgaggtcaagttcaactggtacgtggacggcgtggaggtgcataatgccaagacaaagccgcg ggaggagcagtacaacagcacgtaccgtgtggtcagcgtcctcaccgtcctgcaccaggactggctgaat ggcaaggagtacaagtgcaaggtctccaacaaagccctcccagcccccatcgagaaaaccatctccaaag ccaaagggcagccccgagaaccacaggtgtacaccctgcccccatcccgggatgagctgaccaagaacca ggtcagcctgacctgcctggtcaaaggcttctatcccagcgacatcgccgtggagtgggagagcaatggg cagccggagaacaactacaagaccacgcctcccgtgctggactccgacggctccttcttcctctacagca agctcaccgtggacaagagcaggtggcagcaggggaacgtcttctcatgctccgtgatgcatgaggctct gcacaaccactacacgcagaagagcctctccctgtctccgggtaaa (SEQ ID NO: 28)
mrlpgampalalkgellllslllllepqisqglvvtppgpelvlnvsstfvltcsgsapvvwermsqepp qemakaqdgtfssvltltnltgldtgeyfcthndsrgletderkrlyifvpdptvgflpndaeelfiflt -continued eiteitipcrvtdpqlvvtlhekkgdvalpvpydhqrgfsgifedrsyickttigdrevdsdayyvyrlq vssinvsvnavqtvvrqgenitlmcivignevvnfewtyprkesgrlvepvtdflldmpyhirsilhips aeledsgtytcnvtesvndhqdekainitvvesgyvrllgepkscdkthtcppcpapellggpsvflfpp kpkdtlmisrtpevtcvvvdvshedpevkfnwyvdgvevhnaktkpreeqynstyrvvsvltvlhqdwln gkeykckvsnkalpapiektiskakgqprepqvytlppsrdeltknqvsltclvkgfypsdiavewesng qpennykttppvldsdgsfflyskltvdksrwqqgnvfscsvmhealhnhytqkslslspgk p978

(SEQ ID NO: 29)
atgcggcttccgggtgcgatgccagctctggccctcaaaggcgagctgctgttgctgtctctcctgttac ttctggaaccacagatctctcagggcctggtcgtcacaccccgggccagagcttgtcctcaatgtctc cagcaccttcgttctgacctgctcgggttcagctccggtggtgtgggaacggatgtcccaggagcccca caggaaatggccaaggcccaggatggcaccttctccagcgtgctcacactgaccaacctcactgggctag acacgggagaatacttttgcacccacaatgactcccgtggactggagaccgatgagcggaaacggctcta catctttgtgccagatcccaccgtgggcttcctccctaatgatgccgaggaactattcatctttctcacg gaaataactgagatcaccattccatgccgagtaacagacccacagctggtggtgacactgcacgagaaga aggggacgttgcactgcctgtcccctatgatcaccaacgtggcttttctggtatctttgaggacagaag ctacatctgcaaaaccaccattggggacagggaggtggattctgatgcctactatgtctacagactccag gtgtcatccatcaacgtctctgtgaacgcagtgcagactgtggtccgccagggtgagaacatcaccctca tgtgcattgtgatcgggaatgaggtggtcaacttcgagtggacatacccccgcaaagaaagtgggcggct ggtggagccggtgactgacttcctcttggatatgccttaccatccgctccatcctgcacatccccagt gccgagttagaagactcggggacctacacctgcaatgtgacggagagtgtgaatgaccatcaggatgaaa aggccatcaacatcaccgtggttgagagcggctacgtgcggctcctgggagaggtgggcacactacaatt tgctgagctgcatcggagccggacactgcaggtagtgttcgaggcctacccaccgcccactgtcctgtgg ttcaaagacaaccgcaccctgggcgactccagcgctggcgaaatcgccctgtccacgcgcaacgtgtcgg agacccggtatgtgtcagagctgacactggttcgcgtgaaggtggcagaggctggccactacaccatgcg ggccttccatgaggatgctgaggtccagctctccttccagctacagatcaatgtccctgtccgagtgctg gagctaagtgagagccaccctgacagtggggaacagacagtccgctgtcgtggccggggcatgccccagc cgaacatcatctggtctgcctgcagagacctcaaaaggtgtccacgtgagctgccgcccacgctgctggg gaacagttccgaagaggagagccagctggagactaacgtgacgtactgggaggaggagcaggagtttgag gtggtgagcacactgcgtctgcagcacgtggatcggccactgtcggtgcgctgcacgctgcgcaacgctg tgggccaggacacgcaggaggtcatcgtggtgccacactccttgcccttcaag (SEQ ID NO: 30)
mrlpgampalalkgellllsllllllepqisqglvvtppgpelvlnvsstfvltcsgsapvvwermsqepp qemakaqdgtfssvltltnltgldtgeyfcthndsrgletderkrlyifvpdptvfglpndaeelfiflt eiteitipcrvtdpqlvvtlhekkgdvalpvpydhqrgfsgifedrsyickttigdrevdsdayyvyrlq vssinvsvnavqtvvrqgenitlmcivignevvnfewtyprkesgrlvepvtdflldmpyhirsilhips aeledsgtytcnvtesvndhqdekainitvvesgyvrllgevgtlqfaelhrsrtlqvvfeaypppptvlw fkdnrtlgdssageialstrnvsetryvseltlvrvkvaeaghytmrafhedaevqlsfqlqinvpvrvl elseshpdsgeqtvrcrgrgmpqpniiwsacrdlkrcprelpptllgnsseeesqletnvtyweeeqefe vvstlrlqhvdrplsvrctlrnavgqdtqevivvphslpfk -continued p977

(SEQ ID NO: 31)

atggggcagtgcaggaaaagtggcactatgaaccctgcagccctagacaattgtactaaccttcttctct ttcctctcctgacaggttggtgtacagtagcttccaagtactccaccatgcggcttccgggtgcgatgcc agctctggccctcaaaggcgagctgctgttgctgtctcctgttacttctggaaccacagatctctcag ggcctggtcgtcacaccccggggccagagcttgtcctcaatgtctccagcaccttcgttctgacctgct cgggttcagctccggtggtgtgggaacggatgtcccaggagcccccacaggaaatggccaaggcccagga tggcaccttctccagcgtgctcacactgaccaacctcactgggctagacacgggagaatactttgcacc cacaatgactcccgtggactggagaccgatgagcggaaacggctctacatctttgtgccagatcccaccg tgggcttcctccctaatgatgccgaggaactattcatctttctcacggaaataactgagatcaccattcc atgccgagtaacagacccacagctggtggtgacactgcacgagaagaaagggacgttgcactgcctgtc ccctatgatcaccaacgtggcttttctggtatctttgaggacagaagctacatctgcaaaaccaccattg gggacagggaggtggattctgatgcctactatgtctacagactccaggtgtcatccatcaacgtctctgt gaacgcagtgcagactgtggtccgccagggtgagaacatcaccctcatgtgcattgtgatcgggaatgag gtggtcaacttcgagtggacataccccgcaaagaaagtgggcggctggtggagccggtgactgacttcc tcttggatatgccttaccacatccgctccatcctgcacatccccagtgccgagttagaagactcggggac ctacacctgcaatgtgacggagagtgtgaatgaccatcaggatgaaaaggccatcaacatcaccgtggtt gagagcggctacgtgcggctcctgggagaggtgggcacactacaatttgctgagctgcatcggagccgga cactgcaggtagtgttcgaggcctacccaccgcccactgtcctgtggttcaaagacaaccgcaccctggg cgactccagcgctggcgaaatcgccctgtccacgcgcaacgtgtcggagacccggtatgtgtcagagctg acactggttcgcgtgaaggtggcagaggctggccactacaccatgcgggccttccatgaggatgctgagg tccagctctccttccagctacagatcaatgtccctgtccgagtgctggagctaagtgagagccaccctga cagtggggaacagacagtccgctgtcgtggccggggcatgccccagccgaacatcatctggtctgcctgc agagacctcaaaaggtgtccacgtgagctgccgcccacgctgctggggaacagttccgaagaggagagcc agctggagactaacgtgacgtactgggaggaggagcaggagtttgaggtggtgagcacactgcgtctgca gcacgtggatcggccactgtcggtgcgctgcacgctgcgcaacgctgtgggccaggacacgcaggaggtc atcgtggtgccacactctttgcccttcaagcggggcagccaccaccaccaccac (SEQ ID NO: 32)

mgqcrksgtmnpaaldnctnllllfplltgwctvaskystmrlpgampalalkgelllllsllllllepqisq glvvtppgpelvinvsstfvltcsgsapvvwermsqeppqemakaqdgtessvltltnitgldtgeyfct hndsrgletderkrlyifvpdptvgflpndaeelfifllteiteitipervtdpqlvvtlhekkgdvalpv pydhqrgfsgifedrsyickttigdrevdsdayyvyrlqvssinvsvnavqtvvrqgenitlmcivigne vvnfewtyprkesgrlvepvtdflldmpyhirsilhipsaeledsgtytcnvtesvndhqdekainitvv esgyvrllgevgtlqfaelhrsrtlqvvfeaypppptvlwfkdnrtlgdssageialstrnvsetryvsel tivrvkvaeaghytmrafhedaevqlsfqlqinvpvrvlelseshpdsgeqtvrcrgrgmpqpniiwsac rdlkrcprelpptllgnsseeesqletnvtyweeeqefevvstlrlqhvdrplsvrctlrnavgqdtqev ivvphslpfkrgshhhhhh A wide variety of host/expression vector combinations may be used to express the gene encoding the growth factor, or other biologically active molecule(s) of interest. Long-term, stable in vivo expression is achieved using expression vectors (i.e., recombinant DNA molecules) in which the gene encoding the anti-angiogenic antibody-scaffold or the anti-angiogenic molecule, such as the VEGF receptor or the PDGF receptor is operatively linked to a promoter that is not subject to down regulation upon implantation in vivo in a mammalian host. Suitable promoters include, for example, strong constitutive mammalian promoters, such as beta-actin, eIF4A1, GAPDH, etc. Stress-inducible promoters, such as the metallothionein 1 (MT-1) or VEGF promoter may also be suitable. Additionally, hybrid promoters containing a core promoter and custom 5' UTR or enhancer elements may be used. Other known non-retroviral promoters capable of controlling gene expression, such as CMV or the early and late promoters of SV40 or adenovirus are suitable. Enhancer elements may also be place to confer additional gene expression under stress environments, such as low $O_2$. One example is the erythropoietin enhancer which confers up-regulation of associated gene elements upon hypoxic induction.

The expression vectors containing the gene of interest may then be used to transfect the desired cell line. Standard transfection techniques such as liposomal, calcium phosphate co-precipitation, DEAE-dextran transfection or electroporation may be utilized. Commercially available mammalian transfection kits, such as Fugene6 (Roche Applied Sciences), may be purchased. Additionally, viral vectors may be used to transducer the desired cell line. An example of a suitable viral vector is the commercially available pLenti family of viral vectors (Invitrogen). Human mammalian cells can be used. In all cases, it is important that the cells or tissue contained in the device are not contaminated or adulterated. For antibody scaffold proteins requiring heavy and light chain components, dual constructs, each encoding a relevant antibody heavy or light chain, can be co-transfected simultaneously, thereby yielding cell lines expressing functional bivalent Fab and tetravalent full antibody molecules.

Preferred promoters used in the disclosed constructs include the SV40 promoter and the CMV/EF1alpha promoter, as shown in FIG. 1.

Other useful expression vectors, for example, may consist of segments of chromosomal, non-chromosomal and synthetic DNA sequences, such as various known derivatives of SV40 and known bacterial plasmids, e.g., pUC, pBlue-Script™ plasmids from *E. coli* including pBR322, pCR1, pMB9 and their derivatives. Expression vectors containing the geneticin (G418), hygromycin or blasticidin drug selection genes (Southern, P. J., In Vitro, 18, p. 315 (1981), Southern, P. J. and Berg, P., J. Mol. Appl. Genet., 1, p. 327 (1982)) are also useful. These vectors can employ a variety of different enhancer/promoter regions to drive the expression of both a biologic gene of interest and/or a gene conferring resistance to selection with toxin such as G418, hygromycin B, or blasticidin. A variety of different mammalian promoters can be employed to direct the expression of the genes for G418 and hygromycin B and/or the biologic gene of interest. The G418 resistance gene codes for aminoglycoside phosphotransferase (APH) which enzymatically inactivates G418 (100-1000 μg/μl) added to the culture medium. Only those cells expressing the APH gene will survive drug selection usually resulting in the expression of the second biologic gene as well. The hygromycin B phosphotransferase (HPH) gene codes for an enzyme which specifically modifies hygromycin toxin and inactivates it. Genes co-transfected with or contained on the same plasmid as the hygromycin B phosphotransferase gene will be preferentially expressed in the presence of hygromycin B at 50-200 μg/ml concentrations.

Examples of expression vectors that can be employed include, but are not limited to, the commercially available pRC/CMV (Invitrogen), pRC/RSV (Invitrogen), pcDNA1NEO (Invitrogen), pCI-Neo (Promega); pcDNA3.3 (Invitrogen) and GS vector system (Lonza Group, Switzerland). Other suitable commercially available vectors include pBlast, pMono, or pVitro. In one preferred embodiment, the expression vector system is the pCpGfree-vitro expression vectors available with neomycin (G418), hygromycin, and blasticidin resistance genes (InvivoGen, San Diego, Calif.)) (See FIG. 1).

In one embodiment, the pNUT expression vector, which contains the cDNA of the mutant DHFR and the entire pUC18 sequence including the polylinker, can be used. See, e.g., Aebischer, P., et al., Transplantation, 58, pp. 1275-1277 (1994); Baetge et al., PNAS, 83, pp. 5454-58 (1986). The pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above.

Those skilled in the art will recognize that any other suitable, commercially available expression vectors (e.g., pcDNA family (Invitrogen), pBlast, pMono, pVitro, or pCpG-vitro (Invivogen)) can also be used. Principal elements regulating expression are typically found in the expression cassette. These elements include the promoter, 5' untranslated region (5' UTR) and 3' untranslated region (3' UTR). Other elements of a suitable expression vector may be critical to plasmid integration or expression but may not be readily apparent. The skilled artisan will be able to design and construct suitable expression vectors for use in the claimed invention. The choice, design, and/or construction of a suitable vector is well within the routine level of skill in the art.

The genes and cDNA encoding the VEGF1, VEGF2, PDGF alpha, and PDGF beta receptors have been cloned and their nucleotide sequences published. (GenBank Accession U01134 and AF063658, NM_006206, BC032224). Other genes encoding the biologically active molecules useful in this invention that are not publicly available may be obtained using standard recombinant DNA methods such as PCR amplification, genomic and cDNA library screening with oligonucleotide probes. Any of the known genes coding for biologically active molecules may be employed in the methods of this invention.

The cell of choice is the ARPE-19 cell line, a spontaneously arising continuous human retinal pigmented epithelial cell line. However, those skilled in the art will recognize that other suitable cells, including by not limited to CHO cells, BHK cells, RPE (primary cells or immortalized cells), can also be used. The choice of cell depends upon the intended application. The encapsulated cells may be chosen for secretion of a particular anti-angiogenic antibody-scaffold or a VEGF receptor construct. Cells can also be employed which synthesize and secrete agonists, analogs, derivatives or fragments of the construct, which are active. Those skilled in the art will recognize that other suitable cell types may also be genetically engineered to secrete any of the anti-angiogenic antibody-scaffolds or VEGF receptor constructs described herein.

To be a platform cell line for an encapsulated cell based delivery system, the cell line should have as many of the following characteristics as possible: (1) the cells should be hardy under stringent conditions (the encapsulated cells should be functional in the avascular tissue cavities such as in the central nervous system or the eye, especially in the intraocular environment); (2) the cells should be able to be genetically modified (the desired therapeutic factors needed to be engineered into the cells); (3) the cells should have a relatively long life span (the cells should produce sufficient progenies to be banked, characterized, engineered, safety tested and clinical lot manufactured); (4) the cells should preferably be of human origin (which increases compatibility between the encapsulated cells and the host); (5) the cells should exhibit greater than 80% viability for a period of more than one month in vivo in device (which ensures long-term delivery); (6) the encapsulated cells should deliver an efficacious quantity of a useful biological product (which ensures effectiveness of the treatment); (7) the cells should have a low level of host immune reaction (which ensures the longevity of the graft); and (8) the cells should be nontumorigenic (to provide added safety to the host, in case of device leakage).

The ARPE-19 cell line (see Dunn et al., 62 Exp. Eye Res. 155-69 (1996), Dunn et al., 39 Invest. Ophthalmol. Vis. Sci. 2744-9 (1998), Finnemann et al., 94 Proc. Natl. Acad. Sci. USA 12932-7 (1997), Handa et al., 66 Exp. Eye. 411-9 (1998), Holtkamp et al., 112 Clin. Exp. Immunol. 34-43 (1998), Maidji et al., 70 J. Virol. 8402-10 (1996); U.S. Pat. No. 6,361,771) demonstrates all of the characteristics of a successful platform cell for an encapsulated cell-based delivery system. The ARPE-19 cell line is available from the American Type Culture Collection (ATCC Number CRL-2302). ARPE-19 cells are normal retinal pigmented epithelial (RPE) cells and express the retinal pigmentary epithelial cell-specific markers CRALBP and RPE-65. ARPE-19 cells form stable monolayers, which exhibit morphological and functional polarity.

Genetically engineered ARPE-19 cells of the instant invention express one or more anti-angiogenic antibody-scaffolds or anti-angiogenic molecules of the instant invention to produce a therapeutic amount of the anti-angiogenic antibody-scaffold and/or the anti-angiogenic molecule. In some embodiments, the genetically engineered ARPE-19 cells are capable of producing at least 10,000 ng/day/$10^6$ cells. Preferably, these cells are capable of producing this amount for a period of at least 3 months.

In other embodiments, these molecules can be introduced into the ARPE-19 cells using an iterative transfection process. The iterative transfection contains at least one transfection, two transfections, three transfections, or more transfections (e.g., 4, 5, 6, 7, 8, 9, 10, or more) transfections. The cell line of the instant invention can produce between 10,000 and 30,000 ng/day/$10^6$ cells, preferably about or at least 15,000 ng/day/$10^6$ cells of the one or more antibody scaffolds based biologics and receptor fusion proteins (i.e., anti-angiogenic antibody-scaffolds or anti-angiogenic molecules) when the iterative transfection is one transfection. Alternatively, the cell line can produce between 30,000 and 50,000 ng/day/$10^6$ cells, preferably about or at least 35,000 ng/day/$10^6$ cells of the one or more anti-angiogenic antibody-scaffolds or anti-angiogenic molecules when the iterative transfection is two transfections. In other embodiments, the cell line produces between 50,000 and 75,000 ng/day/$10^6$ cells, preferably about or at least 70,000 ng/day/$10^6$ cells of the one or more anti-angiogenic antibody-scaffolds or anti-angiogenic molecules when the iterative transfection is three transfections. In some embodiments, the same anti-angiogenic antibody-scaffolds or anti-angiogenic molecules can be introduced into the cells using such iterative transfection. Alternatively, different anti-angiogenic antibody-scaffolds or anti-angiogenic molecules are introduced into the cells in each transfection of the iterative transfection.

When the devices of the invention are used, preferably between $10^2$ and $10^8$ engineered ARPE-19 cells, most preferably 0.5-1.0×$10^6$ or 5×$10^2$ to 6×$10^5$ ARPE-19 cells that have been genetically engineered to secrete one or more anti-angiogenic antibody-scaffolds or VEGF or PDGF receptor constructs described herein are encapsulated in each device. Dosage may be controlled by implanting a fewer or greater number of capsules, preferably between 1 and 50 capsules per patient. The ophthalmic devices described herein are capable of delivering between about 0.1 pg and 1000 µg of the anti-angiogenic antibody-scaffold(s) or soluble VEGF receptor or PDGF receptor construct(s) per eye per patient per day. In one non-limiting example, the therapeutic amount is 500-50,000 ng steady state per eye. In another example, the therapeutic amount is at least 10 µg/ml steady state per eye. Moreover, the cells lines and devices of the instant invention are able to express this therapeutic amount for a period of at least three months.

Techniques and procedures for isolating cells or tissues which produce a selected product are known to those skilled in the art, or can be adapted from known procedures with no more than routine experimentation.

If the cells to be isolated are replicating cells or cell lines adapted to growth in vitro, it is particularly advantageous to generate a cell bank of these cells. A particular advantage of a cell bank is that it is a source of cells prepared from the same culture or batch of cells. That is, all cells originated from the same source of cells and have been exposed to the same conditions and stresses. Therefore, the vials can be treated as homogenous culture. In the transplantation context, this greatly facilitates the production of identical or replacement devices. It also allows simplified testing protocols, which insure that implanted cells are free of retroviruses and the like. It may also allow for parallel monitoring of vehicles in vivo and in vitro, thus allowing investigation of effects or factors unique to residence in vivo.

As used herein, the terms "individual" or "recipient" or "host" are used interchangeably to refer to a human or an animal subject.

A "biologically active molecule" ("BAM") is a substance that is capable of exerting a biologically useful effect upon the body of an individual in whom a device of the present invention is implanted. For example, the anti-angiogenic antibody-scaffolds and VEGF receptor constructs described herein are examples of BAMs.

The terms "capsule" and "device" and "vehicle" are used interchangeably herein to refer to the ECT devices of the invention.

Unless otherwise specified, the term "cells" means cells in any form, including but not limited to cells retained in tissue, cell clusters, and individually isolated cells.

As used herein a "biocompatible capsule" or "biocompatible device" or "biocompatible vehicle" means that the capsule or device or vehicle, upon implantation in an individual, does not elicit a detrimental host response sufficient to result in the rejection of the capsule or to render it inoperable, for example through degradation.

As used herein an "immunoisolatory capsule" or "immunoprotective capsule" or "immunoisolatory device" or "immunoprotective device" or "immunoisolatory vehicle" or "immunoprotective vehicle" means that the capsule upon implantation into an individual, favorably partitions the device cellular contents and minimizes the deleterious effects of the host's immune system on the cells within its core.

As used herein "long-term, stable expression of a biologically active molecule" means the continued production of a biologically active molecule at a level sufficient to maintain its useful biological activity for periods greater than one month, preferably greater than three months and most preferably greater than six months. Implants of the devices and the contents thereof are able to retain functionality for greater than three months in vivo and in many cases for longer than a year, and in some cases longer than two years or more.

The terms "jacket" and "semi-permeable membrane" are used interchangeably herein.

The term "internal scaffold" is one example of a "matrix" that can be used in the devices described herein.

The "semi-permeable" nature of the jacket membrane surrounding the core permits molecules produced by the cells (e.g., metabolites, nutrients and/or therapeutic substances) to diffuse from the device into the surrounding host eye tissue, but is sufficiently impermeable to protect the cells in the core from detrimental immunological attack by the host.

The exclusion of IgG from the core of the vehicle is not the touchstone of immunoisolation, because in most cases IgG alone is insufficient to produce cytolysis of the target cells or tissues. Thus, for immunoisolatory capsules, jacket nominal molecular weight cutoff (MWCO) values up to 1000 kD are contemplated. Preferably, the MWCO is between 50-700 kD, Most preferably, the MWCO is between 70-300 kD. See, e.g., WO 92/19195. In one preferred embodiment, the MWCO is 500 kD.

The instant invention also relates to biocompatible, optionally immunoisolatory and/or immunoprotective, devices for the delivery of one or more of the anti-angiogenic antibody-scaffolds or soluble VEGF receptors described herein to the eye. Such devices contain a core containing living cells that produce or secrete the anti-angiogenic antibody-scaffold, the VEGF receptor, or the PDGF receptor and a biocompatible jacket surrounding the core, wherein the jacket has a molecular weight cut off ("MWCO") that allows the diffusion of the anti-angiogenic antibody-scaffold or the VEGF receptor into the eye and to the central nervous system, including the brain, ventricle, spinal cord.

The invention also provides biocompatible and implantable and optionally immunoisolatory and/or immunoprotective devices, containing a core having cells that produces or secretes one or more anti-angiogenic antibody-scaffolds or anti-angiogenic molecules and a semi-permeable membrane surrounding the cells, which permits the diffusion of the one or more anti-angiogenic antibody-scaffolds or anti-angiogenic molecules there through.

Such devices may include one, two, three, four, five, six, seven or all of the following additional characteristics:
 a. the core contains about $0.5-1.0 \times 10^6$ ARPE-19 cells;
 b. the length of the device is about 4 mm-11 mm;
 c. the internal diameter of the device is between 0.9 mm-1.2 mm;
 d. the ends of the device are sealed using methyl methacrylate;
 e. the semi-permeable membrane has a median pore size of about 100 nm;
 f. the nominal molecular weight cut off (MWCO) of the semi-permeable membrane is 500 kD;
 g. the semi-permeable membrane is between 90-120 um thick;
 h. the core contains an internal scaffold, wherein the scaffold comprises polyethylene terephthalate (PET) fibers that comprises between 40-85% of internal volume of the device;
 i. any combination(s) thereof.

A variety of biocompatible capsules are suitable for delivery of molecules according to this invention. Useful biocompatible polymer capsules comprise (a) a core which contains a cell or cells, either suspended in a liquid medium or immobilized within a biocompatible matrix, and (b) a surrounding jacket comprising a membrane which does not contain isolated cells, which is biocompatible, and permits diffusion of the cell-produced biologically active molecule into the eye.

Many transformed cells or cell lines are advantageously isolated within a capsule having a liquid core, comprising, e.g., a nutrient medium, and optionally containing a source of additional factors to sustain cell viability and function. The core of the devices of the invention can function as a reservoir for growth factors (e.g., prolactin, or insulin-like growth factor 2), growth regulatory substances such as transforming growth factor β (TGF-β) or the retinoblastoma gene protein or nutrient-transport enhancers (e.g., perfluorocarbons, which can enhance the concentration of dissolved oxygen in the core). Certain of these substances are also appropriate for inclusion in liquid media.

In addition, any of the instant devices can also be used as a reservoir for the controlled delivery of needed drugs or biotherapeutics. In such cases, the core contains a high concentration of the selected drug or biotherapeutic (alone or in combination with cells or tissues). In addition, satellite vehicles containing substances which prepare or create a hospitable environment in the area of the body in which a device according to the invention is implanted can also be implanted into a recipient. In such instances, the devices containing immunoisolated cells are implanted in the region along with satellite vehicles releasing controlled amounts of, for example, a substance which down-modulates or inhibits an inflammatory response from the recipient (e.g., anti-inflammatory steroids), or a substance which stimulates the ingrowth of capillary beds (e.g., an angiogenic factor).

Alternatively, the core may comprise a biocompatible matrix of a hydrogel or other biocompatible material (e.g., extracellular matrix components) which stabilizes the position of the cells. The term "hydrogel" herein refers to a three dimensional network of cross-linked hydrophilic polymers. The network is in the form of a gel, substantially composed of water, preferably gels being greater than 90% water. Compositions which form hydrogels fall into three classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly crosslinked polyethylene oxide, or polyvinylalcohol).

Any suitable matrix or spacer may be employed within the core, including precipitated chitosan, synthetic polymers and polymer blends, microcarriers and the like, depending upon the growth characteristics of the cells to be encapsulated.

Alternatively, the devices may have an internal scaffold. The scaffold may prevent cells from aggregating and improve cellular distribution within the device. (See PCT publication no. WO 96/02646). The scaffold defines the microenvironment for the encapsulated cells and keeps the cells well distributed within the core. The optimal internal scaffold for a particular device is highly dependent on the cell type to be used. In the absence of such a scaffold, adherent cells aggregate to form clusters.

For example, the internal scaffold may be a yarn or a mesh. The filaments used to form a yarn or mesh internal scaffold are formed of any suitable biocompatible, substantially non-degradable material. (See U.S. Pat. Nos. 6,303,136 and 6,627,422, which are herein incorporated by reference). Preferably, the capsule of this invention will be similar to those described by PCT International patent applications WO 92/19195 or WO 95/05452, incorporated by reference; or U.S. Pat. Nos. 5,639,275; 5,653,975; 4,892,538; 5,156,844; 5,283,187; or 5,550,050, incorporated by reference. Materials useful in forming yarns or woven meshes include any biocompatible polymers that are able to be formed into fibers such as, for example, acrylic, polyester, polyethylene, polypropylene, polyacrylonitrile, polyethylene terephthalate, nylon, polyamides, polyurethanes, polybutester, or natural fibers such as cotton, silk, chitin or carbon. Any suitable thermoplastic polymer, thermoplastic elastomer, or other synthetic or natural material having fiber-forming properties may be inserted into a pre-fabricated hollow fiber membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and has a long history of implant use. In certain embodiments, the filaments may be "texturized" to provide rough surfaces and "hand-holds" onto which cell projections may attach. The filaments may be coated with extracellular matrix molecules or surface-treated (e.g. plasma irradiation) to enhance cellular adhesion to the filaments.

In some embodiments, the filaments, preferably organized in a non-random unidirectional orientation, are twisted in bundles to form yarns of varying thickness and void volume. Void volume is defined as the spaces existing between filaments. The void volume in the yarn should vary between 20-95%, but is preferably between 50-95%. In one preferred embodiment, the internal scaffold is made from PET fibers that fill between 40-85% of the internal volume of the devices. The preferred void space between the filaments is between 20-200 µm, sufficient to allow the scaffold to be seeded with cells along the length of the yarn, and to allow the cells to attach to the filaments. The preferred diameter of the filaments comprising the yarn is between 5-100 µm. These filaments should have sufficient mechanical strength to allow twisting into a bundle to comprise a yarn. The filament cross-sectional shape can vary, with circular, rectangular, elliptical, triangular, and star-shaped cross-section being preferred.

Alternatively, the filaments or yarns can be woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

In other embodiments, a tubular braid is constructed. The braid can be inserted into a hollow fiber membrane upon which the cells are seeded. Alternatively, the cells can be allowed to infiltrate the wall of the mesh tube to maximize the surface area available for cell attachment. When such cell infiltration occurs, the braid serves both as a cell scaffold matrix and as an inner support for the device. The increase in tensile strength for the braid-supported device is significantly higher than in alternative approaches.

As noted, for implant sites that are not immunologically privileged, such as periocular sites, and other areas outside the anterior chamber (aqueous) and the posterior chamber (vitreous), the capsules are preferably immunoisolatory. Components of the biocompatible material may include a surrounding semipermeable membrane and the internal cell-supporting scaffolding. The transformed cells are preferably seeded onto the scaffolding, which is encapsulated by the permselective membrane, which is described above. Also, bonded fiber structures can be used for cell implantation. (See U.S. Pat. No. 5,512,600, incorporated by reference). Biodegradable polymers include, for example, those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (PCT International patent application Ser. No. 98/05304, incorporated by reference). Woven mesh tubes have been used as vascular grafts (PCT International patent application WO 99/52573, incorporated by reference). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fiber membrane. Such membranes, and methods of making them are disclosed by U.S. Pat. Nos. 5,284,761 and 5,158,881, incorporated by reference. The surrounding semipermeable membrane is formed from a polyether sulfone hollow fiber, such as those described by U.S. Pat. Nos. 4,976,859 or 4,968,733, incorporated by reference. An alternate surrounding semipermeable membrane material is polysulfone.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired.

Preferably the device has a tether that aids in maintaining device placement during implant, and aids in retrieval. Such a tether may have any suitable shape that is adapted to secure the capsule in place. For example, the suture may be a loop, a disk, or a suture. In some embodiments, the tether is shaped like an eyelet, so that suture may be used to secure the tether (and thus the device) to the sclera, or other suitable ocular structure. In another embodiment, the tether is continuous with the capsule at one end, and forms a pre-threaded suture needle at the other end. In one preferred embodiment, the tether is an anchor loop that is adapted for anchoring the capsule to an ocular structure. The tether may be constructed of a shape memory metal and/or any other suitable medical grade material known in the art.

In a hollow fiber configuration, the fiber will have an inside diameter of less than 2000 microns, preferably less than 1200 microns. Also contemplated are devices having an outside diameter less than 300-600 microns. In one preferred embodiment, the inner diameter is between 0.9 mm and 1.2 mm. For implantation in the eye, in a hollow fiber configuration the capsule will preferably be between 0.4 cm to 1.5 cm in length, most preferably between 0.4 to 1.0 cm in length. In one preferred embodiment, the length of the device is between 4 mm and 11 mm. Longer devices may be accommodated in the eye, however, a curved or arcuate shape may be required for secure and appropriate placement. The hollow fiber configuration is preferred for intraocular placement.

For periocular placement, either a hollow fiber configuration (with dimensions substantially as above) or a flat sheet configuration is contemplated. The upper limit contemplated for a flat sheet is approximately 5 mm×5 mm—assuming a square shape. Other shapes with approximately the same surface area are also contemplated.

Microdevices manufactured for delivery of the anti-angiogenic antibody-scaffold, soluble VEGFR or soluble PDGFR may have a length of between 1 and 2.5 millimeters, with an inner diameter of between 300 and 500 microns and an outer diameter of between 450 and 700 microns. In such micronized devices, an inner scaffolding containing between 10 and 60 monofilaments of PET can be utilized. The molecular weight cut off ranges from these micronized devices are between 100 and 2000 kDa. In contrast, passive diffusion of a 70 kDa dextran ranges between 100 and $2000 \times 10^{-10}$ cm$^2$/s. While any suitable membrane material(s) described herein may be used in these micronized devices, two preferred materials are polyethersulfone and/or polysulfone. Moreover, microdevices can be manufactured with and without anchors made of a suitable material (e.g., nitinol). For a complete discussion of micronized devices, see WO2007/078922, which is herein incorporated by reference.

The permselective feature of the membrane contemplated for use in the delivery of antibody-scaffolds, VEGFR and PDGFR constructs described herein has been manufactured by the phase inversion process, know to those familiar with the art, to reside within the inner skin of the membrane. Development of the permselective feature of rejecting skin on the inner surface improves the manufacturing consistency of the pore structure and control of the rejection properties while also protecting the membrane properties throughout the down-stream manufacture of the encapsulating device. The permselective feature of the membrane described by this invention is developed to allow passage of molecular sizes required for therapeutic necessity; however, the characteristics have also been optimized to allow the largest size necessary to be released while restricting molecules only slightly larger than the intended protein size from entering the capsule.

Due to the allogenic nature of interaction between the cells used in the invention and the host recipient, the greatest concern to rejection is from the host immune cell complex mediated attack directly against the transplanted, encapsulated cells rather than from a cytolytic complement mediated attack complex or by interaction of antibody interaction with complement. While the membranes used in this invention are designed to allow passage of molecules up to the size of immunoglobulin G the membrane will still restrict transport of molecules such as C1q (about 400 kDa), the largest molecule required for the assembly of the cellular attack complex. The design of the membrane used in this invention, therefore, will maximize the nutrient and metabolite exchange rate with the host, supporting long-term viability of the transplanted cells within the host, allowing for substantial delivery of the target therapeutic molecules from the encapsulated cells to the host, while preventing complement recognition of the encapsulated cells and direct cell contact with the host.

The open membrane contemplated for use with the anti-angiogenic antibody-scaffolds, the VEGFR and PDGFR constructs described herein will have nominal molecular weight cutoff (MWCO) values up to 1000 kD. Preferably, the MWCO is between 50-700 kD and ideally approximately 300 kD. In one preferred embodiment, the MWCO is 500 kD. The nominal pore size of the membrane contemplated will have a nominal pore size of approximately 100 nm and based upon a Gaussian distribution of pores the largest absolute pores would be less than 150 nm. The passive diffusion of a dextran molecule of the size 70 kDa is between 100 and $2000 \times 10^{-10}$ cm$^2$/s, and preferably the diffusion coefficient of a 70 kDa dextran is closer to $2000 \times 10^{-10}$ cm$^2$/s. The open membrane used with anti-angiogenic antibody-scaffolds and VEGFR constructs will have an upper hydraulic permeability value of approximately 100 mls/min/m$^2$/mmHg. Alternatively, if a very open membrane is not utilized, a more "immunoisolatory" and/or "immunoprotective" membrane will be used. For such an immunoisolatory membrane, the hydraulic permeability will typically be in the range of 0.4-170 mls/min/m$^2$/mmHg, for example, 0.5-100 mls/min/m$^2$/mmHg, preferably in the range of 15 to 50 mls/min/m$^2$/mmHg. Using the testing procedures to determine a single molecular weight rejection recognized by those familiar with the art, the nominal molecular weight cutoff of a more "immunoisolatory" membrane will reject 90% of bovine albumin while the diffusive flux of a 70 kDa dextran molecule will remain approximately $2000 \times 10^{-10}$ cm$^2$/s. The glucose mass transfer coefficient of the capsule, defined, measured and calculated as described by Dionne et al., ASAIO Abstracts, p. 99 (1993), and Colton et al., The Kidney, eds., Brenner B M and Rector F C, pp. 2425-89 (1981) will be greater than $10^{-6}$ cm/sec, preferably greater than $10^{-4}$ cm/sec.

In one preferred embodiment, the median pore size is about 100 nm. The surrounding or peripheral region (jacket), which surrounds the core of the instant devices can be permselective, biocompatible, and/or immunoisolatory. It is produced in such a manner that it is free of isolated cells, and completely surrounds (i.e., isolates) the core, thereby preventing contact between any cells in the core and the recipient's body. Biocompatible semi-permeable hollow fiber membranes, and methods of making them are disclosed in U.S. Pat. Nos. 5,284,761 and 5,158,881 (See also, WO 95/05452), each of which incorporated herein by reference in its entirety. For example, the capsule jacket can be formed from a polyether sulfone hollow fiber, such as those described in U.S. Pat. Nos. 4,976,859 and 4,968,733, and 5,762,798, each incorporated herein by reference.

To be permselective, the jacket is formed in such a manner that it has a molecular weight cut off ("MWCO") range appropriate both to the type and extent of immunological reaction anticipated to be encountered after the device is implanted and to the molecular size of the largest substance whose passage into and out of the device into the eye is desirable. The type and extent of immunological attacks which may be mounted by the recipient following implantation of the device depend in part upon the type(s) of moiety isolated within it and in part upon the identity of the recipient (i.e., how closely the recipient is genetically related to the source of the BAM). When the implanted tissue or cells are allogeneic to the recipient, immunological rejection may proceed largely through cell-mediated attack by the recipient's immune cells against the implanted cells. When the tissue or cells are xenogeneic to the recipient, molecular attack through assembly of the recipient's cytolytic complement attack complex may predominate, as well as the antibody interaction with complement.

The jacket allows passage of substances up to a predetermined size, but prevents the passage of larger substances. More specifically, the surrounding or peripheral region is produced in such a manner that it has pores or voids of a predetermined range of sizes, and, as a result, the device is permselective. The MWCO of the surrounding jacket must be sufficiently low to prevent access of the substances required to carry out immunological attacks to the core, yet sufficiently high to allow delivery of the anti-angiogenic antibody-scaffold or the VEGF receptor or PDGF receptor to the recipient.

Preferably, when truncated anti-angiogenic antibody-scaffolds or VEGF receptors or PDGF receptors are used, the MWCO of the biocompatible jacket of the devices of the instant invention is from about 1 kD to about 150 kD. However, if delivery of a non-truncated anti-angiogenic antibody-scaffold or receptor is desired, an open membrane with a MWCO greater than 200 kD should be used.

As used herein with respect to the jacket of the device, the term "biocompatible" refers collectively to both the device and its contents. Specifically, it refers to the capability of the implanted intact device and its contents to avoid the detrimental effects of the body's various protective systems and to remain functional for a significant period of time. As used herein, the term "protective systems" refers to the types of immunological attack which can be mounted by the immune system of an individual in whom the instant vehicle is implanted, and to other rejection mechanisms, such as the fibrotic response, foreign body response and other types of inflammatory response which can be induced by the presence of a foreign object in the individuals' body. In addition to the avoidance of protective responses from the immune system or foreign body fibrotic response, the term "biocompatible", as used herein, also implies that no specific undesirable cytotoxic or systemic effects are caused by the vehicle and its contents such as those that would interfere with the desired functioning of the vehicle or its contents.

The external surface of the device can be selected or designed in such a manner that it is particularly suitable for implantation at a selected site. For example, the external surface can be smooth, stippled or rough, depending on whether attachment by cells of the surrounding tissue is desirable. The shape or configuration can also be selected or designed to be particularly appropriate for the implantation site chosen.

The biocompatibility of the surrounding or peripheral region (jacket) of the device is produced by a combination of factors. Important for biocompatibility and continued functionality are device morphology, hydrophobicity and the absence of undesirable substances either on the surface of, or leachable from, the device itself. Thus, brush surfaces, folds, interlayers or other shapes or structures eliciting a foreign body response are avoided. Moreover, the device-forming materials are sufficiently pure to insure that unwanted substances do not leach out from the device materials themselves. Additionally, following device preparation, the treatment of the external surface of the device with fluids or materials (e.g. serum) which may adhere to or be absorbed by the device and subsequently impair device biocompatibility is avoided.

First, the materials used to form the device jacket are substances selected based upon their ability to be compatible with, and accepted by, the tissues of the recipient of the implanted device. Substances are used which are not harmful to the recipient or to the isolated cells. Preferred substances include polymer materials, i.e., thermoplastic polymers. Particularly preferred thermoplastic polymer substances are those which are modestly hydrophobic, i.e. those having a solubility parameter as defined in Brandrup J., et al. Polymer Handbook 3rd Ed., John Wiley & Sons, NY (1989), between 8 and 15, or more preferably, between 9 and 14 (Joules/m$^3$)$^{1/2}$. The polymer substances are chosen to have a solubility parameter low enough so that they are soluble in organic solvents and still high enough so that they will partition to form a proper membrane. Such polymer substances should be substantially free of labile nucleophilic moieties and be highly resistant to oxidants and enzymes even in the absence of stabilizing agents. The period of residence in vivo which is contemplated for the particular vehicle must also be considered: substances must be chosen which are adequately stable when exposed to physiological conditions and stresses. Many thermoplastics are known which are sufficiently stable, even for extended periods of residence in vivo, such as periods in excess of one or two years. The choice of materials used to construct the device is determined by a number of factors as described in detail in Dionne WO 92/19195, herein incorporated by reference. Briefly, various polymers and polymer blends can be used to manufacture the capsule jacket. Polymeric membranes forming the device and the growth surfaces therein may include polyacrylates (including acrylic copolymers), polyvinylidenes, polyvinyl chloride copolymers, polyurethanes, polystyrenes, polyamides, polymethylmethacrylate, polyvinyldifluoride, polyolefins, cellulose acetates, cellulose nitrates, polysulfones, polyphosphazenes, polyacrylonitriles, poly(acrylonitrile/covinyl chloride), as well as derivatives, copolymers and mixtures thereof.

A preferred membrane casting solution comprises a either polysulfone dissolved in the water-miscible solvent dimethylacetamide (DMACSO) or polyethersulfone dissolved in the water-miscible solvent butyrolactone. This casting solution can optionally comprise hydrophilic or hydrophobic additives which affect the permeability characteristics of the finished membrane. A preferred hydrophilic additive for the polysulfone or polyethersulfone is polyvinylpyrrolidone (PVP). Other suitable polymers comprise polyacrylonitrile (PAN), polymethylmethacrylate (PMMA), polyvinyldifluoride (PVDF), polyethylene oxide, polyolefins (e.g., polyisobutylene or polypropylene), polyacrylonitrile/polyvinyl chloride (PAN/PVC), and/or cellulose derivatives (e.g., cellulose acetate or cellulose butyrate). Compatible water-miscible solvents for these and other suitable polymers and copolymers are found in the teachings of U.S. Pat. No. 3,615, 024.

Second, substances used in preparing the biocompatible jacket of the device are either free of leachable pyrogenic or otherwise harmful, irritating, or immunogenic substances or are exhaustively purified to remove such harmful substances. Thereafter, and throughout the manufacture and maintenance of the device prior to implantation, great care is taken to prevent the adulteration or contamination of the device or jacket with substances, which would adversely affect its biocompatibility.

Third, the exterior configuration of the device, including its texture, is formed in such a manner that it provides an optimal interface with the eye of the recipient after implantation. Certain device geometries have also been found to specifically elicit foreign body fibrotic responses and should be avoided. Thus, devices should not contain structures having interlayers such as brush surfaces or folds. In general, opposing vehicle surfaces or edges either from the same or adjacent vehicles should be at least 1 mm apart, preferably greater than 2 mm and most preferably greater than 5 mm. Preferred embodiments include cylinders having an outer diameter of between about 200 and 1600 µm and a length between about 0.4 and 1 mm. Preferably, the core of the devices of the invention has a volume of approximately between 2 ul and 20 µl. However, those skilled in the art will recognize that it is also possible to use "micronized" devices having a core volume of less than 0.5 µl (e.g., about 0.3 µl).

The surrounding jacket of the biocompatible devices can optionally include substances which decrease or deter local inflammatory response to the implanted vehicle and/or generate or foster a suitable local environment for the implanted cells or tissues. For example antibodies to one or more mediators of the immune response could be included. Available potentially useful antibodies such as antibodies to the lymphokines tumor necrosis factor (TNF), and to interferons (IFN) can be included in the matrix precursor solution. Similarly, an anti-inflammatory steroid can be included. See Christenson, L., et al., J. Biomed. Mat. Res., 23, pp. 705-718 (1989); Christenson, L., Ph.D. thesis, Brown University, 1989, herein incorporated by reference. Alternatively, a substance which stimulates angiogenesis (ingrowth of capillary beds) can be included.

In some embodiments, the jacket of the present device is immunoisolatory and/or immunoprotective. That is, it protects cells in the core of the device from the immune system of the individual in whom the device is implanted. It does so (1) by preventing harmful substances of the individual's body from entering the core, (2) by minimizing contact between the individual and inflammatory, antigenic, or otherwise harmful materials which may be present in the core and (3) by providing a spatial and physical barrier sufficient to prevent immunological contact between the isolated moiety and detrimental portions of the individual's immune system.

In some embodiments, the external jacket may be either an ultrafiltration membrane or a microporous membrane. Those skilled in the art will recognize that ultrafiltration membranes are those having a pore size range of from about 1 to about 100 nanometers while a microporous membrane has a range of between about 1 to about 10 microns.

The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 50 or 20 to 75 microns are particularly preferred. In one preferred embodiment, the semi-permeable membrane is between 90 and 120 μm thick. Types of immunological attack which can be prevented or minimized by the use of the instant device include attack by macrophages, neutrophils, cellular immune responses (e.g. natural killer cells and antibody-dependent T cell-mediated cytolysis (ADCC)), and humoral response (e.g. antibody-dependent complement mediated cytolysis).

The capsule jacket may be manufactured from various polymers and polymer blends including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Capsules manufactured from such materials are described, e.g., in U.S. Pat. Nos. 5,284,761 and 5,158,881, incorporated herein by reference. Capsules formed from a polyether sulfone (PES) fiber, such as those described in U.S. Pat. Nos. 4,976,859 and 4,968,733, incorporated herein by reference, may also be used.

Depending on the outer surface morphology, capsules have been categorized as Type 1 (T1), Type 2 (T2), Type 1/2 (T1/2), or Type 4 (T4). Such membranes are described, e.g., in Lacy et al., "Maintenance Of Normoglycemia In Diabetic Mice By Subcutaneous Xenografts Of Encapsulated Islets", Science, 254, pp. 1782-84 (1991), Dionne et al., WO 92/19195 and Baetge, WO 95/05452. A smooth outer surface morphology is preferred.

Those skilled in the art will recognize that capsule jackets with permselective, immunoisolatory membranes are preferable for sites that are not immunologically privileged. In contrast, microporous membranes or permselective membranes may be suitable for immunologically privileged sites. For implantation into immunologically privileged sites, capsules made from the PES or PS membranes are preferred.

Any suitable method of sealing the capsules know in the art may be used, including the employment of polymer adhesives and/or crimping, knotting and heat sealing. In addition, any suitable "dry" sealing method can also be used. In such methods, a substantially non-porous fitting is provided through which the cell-containing solution is introduced. Subsequent to filling, the capsule is sealed. Such methods are described in, e.g., U.S. Pat. Nos. 5,653,688; 5,713,887; 5,738,673; 6,653,687; 5,932,460; and 6,123,700, which are herein incorporated by reference. In one preferred method, the ends of the device are sealed using methyl methacrylate.

According to the methods of this invention, other molecules may be co-delivered in addition to the anti-angiogenic antibody-scaffolds or the VEGF receptors described herein. For example, it may be preferable to deliver a trophic factor(s) with an anti-angiogenic factor.

Co-delivery can be accomplished in a number of ways. In this example, antibody and antibody fragments require constructs encoding light and heavy chain sequences. First, cells may be transfected with separate constructs containing the genes encoding the described molecules. Second, cells may be transfected with a single construct containing two or more genes as well as the necessary control elements. Third, two or more separately engineered cell lines can be either co-encapsulated or more than one device can be implanted at the site of interest.

For some indications, it may be preferable to deliver BAMs to two different sites in the eye concurrently. For example, it may be desirable to deliver a neurotrophic factor to the vitreous to supply the neural retina (ganglion cells to the RPE) and to deliver an anti-angiogenic factor (such as one or more of the anti-angiogenic antibody-scaffolds or VEGF receptors of the invention) via the sub-Tenon's space to supply the choroidal vasculature.

This invention also contemplates use of different cell types during the course of the treatment regime. For example, a patient may be implanted with a capsule device containing a first cell type (e.g., BHK cells). If after time, the patient develops an immune response to that cell type, the capsule can be retrieved, or explanted, and a second capsule can be implanted containing a second cell type (e.g., CHO cells). In this manner, continuous provision of the therapeutic molecule is possible, even if the patient develops an immune response to one of the encapsulated cell types.

The methods and devices of this invention are intended for use in a primate, preferably human host, recipient, patient, subject or individual. A number of different ocular implantation sites are contemplated for the devices and methods of this invention. Suitable implantation sites include, but are not limited to, the aqueous and vitreous humors of the eye, the periocular space, the anterior chamber, and/or the Subtenon's capsule. Within the body, implantation sites may include subcutaneous, intraperitoneal, or within the CNS. In addition, implantation may be directed at localized delivery at or near lesions requiring the desired biologic therapy. Example of such disease sites may be inflamed joints, brain and CNS lesions, sites of benign or malignant tumors. Access by the device to the circulatory system can further extend the range of potential disease sites within the body to distally affected organs and tissues.

The type and extent of immunological response by the recipient to the implanted device will be influenced by the relationship of the recipient to the isolated cells within the core. For example, if core contains syngeneic cells, these will not cause a vigorous immunological reaction, unless the recipient suffers from an autoimmunity with respect to the particular cell or tissue type within the device. Syngeneic cells or tissue are rarely available. In many cases, allogeneic or xenogeneic cells or tissue (i.e., from donors of the same species as, or from a different species than, the prospective recipient) may be available. The use of immunoisolatory devices allows the implantation of allogeneic or xenogeneic cells or tissue, without a concomitant need to immunosuppress the recipient. Use of immunoisolatory capsules also allows the use of unmatched cells (allographs). Therefore, the instant device makes it possible to treat many more individuals than can be treated by conventional transplantation techniques.

The type and vigor of an immune response to xenografted tissue is expected to differ from the response encountered when syngeneic or allogeneic tissue is implanted into a recipient. This rejection may proceed primarily by cell-mediated, or by complement-mediated attack. The exclusion of IgG from the core of the vehicle is not the touchstone of immunoprotection, because in most cases IgG alone is insufficient to produce cytolysis of the target cells or tissues. Using immunoisolatory devices, it is possible to deliver needed high molecular weight products or to provide metabolic functions pertaining to high molecular weight substances, provided that critical substances necessary to the mediation of immunological attack are excluded from the immunoisolatory capsule. These substances may comprise the complement attack complex component Clq, or they may comprise phagocytic or cytotoxic cells. Use of immunoisolatory capsules provides a protective barrier between these harmful substances and the isolated cells.

While the devices of the present invention are macrocapsules, those skilled in the art will recognize that microcapsules such as, for example those described in Rha, Lim, and Sun may also be used. (See, Rha, C. K. et al., U.S. Pat. No. 4,744,933; Methods in Enzymology 137, pp. 575-579 (1988); U.S. Pat. Nos. 4,652,833; 4,409,331). In general, microcapsules differ from macrocapsules by (1) the complete exclusion of cells from the outer layer of the device, and (2) the thickness of the outer layer of the device. Typically, microcapsules have a volume on the order of 1 ml and contain fewer than $10^4$ cells. More specifically, microencapsulation encapsulates approximately 500-50,000 cells, generally, per capsule.

Capsules with a lower MWCO may be used to further prevent interaction of molecules of the patient's immune system with the encapsulated cells.

Any of the devices used in accordance with the methods described herein must provide, in at least one dimension, sufficiently close proximity of any isolated cells in the core to the surrounding eye tissues of the recipient in order to maintain the viability and function of the isolated cells. However, the diffusional limitations of the materials used to form the device do not in all cases solely prescribe its configurational limits. Certain additives can be used which alter or enhance the diffusional properties, or nutrient or oxygen transport properties, of the basic vehicle. For example, the internal medium of the core can be supplemented with oxygen-saturated perfluorocarbons, thus reducing the needs for immediate contact with blood-borne oxygen. This will allow isolated cells or tissues to remain viable while, for instance, a gradient of angiotensin is released from the vehicle into the surrounding tissues, stimulating ingrowth of capillaries. References and methods for use of perfluorocarbons are given by Faithful, N. S. Anaesthesia, 42, pp. 234-242 (1987) and NASA Tech Briefs MSC-21480, U.S. Govt. Printing Office, Washington, D.C. 20402, incorporated herein by reference. Alternatively for clonal cell lines such as PC 12 cells, genetically engineered hemoglobin sequences may be introduced into the cell lines to produce superior oxygen storage. See NPO-17517 NASA Tech Briefs, 15, p. 54.

The encapsulated cells can further be primed for enhanced secretion by environmental control and macronutrient and micronutrient supplementation. It is well known in the field of upstream development of recombinant cells that optimizing culture media, pH and temperature can have profound effects on cellular growth, density and recombinant protein output. Cells and ECT devices primed in such manner may increase productivity upon implantation into the host, allowing a prolonged enhanced productivity phenotype which may be useful for therapy. As examples, such nutrient compounds could be, but not limited to Tris, HEPES, glucose, sucrose, phospholipids, cholesterol, ascorbic acid, magnesium, sodium, vitamins, potassium, and calcium, cellular conditioned media, fetal calf serum, albumin, lecithin, sphingomyelin, lipoproteins, HDL, LDL, polyamines, ethanolamines, fibronectin, transferring, laminin, cholera toxins, hydrocortisone and other steroids, prostaglandins, insulin, EGF, FGF2 and other growth factors, dexamethasone, beta-mercaptoethanol and other reducing agents, and selenium. In addition, pre-formulated media may be used from commercial media suppliers such as Biowhittaker, Gibco/Invitrogen, Hyclone, JRH, Expression Systems, Sigma, PAA and Irvine Scientific.

The thickness of the device jacket should be sufficient to prevent an immunoresponse by the patient to the presence of the devices. For that purpose, the devices preferably have a minimum thickness of 1 µm or more and are free of the cells. Additionally, reinforcing structural elements can also be incorporated into the devices.

For example, these structural elements can be made in such a fashion that they are impermeable and are appropriately configured to allow tethering or suturing of the device to the eye tissues of the recipient. In certain circumstances, these elements can act to securely seal the jacket (e.g., at the ends of the cylinder), thereby completing isolation of the core materials (e.g., a molded thermoplastic clip). In many embodiments, it is desirable that these structural elements should not occlude a significant area of the permselective jacket.

The device of the present invention is of a sufficient size and durability for complete retrieval after implantation. One preferred device of the present invention has a core of a volume of approximately 1-3 uL. The internal geometry of micronized devices has a volume of approximately 0.05-0.1 uL.

Along with the anti-angiogenic antibody-scaffolds and/or soluble VEGF receptors described herein, at least one additional BAM can also be delivered from the device to the eye. For example, the at least one additional BAM can be provided from a cellular or a noncellular source. When the at least one additional BAM is provided from a noncellular source, the additional BAM(s) may be encapsulated in, dispersed within, or attached to one or more components of the cell system including, but not limited to: (a) sealant; (b) scaffold; (c) jacket membrane; (d) tether anchor; and/or (e) core media. In such embodiment, co-delivery of the BAM from a noncellular source may occur from the same device as the BAM from the cellular source.

Alternatively, two or more encapsulated cell systems can be used. For example, the least one additional biologically active molecule can be a nucleic acid, a nucleic acid fragment, a peptide, a polypeptide, a peptidomimetic, a carbohydrate, a lipid, an organic molecule, an inorganic molecule, a therapeutic agent, or any combinations thereof. Specifically, the therapeutic agents may be an anti-angiogenic drug, a steroidal and non-steroidal anti-inflammatory drug, an anti-mitotic drug, an anti-tumor drug, an anti-parasitic drug, an IOP reducer, a peptide drug, and/or any other biologically active molecule drugs approved for commercial use.

Suitable excipients include, but are not limited to, any non-degradable or biodegradable polymers, hydrogels, solubility enhancers, hydrophobic molecules, proteins, salts, or other complexing agents approved for formulations.

Non-cellular dosages can be varied by any suitable method known in the art such as varying the concentration of the therapeutic agent, and/or the number of devices per eye, and/or modifying the composition of the encapsulating excipient. Cellular dosage can be varied by changing (1) the number of cells per device, (2) the number of devices per eye, and/or (3) the level of BAM production per cell. Cellular production can be varied by changing, for example, the copy number of the gene for the BAM in the transduced cell, or the efficiency of the promoter driving expression of the BAM. Suitable dosages from cellular sources may range from about 1 pg to about 1000 mg per day.

The instant invention also relates to methods for making the macrocapsular devices described herein. Devices may be formed by any suitable method known in the art. (See, e.g., U.S. Pat. Nos. 6,361,771; 5,639,275; 5,653,975; 4,892,538; 5,156,844; 5,283,138; and 5,550,050, each of which is incorporated herein by reference).

Membranes used can also be tailored to control the diffusion of molecules, such as the anti-angiogenic antibody-scaffold or soluble VEGF receptor, based on their molecular weight. (See Lysaght et al., 56 J. Cell Biochem. 196 (1996), Colton, 14 Trends Biotechnol. 158 (1996)). Using encapsulation techniques, cells can be transplanted into a host without immune rejection, either with or without use of immunosuppressive drugs. The capsule can be made from a biocompatible material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics.

If a device with a jacket of thermoplastic or polymer membrane is desired, the pore size range and distribution can be determined by varying the solids content of the solution of precursor material (the casting solution), the chemical composition of the water-miscible solvent, or optionally including a hydrophilic or hydrophobic additive to the casting solution, as taught by U.S. Pat. No. 3,615,024. The pore size may also be adjusted by varying the hydrophobicity of the coagulant and/or of the bath.

Typically, the casting solution will comprise a polar organic solvent containing a dissolved, water-insoluble polymer or copolymer. This polymer or copolymer precipitates upon contact with a solvent-miscible aqueous phase, forming a permselective membrane at the site of interface. The size of pores in the membrane depends upon the rate of diffusion of the aqueous phase into the solvent phase; the hydrophilic or hydrophobic additives affect pore size by altering this rate of diffusion. As the aqueous phase diffuses farther into the solvent, the remainder of the polymer or copolymer is precipitated to form a trabecular support which confers mechanical strength to the finished device.

The external surface of the device is similarly determined by the conditions under which the dissolved polymer or copolymer is precipitated (i.e., exposed to the air, which generates an open, trabecular or sponge-like outer skin, immersed in an aqueous precipitation bath, which results in a smooth permselective membrane bilayer, or exposed to air saturated with water vapor, which results in an intermediate structure).

The surface texture of the device is dependent in part on whether the extrusion nozzle is positioned above, or immersed in, the bath: if the nozzle is placed above the surface of the bath a roughened outer skin will be formed, whereas if the nozzle is immersed in the bath a smooth external surface is formed.

The surrounding or peripheral matrix or membrane can be preformed, filled with the materials which will form the core (for instance, using a syringe), and subsequently sealed in such a manner that the core materials are completely enclosed. The device can then be exposed to conditions which bring about the formation of a core matrix if a matrix precursor material is present in the core.

The devices of the invention can provide for the implantation of diverse cell or tissue types, including fully-differentiated, anchorage-dependent, fetal or neonatal, or transformed, anchorage-independent cells or tissue. The cells to be isolated are prepared either from a donor (i.e., primary cells or tissues, including adult, neonatal, and fetal cells or tissues) or from cells which replicate in vitro (i.e., immortalized cells or cell lines, including genetically modified cells). In all cases, a sufficient quantity of cells to produce effective levels of the needed product or to supply an effective level of the needed metabolic function is prepared, generally under sterile conditions, and maintained appropriately (e.g. in a balanced salt solution such as Hank's salts, or in a nutrient medium, such as Ham's F12) prior to isolation.

The ECT devices of the invention are of a shape which tends to reduce the distance between the center of the device and the nearest portion of the jacket for purposes of permitting easy access of nutrients from the patient into the cell or of entry of the patient's proteins into the cell to be acted upon by the cell to provide a metabolic function. In that regard, a non-spherical shape, such as a cylinder, is preferred.

Four important factors that influence the number of cells or amount of tissue to be placed within the core of the device (i.e., loading density) of the instant invention are: (1) device size and geometry; (2) mitotic activity within the device; (3) viscosity requirements for core preparation and or loading; and (4) pre-implantation assay and qualification requirements.

With respect to the first of these factors, (device size and geometry), the diffusion of critical nutrients and metabolic requirements into the cells as well as diffusion of metabolites away from the cell are critical to the continued viability of the cells. In the case of RPE cells such as ARPE-19 cells, the neighboring cells are able to phagocytize the dying cells and use the debris as an energy source.

Among the metabolic requirements met by diffusion of substances into the device is the requirement for oxygen. The oxygen requirements of the specific cells must be determined for the cell of choice. See Methods and references for determination of oxygen metabolism are given in Wilson D. F. et al., J. Biol. Chem., 263, pp. 2712-2718, (1988).

With respect to the second factor (cell division), if the cells selected are expected to be actively dividing while in the device, then they will continue to divide until they fill the available space, or until phenomena such as contact inhibition limit further division. For replicating cells, the geometry and size of the device will be chosen so that complete filling of the device core will not lead to deprivation of critical nutrients due to diffusional limitations.

With respect to the third factor (viscosity of core materials) cells in densities occupying up to 70% of the device volume can be viable, but cell solutions in this concentration range would have considerable viscosity. Introduction of cells in a very viscous solution into the device could be prohibitively difficult. In general, for both two step and coextrusion strategies, cell loading densities of higher than 30% will seldom be useful, and in general optimal loading densities will be 20% and below. For example, for fragments of tissues, it is important, in order to preserve the viability of interior cells, to observe the same general guidelines as above and tissue fragments should not exceed 250 microns in diameter with the interior cells having less than 15, preferably less than 10 cells between them and the nearest diffusional surface.

Finally, with respect to the fourth factor (preimplantation and assay requirements), in many cases, a certain amount of time will be required between device preparation and implantation. For instance, it may be important to qualify the device in terms of its biological activity. Thus, in the case of mitotically active cells, preferred loading density will also consider the number of cells which must be present in order to perform the qualification assay.

In most cases, prior to implantation in vivo, it will be important to use in vitro assays to establish the efficacy of the BAM (e.g., the anti-angiogenic antibody-scaffold or the VEGF receptor or PDGF receptor) within the device. Devices can be constructed and analyzed using model systems in order to allow the determination of the efficacy of the vehicle on a per cell or unit volume basis.

Following these guidelines for device loading and for determination of device efficacy, the actual device size for implantation will then be determined by the amount of biological activity required for the particular application. The number of devices and device size should be sufficient to produce a therapeutic effect upon implantation and is determined by the amount of biological activity required for the particular application. In the case of secretory cells releasing therapeutic substances, standard dosage considerations and criteria known to the art will be used to determine the amount of secretory substance required. Factors to be considered include the size and weight of the recipient; the productivity or functional level of the cells; and, where appropriate, the normal productivity or metabolic activity of the organ or tissue whose function is being replaced or augmented. It is also important to consider that a fraction of the cells may not survive the immunoisolation and implantation procedures. Moreover, whether the recipient has a preexisting condition which can interfere with the efficacy of the implant must also be considered. Devices of the instant invention can easily be manufactured which contain many thousands of cells. For example, current ophthalmic clinical devices contain between 200,000 and 750,000 cells, whereas micronized devices would contain between 10,000 and 100,000 cells. Other large scale devices may contain between 1,000,000 to 100,000,000 cells.

Encapsulated cell therapy is based on the concept of isolating cells from the recipient host's immune system by surrounding the cells with a semipermeable biocompatible material before implantation within the host. For example, the invention includes a device in which genetically engineered ARPE-19 cells are encapsulated in an immunoisolatory capsule, which, upon implantation into a recipient host, minimizes the deleterious effects of the host's immune system on the ARPE-19 cells in the core of the device. ARPE-19 cells are immunoisolated from the host by enclosing them within implantable polymeric capsules formed by a microporous membrane. This approach prevents the cell-to-cell contact between the host and implanted tissues, thereby eliminating antigen recognition through direct presentation.

Any of the anti-angiogenic antibody-scaffolds or VEGF receptors or PDGF receptors described herein (alone or in any combination) can be delivered intraocularly (e.g., in the anterior chamber and the vitreous cavity), periocularly (e.g., within or beneath Tenon's capsule), or both. The devices of the invention may also be used to provide controlled and sustained release of the anti-angiogenic antibody-scaffolds or receptors to treat various ophthalmic disorders, ophthalmic diseases, and/or other diseases which have ocular effects.

Intraocular (preferably in the vitreous) or per ocular (preferably in the sub-Tenon's space or region) delivery of an anti-angiogenic factor, such as any of the anti-angiogenic antibody-scaffolds or soluble VEGF receptors described herein, in a dosage range of 0.1 pg and 1000 µg (e.g., between 0.1 pg and 500 mg; between 0.1 pg and 250 µg; between 0.1 pg and 100 µg; between 0.1 pg and 50 µg; between 0.1 pg and 25 µg; between 0.1 pg and 10 µg; between 0.1 pg and 5 µg; between 0.1 pg and 100 ng; between 0.1 pg and 50 ng; between 0.1 pg and 25 ng; between 0.1 pg and 10 ng; or between 0.1 pg and 5 ng) per eye per patient per day is contemplated. In one non-limiting example, the therapeutic amount is at least 0.5-50 µg/ml steady state in the eye. Suitable therapeutic amounts may include, for example, 0.5 ug, 0.6 ug, 0.7 ug, 0.8 ug, 0.9 ug, 1 ug, 2 ug, 3 ug, 4 ug, 5 ug, 6 ug, 7 ug, 8 ug, 9 ug, 10 ug, 11 ug, 12 ug, 13 ug, 14 ug, 15 ug, 16 ug, 17 ug, 18 ug, 19 ug, 20 ug, 21 ug, 22 ug, 23 ug, 24 ug, 25 ug, 26 ug, 27 ug, 28 ug, 29 ug, 30 ug, 31 ug, 32 ug, 33 ug, 34 ug, 35 ug, 36 ug, 37 ug, 38 ug, 39 ug, 40 ug, 41 ug, 42 ug, 43 ug, 44 ug, 45 ug, 46 ug, 47 ug, 48 ug, 49 ug, 50 ug, 51 ug, 52 ug, 53 ug, 54 ug, 55 ug, 56 ug, 57 ug, 58 ug, 59 ug, 60 ug, 61 ug, 62 ug, 63 ug, 64 ug, 65 ug, 66 ug, 67 ug, 68 ug, 69 ug, 70 ug, 71 ug, 72 ug, 73 ug, 74 ug, 75 ug, 76 ug, 77 ug, 78 ug, 79 ug, 80 ug, 81 ug, 82 ug, 83 ug, 84 ug, 85 ug, 86 ug, 87 ug, 88 ug, 89 ug, 90 ug, 91 ug, 92 ug, 93 ug, 94 ug, 95 ug, 96 ug, 97 ug, 98 ug, 99 ug, 100 ug, 150 ug, 200 ug, 250 ug, 300 ug, 350 ug, 400 ug, 450 ug, 500 ug, 550 ug, 600 ug, 650 ug, 700 ug, 750 ug, 800 ug, 850 ug, 900 ug, 950 ug, 1000 ug. Moreover, the cells lines and devices of the instant invention are able to express this therapeutic amount for a period of at least three months.

Ophthalmic disorders that may be treated by various embodiments of the present invention include, but are not limited to diabetic retinopathies, diabetic macular edema, proliferative retinopathies, retinal vascular diseases, vascular anomalies, age-related macular degeneration and other acquired disorders, endophthalmitis, infectious diseases, inflammatory but non-infectious diseases, AIDS-related disorders, ocular ischemia syndrome, pregnancy-related disorders, peripheral retinal degenerations, retinal degenerations, toxic retinopathies, retinal tumors, choroidal tumors, choroidal disorders, vitreous disorders, retinal detachment and proliferative vitreoretinopathy, non-penetrating trauma, penetrating trauma, post-cataract complications, and inflammatory optic neuropathies.

Those skilled in the art will recognized that age-related macular degeneration includes, but is not limited to, wet and dry age-related macular degeneration, exudative age-related macular degeneration, and myopic degeneration.

In some preferred embodiments, the disorder to be treated is the wet form of age-related macular degeneration or diabetic retinopathy. The present invention may also be useful for the treatment of ocular neovascularization, a condition associated with many ocular diseases and disorders. For example, retinal ischemia-associated ocular neovascularization is a major cause of blindness in diabetes and many other diseases.

The cell lines and devices of the present invention may also be used to treat ocular symptoms resulting from diseases or conditions that have both ocular and non-ocular symptoms. Some examples include cytomegalovirus retinitis in AIDS as well as other conditions and vitreous disorders; hypertensive changes in the retina as a result of pregnancy; and ocular effects of various infectious diseases such as tuberculosis, syphilis, Lyme disease, parasitic disease, toxocara canis, ophthalmonyiasis, cyst cercosis and fungal infections.

The devices and cell lines may also be used to treat conditions relating to other intraocular neovascularization-based diseases. For example, such neovascularization can occur in diseases such as diabetic retinopathy, central retinal vein occlusion and, possibly, age-related macular degeneration. Corneal neovascularization is a major problem because it interferes with vision and predisposes patients to corneal graft failure. A majority of severe visual loss is associated with disorders that result in ocular neovascularization.

The invention also relates to methods and the delivery of anti-angiogenic antibody-scaffold or soluble VEGF receptors or PDGF receptors in order to treat cell proliferative disorders, such as, for example, hematologic disorders, atherosclerosis, inflammation, increased vascular permeability, and malignancy within the ocular environment or outside at desired targeted locations within the body.

The use of the devices and techniques described herein provide several advantages over other delivery routes: the anti-angiogenic antibody-scaffolds or VEGF receptors or PDGF receptors can be delivered to the eye directly, which reduces or minimizes unwanted peripheral side effects and very small doses of the anti-angiogenic antibody-scaffold or receptor (i.e., nanogram or low microgram quantities rather than milligrams) can be delivered compared with topical applications, thereby also potentially lessening side effects. Moreover, since viable cells continuously produce newly synthesized anti-angiogenic antibody-scaffolds and receptors, these techniques should be superior to injection delivery of the anti-angiogenic antibody-scaffold or VEGF receptor, where the dose fluctuates greatly between injections and the anti-angiogenic antibody-scaffold or receptor is continuously degraded but not continuously replenished.

Living cells and cell lines genetically engineered to secrete the anti-angiogenic antibody-scaffolds or soluble VEGF receptors of the invention can be encapsulated in the device of the invention and surgically inserted (under retrobulbar anesthesia) into any appropriate anatomical structure of the eye. For example, the devices can be surgically inserted into the vitreous of the eye, where they are preferably tethered to the sclera to aid in removal. Devices can remain in the vitreous as long as necessary to achieve the desired prophylaxis or therapy. For example, the desired therapy may include promotion of neuron or photoreceptor survival or repair, or inhibition and/or reversal of retinal or choroidal neovascularization, as well as inhibition of uveal, retinal and optic nerve inflammation. With vitreal placement, the anti-angiogenic antibody-scaffold or VEGF receptor, may be delivered to the retina or the retinal pigment epithelium (RPE).

In other embodiments, cell-loaded devices are implanted periocularly, within or beneath the space known as Tenon's capsule, which is less invasive than implantation into the vitreous. Therefore, complications such as vitreal hemorrhage and/or retinal detachment are potentially eliminated. This route of administration also permits delivery of the anti-angiogenic antibody-scaffolds or soluble VEGF receptors or PDGF receptors described herein to the RPE or the retina. Periocular implantation is especially preferred for treating choroidal neovascularization and inflammation of the optic nerve and uveal tract. In general, delivery from periocular implantation sites will permit circulation of the anti-angiogenic antibody-scaffolds or soluble VEGF receptors to the choroidal vasculature, retinal vasculature, and the optic nerve.

Delivery of anti-angiogenic factors, such as the anti-angiogenic antibody-scaffolds or soluble VEGF receptors of the invention, directly to the choroidal vasculature (periocularly) or to the vitreous (intraocularly) using the devices and methods described herein may reduce or alleviate the problems associated with prior art treatment methods and devices and may permit the treatment of poorly defined or occult choroidal neovascularization as well as provide a way of reducing or preventing recurrent choroidal neovascularization via adjunctive or maintenance therapy.

Implantation of the biocompatible devices of the invention is performed under sterile conditions. The device can be implanted using a syringe or any other method known to those skilled in the art. Generally, the device is implanted at a site in the recipient's body which will allow appropriate delivery of the secreted product or function to the recipient and of nutrients to the implanted cells or tissue, and will also allow access to the device for retrieval and/or replacement. A number of different implantation sites are contemplated. These include, e.g., the aqueous humor, the vitreous humor, the sub-Tenon's capsule, the periocular space, and the anterior chamber. Preferably, for implant sites that are not immunologically privileged, such as periocular sites, and other areas outside the anterior chamber (aqueous) and the posterior chamber (vitreous), the capsules are immunoisolatory.

It is preferable to verify that the cells immobilized within the device function properly both before and after implantation. Any assays or diagnostic tests well known in the art can be used for these purposes. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them.

The use of many of the prior art devices and surgical techniques resulted in a large number of retinal detachments. The occurrence of this complication is lessened because the devices and methods of this invention are less invasive compared to several other therapies.

Modified, truncated and/or mutein forms of the anti-angiogenic antibody-scaffolds and VEGF receptors described herein can also be used in accordance with this invention. Further, the use of active fragments of these anti-angiogenic antibody-scaffolds or receptors (i.e., those fragments having biological activity sufficient to achieve a therapeutic effect) is also contemplated. Also contemplated are anti-angiogenic antibody-scaffolds or receptor molecules modified by attachment of one or more polyethylene glycol (PEG) or other repeating polymeric moieties as well as combinations of these proteins and polycistronic versions thereof.

Treatment of many conditions according to the methods described herein will require only one or at most less than 50 implanted devices per eye to supply an appropriate therapeutic dose. Therapeutic dosages may be between about 0.1 pg and 1000 µg per eye per patient per day (e.g., between 0.1 pg and 500 µg; between 0.1 pg and 250 µg, between 0.1 pg and 100 mg; between 0.1 pg and 50 µg; between 0.1 pg and 25 µg; between 0.1 pg and 10 µg; between 0.1 pg and 5 µg; between 0.1 pg and 100 ng; between 0.1 pg and 50 ng; between 0.1 pg and 25 ng; between 0.1 pg and 10 ng; or between 0.1 pg and 5 ng per eye per patient per day). In one non-limiting example, the therapeutic amount is at least 0.5-50 µg/ml steady state in the eye. Suitable therapeutic amounts may include, for example, 0.5 ug, 0.6 ug, 0.7 ug, 0.8 ug, 0.9 ug, 1 ug, 2 ug, 3 ug, 4 ug, 5 ug, 6 ug, 7 ug, 8 ug, 9 ug, 10 ug, 11 ug, 12 ug, 13 ug, 14 ug, 15 ug, 16 ug, 17 ug, 18 ug, 19 ug, 20 ug, 21 ug, 22 ug, 23 ug, 24 ug, 25 ug, 26 ug, 27 ug, 28 ug, 29 ug, 30 ug, 31 ug, 32 ug, 33 ug, 34 ug, 35 ug, 36 ug, 37 ug, 38 ug, 39 ug, 40 ug, 41 ug, 42 ug, 43 ug, 44 ug, 45 ug, 46 ug, 47 ug, 48 ug, 49 ug, 50 ug, 51 ug, 52 ug, 53 ug, 54 ug, 55 ug, 56 ug, 57 ug, 58 ug, 59 ug, 60 ug, 61 ug, 62 ug, 63 ug, 64 ug, 65 ug, 66 ug, 67 ug, 68 ug, 69 ug, 70 ug, 71 ug, 72 ug, 73 ug, 74 ug, 75 ug, 76 ug, 77 ug, 78 ug, 79 ug, 80 ug, 81 ug, 82 ug, 83 ug, 84 ug, 85 ug, 86 ug, 87 ug, 88 ug, 89 ug, 90 ug, 91 ug, 92 ug, 93 ug, 94 ug, 95 ug, 96 ug, 97 ug, 98 ug, 99 ug, 100 ug, 150 ug, 200 ug, 250 ug, 300 ug, 350 ug, 400 ug, 450 ug, 500 ug, 550 ug, 600 ug, 650 ug, 700 ug, 750 ug, 800 ug, 850 ug, 900 ug, 950 ug, 1000 ug. Moreover, the cells lines and devices of the instant invention are able to express this therapeutic amount for a period of at least three months.

Each of the ophthalmic devices of the present invention is capable of storing between about 1,000 and about 750,000 cells, in individual or cluster form, depending on their type.

The invention will be further described in the following examples, which do not limit the scope of the invention described in the claims.

EXAMPLES

Example 1

Cellular Sub-cloning

Various anti-angiogenic antibody-scaffolds and soluble VEGF receptors were expressed in NTC-200 cells. As described herein, the terms "NTC-200" and "ARPE-19 cells" are used interchangeably to described the preferred cell types that are genetically engineered to express the anti-angiogenic antibody-scaffolds and soluble VEGF and PDGF receptors of the invention.

To achieve secretion of the protein, the constructs contained either the native or IgSP murine immunoglobulin leader sequence, the latter of which was used previously to direct secretion of CNTF from NTC-200 cells. Nucleotide and amino acid sequences of intended proteins and corresponding nucleic acid sequences, are described herein as follows:
1) p834
2) p838
3) p876
4) p873
5) p874
6) p875
7) p915
8) p914
9) p916
10) p913
11) p917
12) p964
13) p963
14) p974
15) p978
16) p977

For the soluble VEGF receptors (e.g., p834, p838, and p873), gene fragments were amplified from sVEGFR1 (hFlt) or sVEGFR2 (hKDR) cDNA (GenBank Accession Nos. U01134 and AF063658, respectively) by PCR using oligonucleotide primer pairs specific for the desired product. The anti-angiogenic antibody-scaffolds described herein (e.g., p876, p874, p875, p895, p896, p913 and p897) were designed based on portions of the sequences of known anti-VEGF compounds such as Bevacizumab and Ranibizumab (Genentech). Amplified products were digested with the appropriate restriction endonuclease and ligated into Neurotech mammalian expression vector pCpGfree-vitro (InvivoGen), a schematic of which is shown in FIG. 1. pCpGfree-vitro is a commercially available vector completely devoid of CpG dinucleotides, as well as incorporating strategically placed S/MARS insulators, thus reducing the possibility of silencing or gene interaction. In addition, S/MARS sequences may assist in the chromosomal integration within the host genome. This design makes it less likely that the expression of the inserted gene will be silenced (turned off) by cellular machinery. In the comparisons with other expression vectors (pcDNA, pKan, pCI-Neo etc.), pCpGfree-vitro consistently generates stable, higher producing recombinant cell lines. pCpGfree-vitro vector system includes three forms of expression vectors differentiated by the presence of either neomycin, blasticidin, or hygromycin resistance genes. By subcloning identical cDNA sequences into each of the neomycin, blasticidin and hygromycin resistance based expression vectors, cell lines can be transfected iteratively, using different selection markers for each iteration. Such method allows for gene dose amplification without the need for generating DHFR strains typically found in CHO manufacturing cell lines.

Transformed recombinant clones were selected with blasticidin or neomycin (G418), or hygromycin and purified miniprep plasmid DNA was analyzed by restriction digestion and agarose gel electrophoresis analysis. All putative plasmid clones containing an appropriate insert were verified by automated dideoxy sequencing (GeneWiz, Edison, N.J.) followed by chromatogram assemblies using Vector NTI v10.0 sequence analysis software (Invitrogen Corp, Carlsbad, Calif.).

Example 2

Cell Line Construction

Verified plasmid clones were used to transfect NTC-200 cells to obtain stable polyclonal cell lines. Briefly, 200-300K cells, plated 18 hours previously, were transfected with 3.0 ug of plasmid DNA using 6.0 ul of Fugene 6 transfection reagent (Roche Applied Science, Indianapolis Ind.) according to the manufacturer's recommendations. Transfections were performed in 3.0 ml of DMEM/F12 with 10% FBS, Endothelial SFM or Optimem media (Invitrogen Corp, Carlsbad, Calif.). Twenty four to 48 hours later cells were either fed with fresh media containing 1.0 ug/ul of G418 or passaged to a T-25 tissue culture flask containing G418. Cell lines were passaged under selection for 14-21 days until normal growth resumed, after which time drug was removed and cells were allowed to recover (~1 week) prior to characterization.

These polyclonal cell lines were dispersed, and then seeded on dishes. After appropriate growth, hundreds to thousands of individual colonies could be discerned by microscopy, picked and clonally expanded. Subclone supernatants were analyzed by ELISA for recombinant molecule production and combined with cell number determination, allowed the generation of rank-ordered clonal productivity. Desirable clonal cell lines were selected for stability, productivity and in vivo biophysical characteristics in ECT device and biological output in animal studies.

Expression stability of the recombinant protein from these cell lines was measured over the course of several weeks using the Human sVEGF R1/Flt1 Quantikine ELISA Kit (R&D Systems, Minneapolis, Minn.) or a polyclonal anti-human IgG1 Fc ELISA (Neurotech). Briefly, 50K cells, previously plated into 12 well tissue culture plates in DMEM/F12 with 10% FBS, were washed twice in HBSS (Invitrogen Corp, Carlsbad, Calif.) then pulsed for 2 hours with 1.0 ml of Endothelial SFM (Invitrogen Corp, Carlsbad, Calif.). Pulse media was stored at −20 C and assayed within one week of collection as per the manufacturer's protocol.

Stable cell lines secreting protein encoded by the following anti-angiogenic antibody-scaffolds and truncated VEGF and PDGF receptors were successfully created:
1) p834
2) p838
3) p876
4) p873
5) p874
6) p875
7) p915
8) p914
9) p916
10) p913
11) p917
12) p964
13) p963
14) p974
15) p978
16) p977

Example 3

Cell Line Screening and Hit Determination

Figure 2:
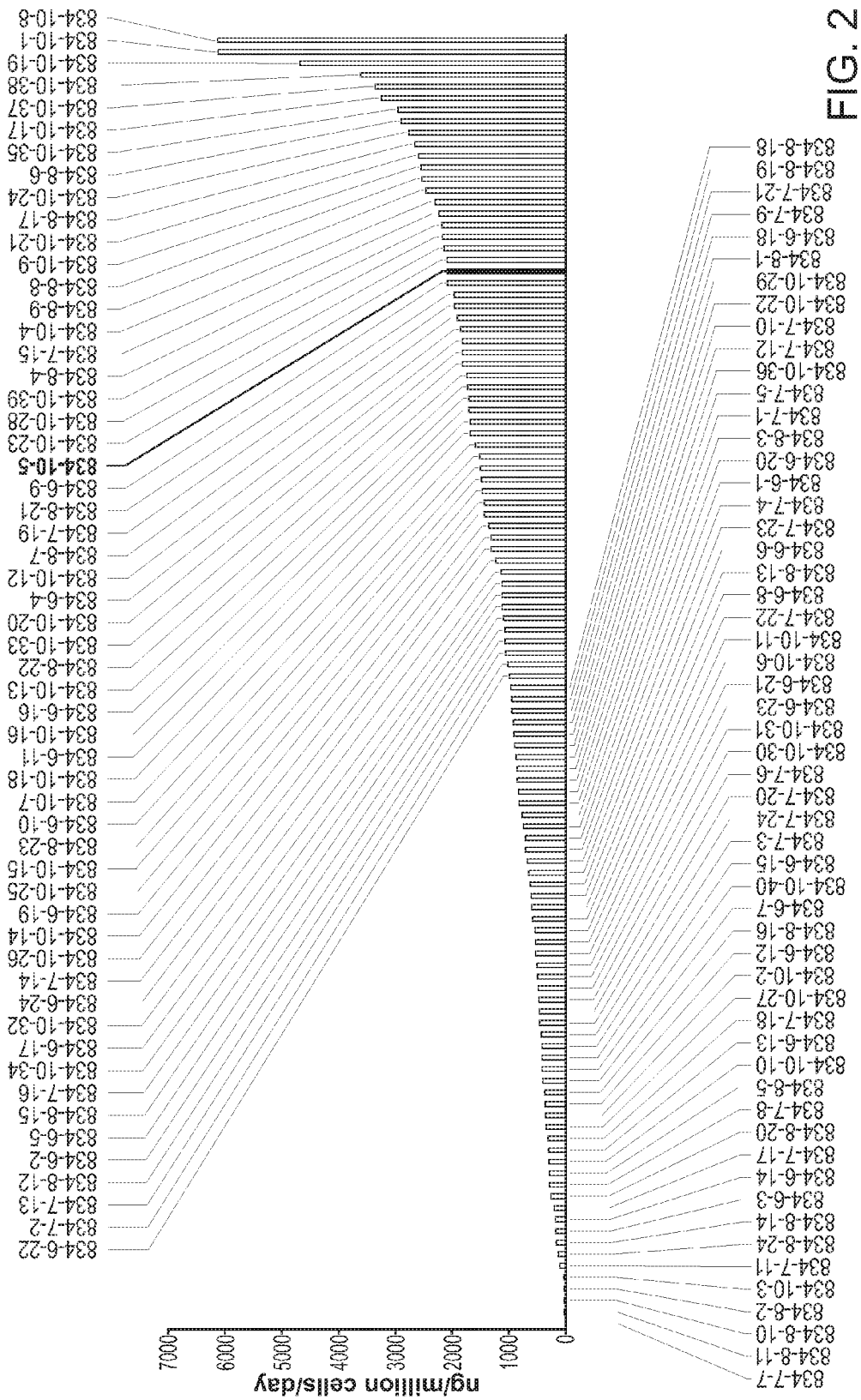
FIG. 2 shows an example of cell line screening and hit determination with cells expressing molecule p834.
Figure 2:
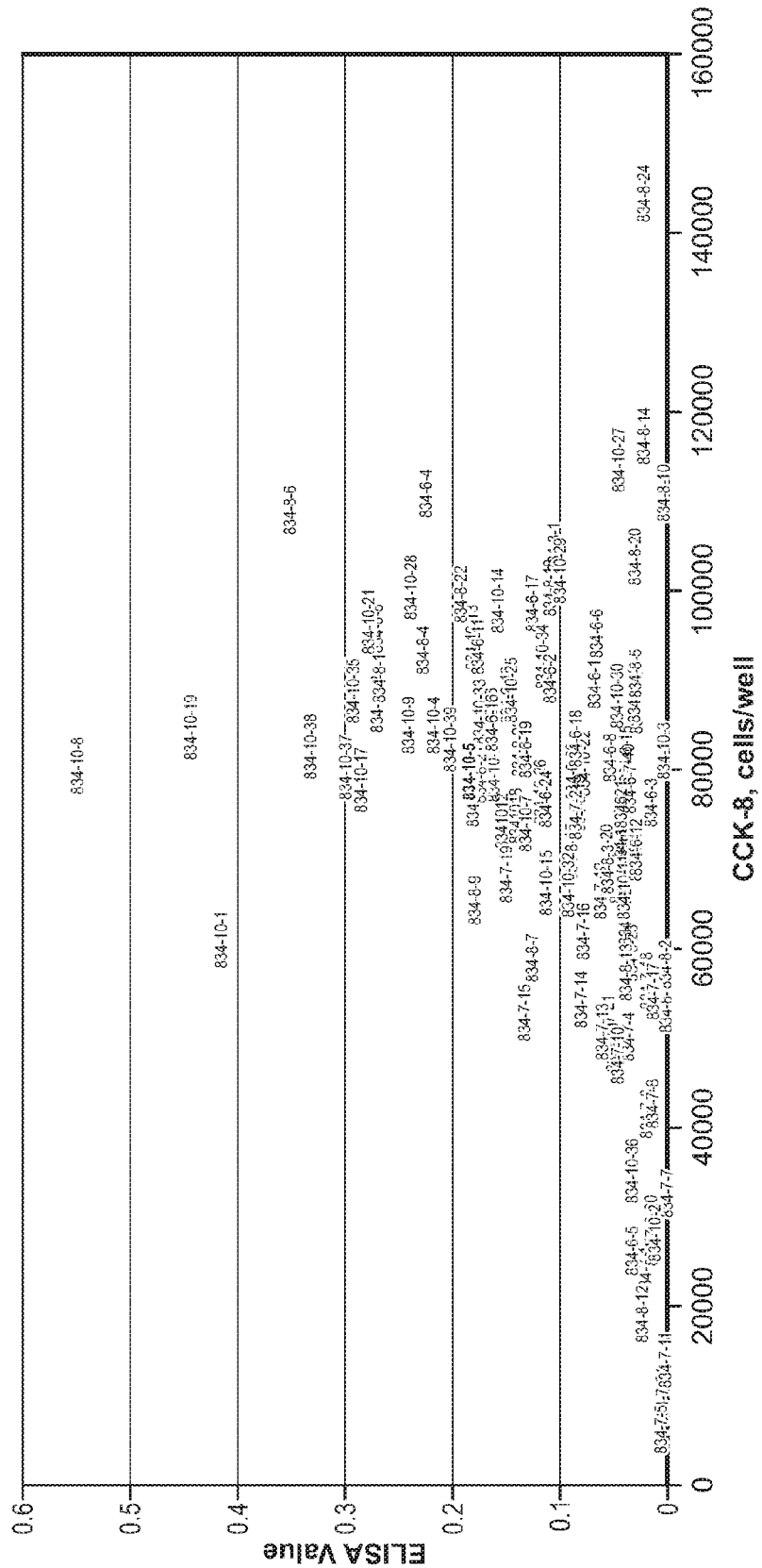

Recombinant NTC-200 cell lines expressing anti-angiogenic molecules were generated as described, one example of a screening selection is shown here for molecule p834, a VEGFR-Fc molecule. Anti-VEGFR ELISA assays were applied to clonal supernatants and cell counting kit 8 method (CCK-8, Dojindo Inc.) was used to enumerate cell number of the clone analyzed. In this Example, rank ordering of clones indicates that at least 8 clonal hits have productivity of greater than 10,000 ng/million cells/day (10 picogram/cell/day (pcd)) in this screening ELISA. In the scatter plot shown in FIG. 2, p834 subclones were plotted using ELISA output versus cell number, allowing the visualization of clonal lines that may exhibit growth and secretion properties beneficial for beneficial ECT scale-up propagation.

Current cell line production of 9 different antibody and receptor based Fc-molecules result in cell line outputs that are in the range of 7-20 pcd, as shown in Table 1. These levels are on par with output levels obtained by routine CHO line manufacturing processes. In each case, in addition to the top ranked clone for ECT, at least 5 independent subclones for each molecular entity were selected as back-up cell lines. The success of generating high producing antibody and receptor Fc based cell lines indicate that the NTC-200 cell line/pCpG expression system can be widely applied to biotherapeutic molecules, especially those represented by known CHO-manufactured products.

TABLE 1

Example Cell Line Outputs (picogram/cell/day)

| Construct | Example Cell Line | Type | Cell Line Output pcd |
|---|---|---|---|
| VEGFR-Fc #1 | 834-10-5 | Clonal | 10 |
| VEGFR-Fc #2 | 838-6-2 | Clonal | 10 |
| VEGFR-Fc #3 | 873-6-10 | Clonal | 7.8 |
| VEGFR-Fc #4 | 917-7 | Polyclonal | 8.5 |
| Antibody #1 | 874-1-23 | Clonal | 21 |
| Antibody #2 | 916-6 | Polyclonal | 23 |
| Antibody ScFv #1 | 876-9-3 | Clonal | 11.2 |
| Antibody ScFv #2 | 913-10 | Polyclonal | 8.3 |
| Antibody Fab | 915-6 | Polyclonal | 11.8 |

Example 4

Protein Characterization

Protein Expression

Figure 3:
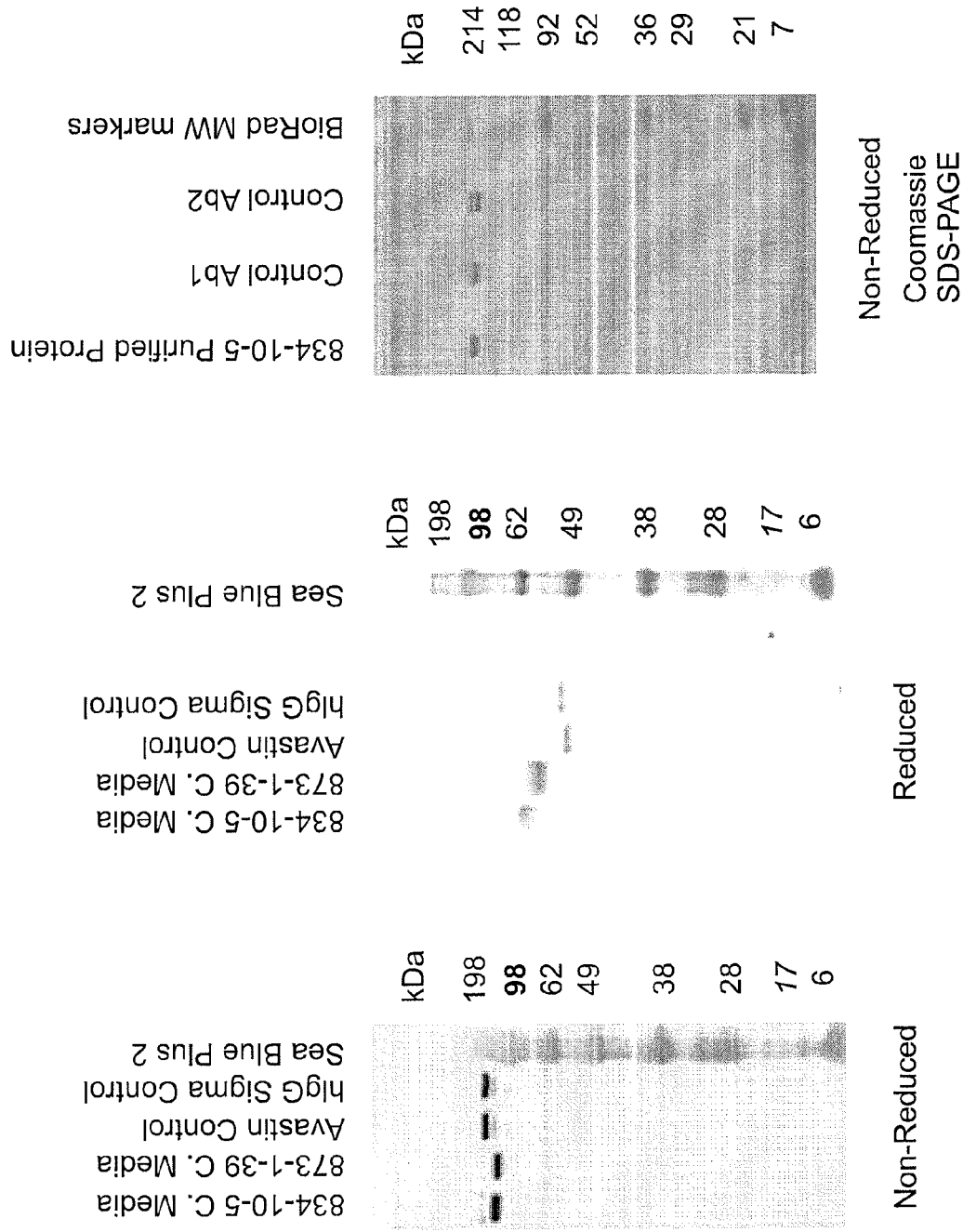
FIG. 3 shows the Western Blot results of molecules p834 and p873 and SDS-PAGE results of molecule p834.

The structure of p834 molecule is based on a chimeric VEGF-receptor 1 domain 2 and VEGF-receptor 2 domain 3 molecule fused in frame to a human IgG1 Fc domain. p834-10-5 protein in cell line conditioned media has a predicted dimeric molecular weight of 100 kDa (non-glycosylated) and an observed ~130 kDa (glycosylated) on non-reducing Western Blot. The predicted monomeric molecular weight of 834-10-5 is 50 kDa with an observed molecular weight of ~60 kDa (glycosylated) on reducing Western Blot. Protein G affinity purification of 834-10-5 cell line conditioned media reveal a single band under non-reducing SDS-PAGE, consistent with observed results in Western Blot analysis. High productivity of the 834-10-5 cell line was demonstrated by a yield of 15 mgs/liter hyperflask culture. (See FIG. 3).

HUVEC Bioassay

Figure 4:
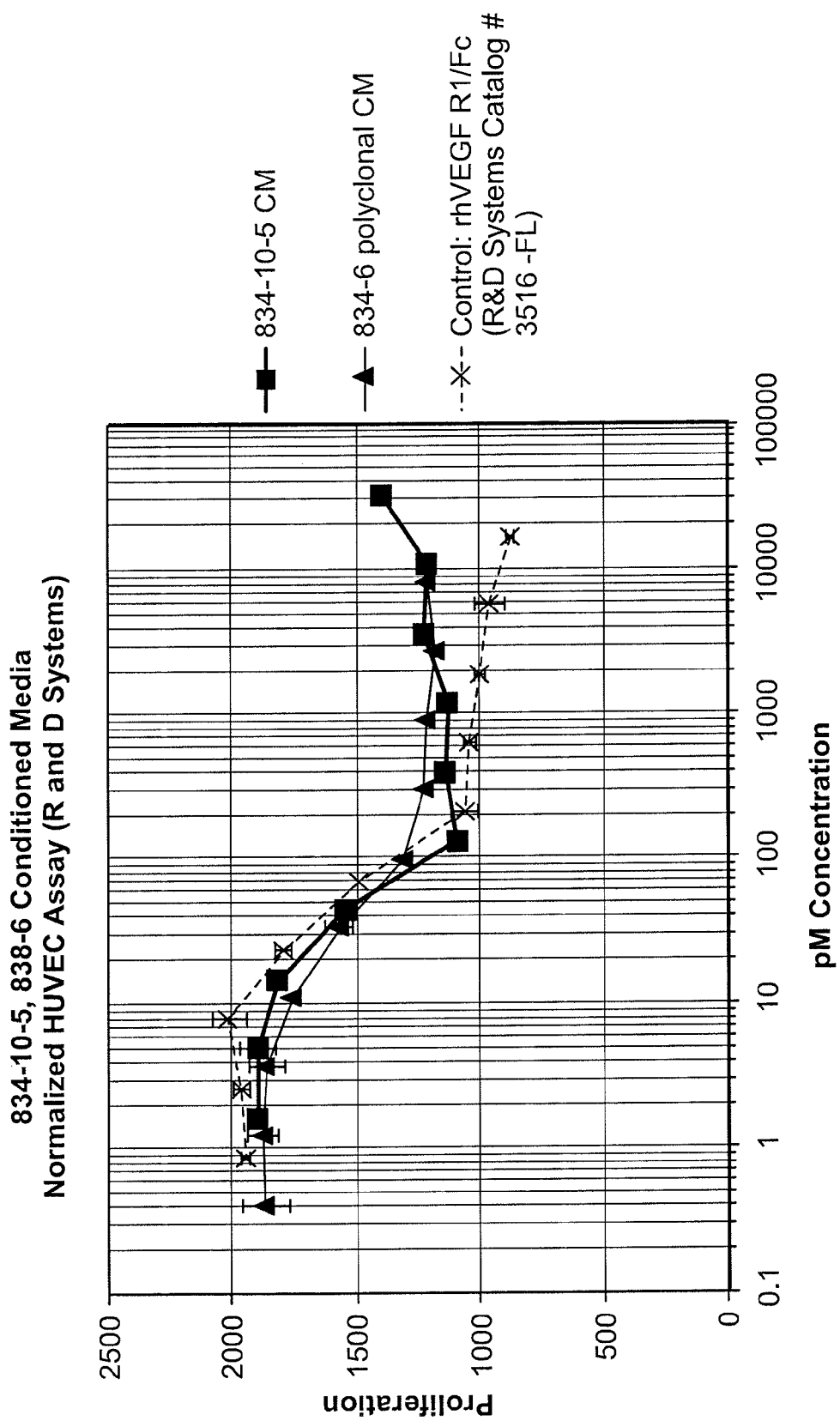
FIG. 4 shows the HUVEC bioassays of p834 and p838.

VEGF-A is known for its ability to stimulate proliferation of HUVEC cells in vitro. Thus a suitable bioassay for the measurement of VEGF-A inhibition would be the titration of an inhibitory molecule against a known amount of VEGF-A as a stimulator of HUVEC cells (R & D Systems). Conditioned media from p834-10-5 cell lines was harvested and serially diluted to inhibit VEGF-A stimulation of HUVEC cells. It was found that p834-10-5 conditioned media in this assay show EC50=~50 pM with 100% inhibition=~100 pM, as shown in FIG. 4. The p834-10-5 inhibitory activity is similar to the bioactivity of the VEGFR-Fc control (R & D systems), and also of the bioactivity of p838-6 polyclonal cell line conditioned media. In a summary, recombinant protein from these cell lines can efficiently inhibit endothelial cell proliferation similar to control protein (VR1D1-3-Fc). However, the conditioned media from mock transfected parental cells (WT) did not inhibit HUVEC growth.

Solution Binding Assay

Solution binding studies of VEGF using conditioned media from transfected cell lines were performed. Briefly, titrated amounts of conditioned media were incubated overnight at room temperature in the presence of VEGF. Free VEGF was measured using a sensitive EIA (R&D Systems, Minneapolis, Minn.) and non-linear regression analysis was performed (GraphPad Software Inc., San Diego, Calif.).

Figure 5:
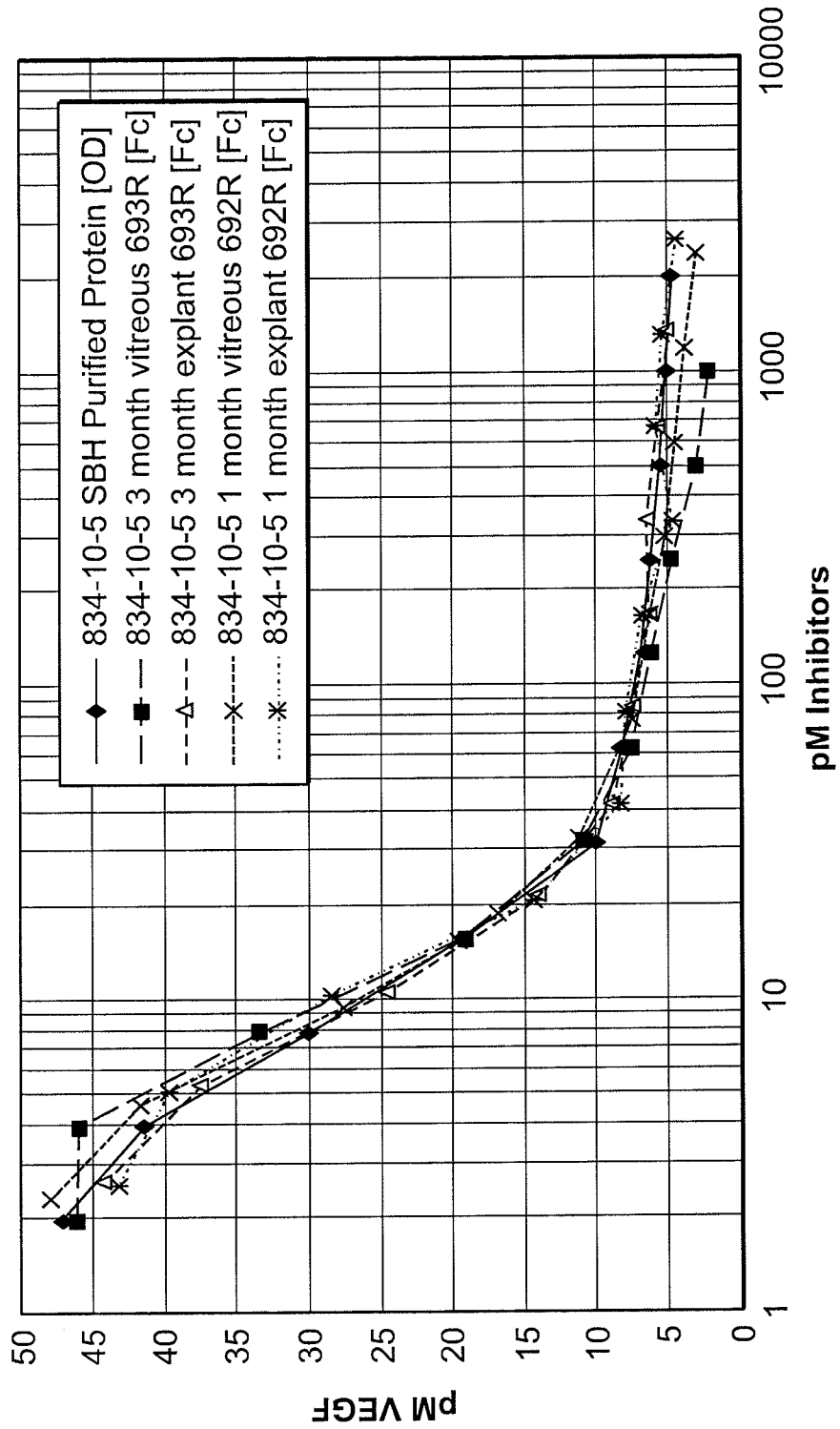
FIG. 5 shows the solution binding assay of p834.

The binding activity of recombinant molecules from p834-10-5 ECT was biophysically verified by the ability of the p834-10-5 ECT vitreal and explant condition media samples to inhibit or interfere with the reactivity of a commercial VEGF sandwich ELISA (R&D systems). As shown in FIG. 5, p834-10-5 samples show IC50=~12 pM while >90% inhibition is observed at ~100 pM. This inhibitory activity was detected from purified protein, from non-immunosuppressed rabbit vitreous containing p834-10-5 ECT devices (1 or 3 months time point), or from secreted proteins produced by explanted p834-10-5 ECT devices from rabbits. As a negative control, it was shown that conditioned media from mock transfected parental cells (WT) did not bind VEGF.

Example 5

Device Characterization and Implantation Results

Cell Line Stability Studies

Figure 6:
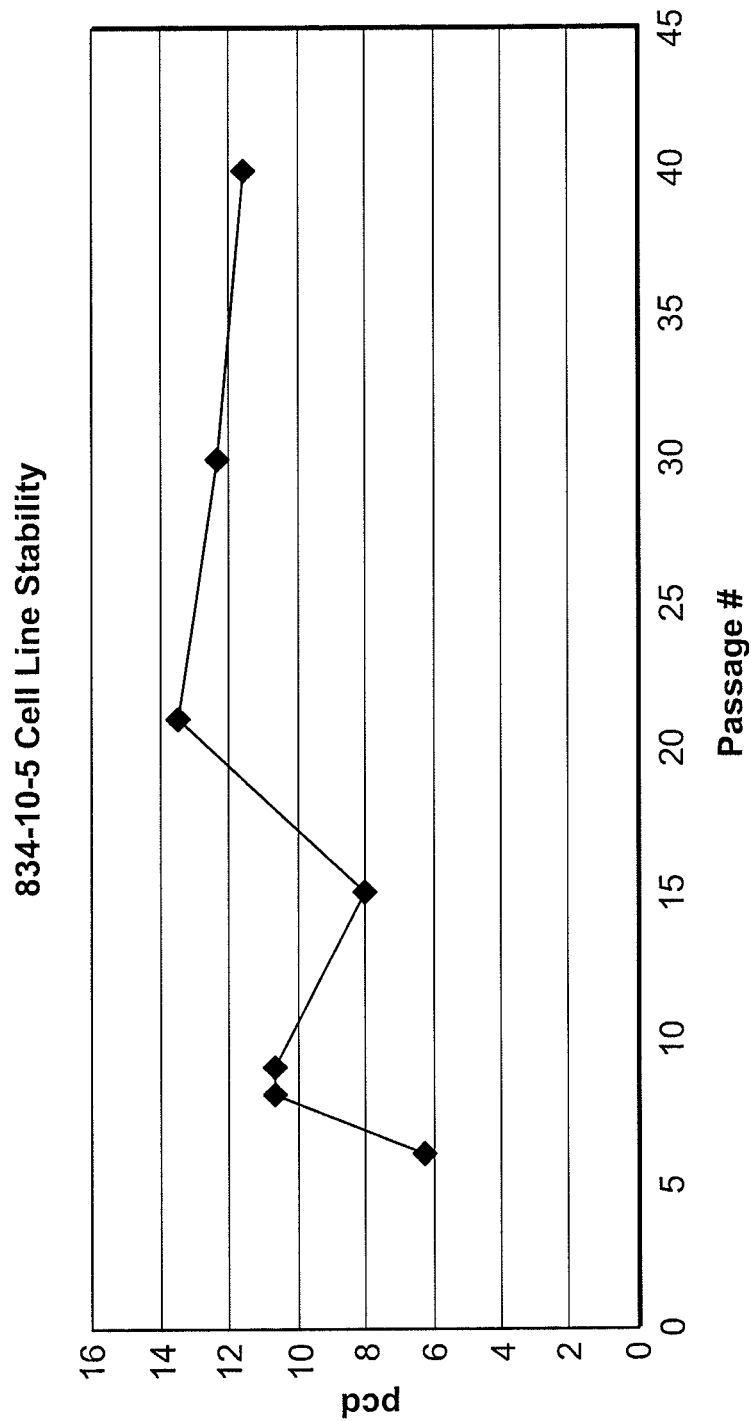
FIG. 6 shows the stability of the cell line expressing p834.

One criterion for manufacturability of recombinant cell lines is the limit of productivity by clonal expansion. It was calculated that growth and productivity analysis of 40 generations of clonal cells would confirm output stability, and supply sufficient information for the creation of a master cell bank (by passage ~17) and a working cell bank (by passage ~23). One working cell bank is calculated to be sufficient for the manufacture of at least 100,000,000 devices. Serial passage of p834-10-5 cell line revealed stability out to 40 generations in tissue culture with an average output of 10.4 pcd (picogram/cell/day) over the set of time points assayed. (See FIG. 6).

Figure 7:
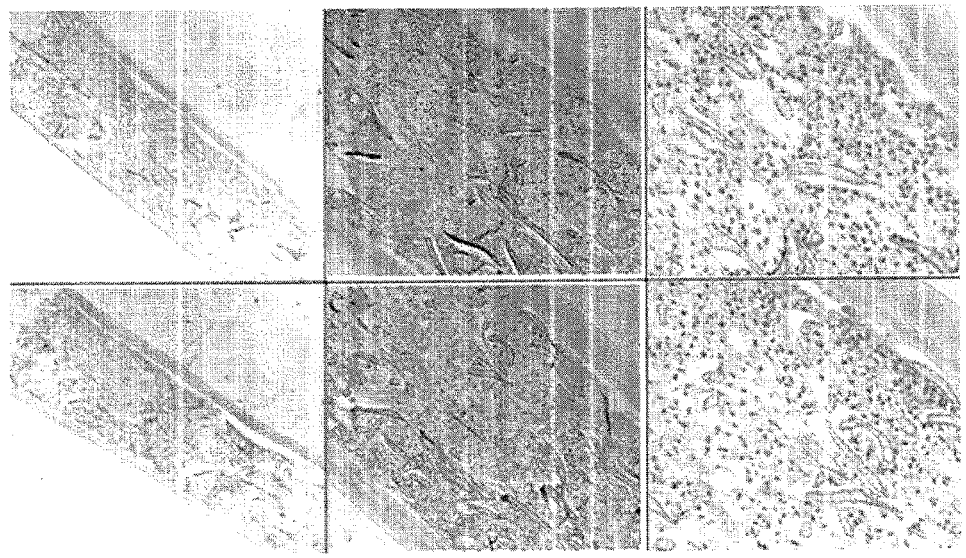
FIG. 7 shows the histological sections of p834 ECT device after 4 weeks held in a container.

Device Output Timecourse Studies p834-10-5 cell lines were expanded from a research cell bank aliquot and expanded prior to device filling. Cells were encapsulated by injection into 6 mm ECT devices with walls constructed with polysulfone semipermeable membranes and filled with polyethylene terephthalate (PET) yarn for cellular attachment. Devices were individually placed into primary packaging of sealed containers with nutrient media and incubated at 37 C for 10 weeks. During the time course of incubation hold, recombinant protein output was periodically surveyed from ECT devices by removal from packaging and assay for p834-10-5 protein secretion by ELISA. Results show an initial device output of 480 ng/device/day of p834-10-5 protein, gradually tapering off to a baseline output of ~60 ng/device/day after 6 weeks. In FIG. 7, histological sections of two devices reveal robust 834-10-5 cell growth internally, demonstrating high viability through one month device culture Devices containing ARPE-19 cells genetically engineered to secrete the p838 and p834 VEGFR constructs showed excellent safety profiles at 1 and 3 months post implant. Moreover, these devices ("the NT-503 devices") are stable in vivo at 1 and 3 months post implant.

Table 2 shows the PK data for these NT-503 devices:

TABLE 2

| NT-503 PK | | |
|---|---|---|
| Cell Line | Device Output (ng/day) | Vitreous Levels (ng/ml) |
| p838 (3-week Held) | | |
| 1-month | 38 ± 10.2 | 63 ± 5.3 |
| 3-month | 27 ± 7.4 | 34 ± 2.8 |
| p834 (4-week Held) | | |
| 1-month | 439 ± 127 | 803 ± 107 |
| 3-month | 300 ± 54 | 350 ± 111 |

Table 3 shows the results of the NT-503 device shelf stability:

TABLE 3

| NT-503 Shelf-Life: in vivo Stability Demonstrated 4-Week Shelf-Life | | | | |
|---|---|---|---|---|
| Cell Line | In vitro Held (Weeks) | Pre-implant (ng/day) | Explant 1 month in vivo (ng/day) | Vitreous 1 month in vivo (ng/ml) |
| p838 | 1 Week | 139 | 61 | 120 |
|  | 3 Week | 30 | 71 | 40 |
| p834 | 1 Week | 478 | 345 | 644 |
|  | 4 Week | 74 | 501 | 518 |

As shown above, the p834 device delivered a 13-fold higher level of VEGF receptors compared to p838. Regardless, both in vitro device output and in vivo performance (as measured for vitreous levels) were maintained stable for the NT-503. Moreover, an evaluation of in vitro hold periods and corresponding in vivo performance of implanted NT-503 devices have demonstrated a shelf life stability of up to 4 weeks duration.

Therefore, the p834 devices will be utilized in an on-going human clinical trial to ensure successful proof of concept in humans. Moreover, additional work will be done to select higher producing p838 clones for the second cohort of this clinical trial (the current p838 cell line is a polyclonal cell line).

Finally, if possible, continued efforts will be made to extend the shelf-life of the NT-503 devices beyond 4 weeks. However, this is currently not necessary as most cell therapy products used in the art have a shelf-life of 1 week.

Example 6

Animal Studies

At four weeks after packaging, devices were implanted into non-immunosuppressed New Zealand White rabbit eyes. To determine p834-10-5 output after one month and three month after implantation, animals were enucleated and concentrations of p834-10-5 were quantified from extracted vitreous and compared with explanted device productivity. At one month after implantation, explanted devices produced p834-10-5 protein at greater than 100 ng/ml/day with steady-state vitreous concentrations at greater than 250 ng/ml. At three months after implantation, explanted devices continued production at over 200 ng/ml while vitreous concentration were detected at over 700 ng/ml. (See Table 4). After one year, rabbits vitreous samples contained 350 ng/ml p834-10-5 protein, demonstrating continued production of recombinant receptor over the course of 12 months.

Figure 8:
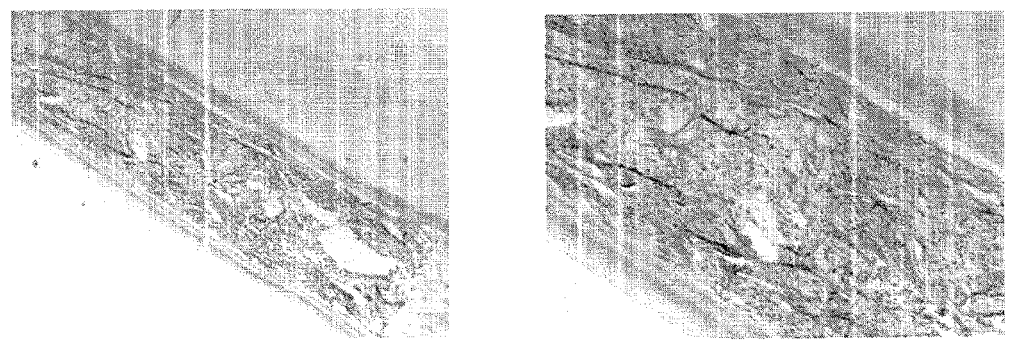
FIG. 8 shows the histology of explanted p834 ECT device after three months implantation into New Zealand white rabbit eyes.

As shown in FIG. 8, histology of explanted devices after three months implantation revealed robust cell growth, analogous to the cellular morphology observed in sample from container-held devices shown in FIG. 7. No clinically significant adverse events were observed within the eye of the treated rabbits during the study, as periodically examined by a veterinary ophthalmologist.

TABLE 4

| In vivo production of p834 | | |
|---|---|---|
| Sample Identifier | 1 Month Device Output (ng/day) | 1 Month Vitreous Levels (ng/ml) |
| Eye #1 | 250 | 760 |
| Eye #2 | 500 | 700 |

TABLE 4-continued

In vivo production of p834

| | | |
|---|---|---|
| Eye #3 | 482 | 800 |
| Eye #4 | 525 | 950 |

| | 3 Month Device Output (ng/day) | 3 Month Vitreous Levels (ng/ml) |
|---|---|---|
| Eye #5 | 350 | 200 |
| Eye #6 | 270 | 400 |
| Eye #7 | 340 | 340 |
| Eye #8 | 240 | 460 |

Example 7

Iterative Gene Dosing Increases Recombinant Protein Production

Figure 9:
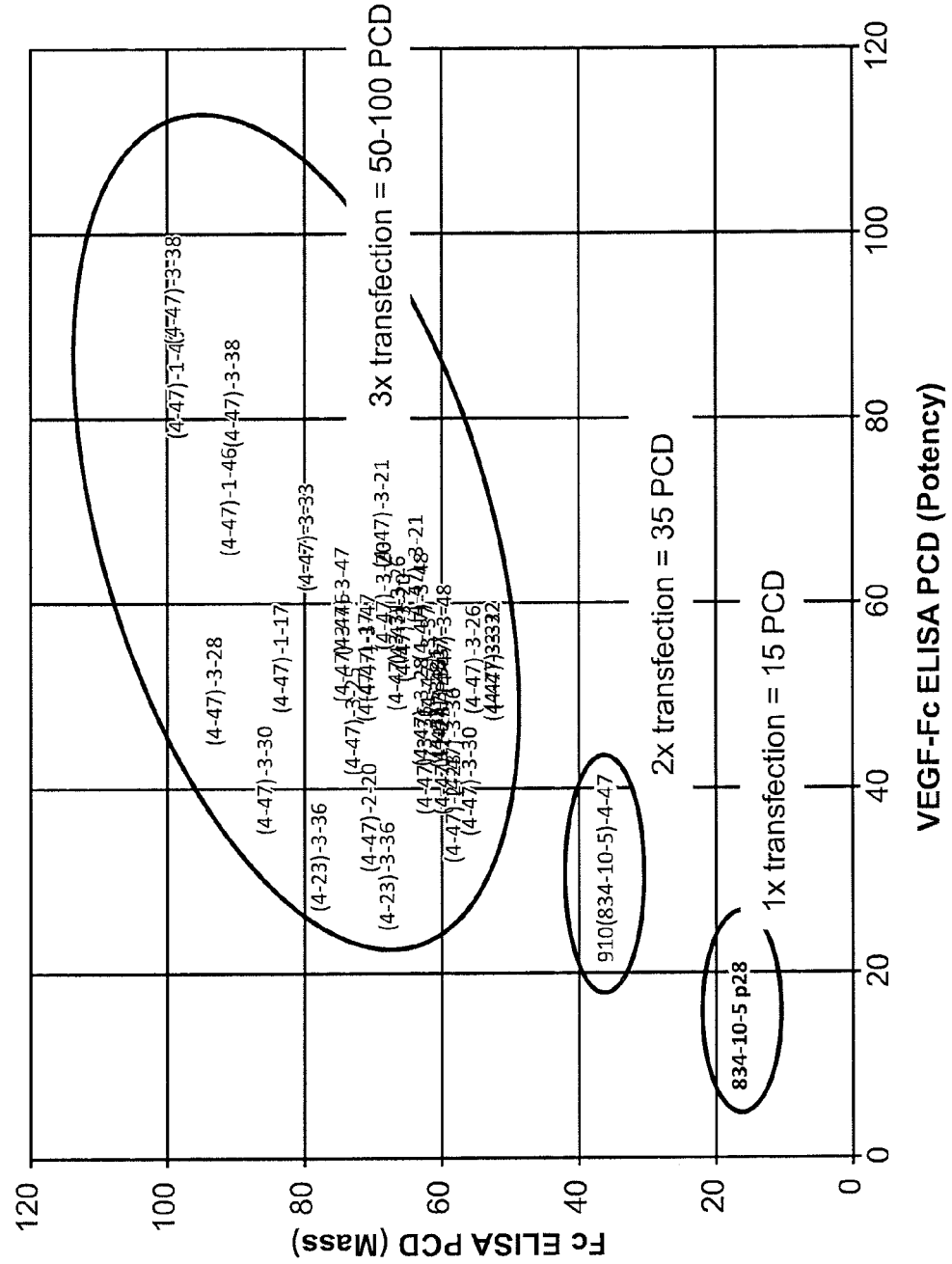
FIG. 9 shows PCD of cell lines producing 834 protein, on a mass versus potency plot. First, second and third transfection/iteration cell lines are plotted.

An iterative transfection was used to increase gene dosage, in particular of p834 cDNA. Three expression plasmids having identical 834 cDNA were produced: p834 pCpG vitro free (blasticidin resistant), p910 pCpG vitro free (neomycin resistant) and p969 pCpG vitro free (hygromycin resistant). p910 was transfected into blasticidin resistant p834-10-5 cell lines and resultant double integrant clones were recovered by application of neomycin selection, Subclones were isolated that exceeded PCD output levels of p834-10-5. As shown in FIG. 9, initial one time ("1×") transfection yielded the aforementioned p834-10-5 cell line with naked cell output levels (Fc ELISA) at 15-20 PCD. Transfection and selection of p910 clones from parental 834-10-5 clones yielded 910 (834-10-5)-4-47 clones with output levels 35-40 PCD. Iterative transfection and selection of p969 into the 910 (834-10-5)-4-47 subclone yielded numerous hygromycin resistant p969 derived clones, with initial isolates secreting levels of recombinant protein ranging from 50 PCD to >100 PCD. Maintenance of expression from all three genetic integration events was confirmed by culture of 969 clonal lines in each of blasticidin, hygromycin, and neomycin culture medias. Triple transfection clones were present that demonstrated minimal loss in potency as determined by ELISA assays, based on direct binding of recombinant protein to plate bound VEGF followed by detection using anti-human Fc. Surprisingly, up to 8 fold higher values of recombinant protein was detected than simple arithmetic addition of gene dosage based on 3× transfection, suggesting that an unexpected, synergistic biological selection is involved with increasing gene dosage by serial transfection (e.g., using an iterative transfection process).

Example 8

Preclinical Studies of Dose Escalation by Iteratively Transfected Cell Lines

Following the method in Example 6, the double transfectant cell line 910(834-10-5)-4-47, and triple transfectant cell line 969(910(834-10-5)-4-47)-33, was used to generate ECT devices, and subsequently implanted into rabbits. After one month of implantation, rabbits were enucleated and vitreous were extracted to quantitate levels of 834 protein. Simultaneously, devices were surgically removed, and the explanted devices were further cultured in cell growth media to ascertain the device productivity of recombinant protein. As shown in Table 5, output from 910 and 969-devices resulted in the steady state vitreous levels of 834 protein at levels nearly 5 and 10-fold greater, respectively, than those observed with 834 single transfected protein (Table 5). Consistent with the cell line PCD output data, a higher steady state concentration of 834 protein was observed in vivo than expected by simple additive effect of serial transfected gene dose, (Table 6 vs. Table 4) again suggesting an unexpected, synergistic biological selection of synergistic secretion enhancement due to the iterative transfection methodology.

TABLE 5 in vivo production of p834 protein by 910(834-10-5)-4-47 devices

| Sample Identifier | 1 Month Device Output (ng/day) | 1 Month Vitreous (ng/ml) |
|---|---|---|
| Eye # 9 | 1432 | 3641 |
| Eye # 10 | 2135 | 5572 |
| Eye # 11 | 2433 | 2710 |
| Eye # 12 | 1844 | 3603 |

TABLE 6 in vivo production of p834 protein by 969[910(834-10-5)-4-47]

| Sample Identifier | 1 Month Device Output (ng/day) | 1 Month Vitreous Levels (ng/ml) |
|---|---|---|
| Eye #13 | 2511 | 9390 |
| Eye #14 | 3819 | 16031 |
| Eye #15 | 2055 | 7115 |
| Eye #16 | 2691 | 5680 |
| Eye #17 | 2145 | 10968 |
| Eye #18 | 2464 | 10840 |

Example 9

Transfections of p544 (CNTF) Applied to 834-10-5 Cell Line

In one embodiment of sequential DNA transfection, expression vectors encoding unrelated (i.e., different) cDNAs may be used to generate cell lines secreting two different protein with differing functions. A CNTF expressing vector p544, encoding ciliary neurotrophic factor, a cytokine with neuroprotective effects in the retina of retinitis pigmentosa and geographic atrophy patients, was transfected into 834-10-5 cell lines. Transfected cells were selected against antibiotic, and the highest producing cell lines were recovered that produced CNTF and 834 protein, based on respective ELISA assays. Using iterative transfection, a number of CNTF/834 positive clones were obtained and described in Table 6.

Interestingly, within these top producing clones, no loss of production was observed based on parental 834-10-5 clones or by p544 derived CNTF expression, as compared to historic CNTF cell line controls (~0.5 pcd) demonstrating the potential of combination therapy by encapsulation of dual expressing cell lines, without loss of production fidelity as compared to parental expression levels. These results show that ECT therapies are not limited to the production of a single molecular entity, and that cell lines can be generated that secrete multiple therapeutic molecules. In this instance, CNTF functions as a neuroprotective therapy against dry AMD and VEGF antagonist functions as an anti-angiogenic therapy against wet AMD.

The p544 nucleic acid and amino acid sequences are provided below:

p544 CNTF (with genomic intron)
(SEQ ID NO: 33)

```
atgaaatgcagctgggttatcttcttcctgatggcagtggttacaggtaaggggctcccaagtc
ccaaacttgagggtccataaactctgtgacagtggcaatcactttgcctttctttctacagggg
tgaattcggctttcacagagcattcaccgctgacccctcaccgtcgggacctctgtagccgctc
tatctggctagcaaggaagattcgttcagacctgactgctcttacggaatcctatgtaagttgc
ctattttgctgttatctgttttcccttcatctttttgatccagcaacttaccatcacgcatca
gctccattaccaattgtgaaagctctaatcatatagtcattcatataggttatttgacatgggc
ccttcccttgaggaaacccatgtgactttattttcttcctctgggctgtttaggagatgaagtt
acttgaatgagaaatatatatggagttctagaaaggattggtttatatgtcttggaggctatt
ccaaatttattggcatatattctgaatactactagaacagattagccatgggccctctgggttc
ttcatagccattgttctgaattttttagctatgtaaatgaaaggtttatgggataggaagagta
ctatgaacgtgggaggaatttgtaaatcctaccaatttctcctatatagcattagccacccacc
ttttagtattctgcatcaaaagtagattgtgtctaaagagaaaggtaagctatcaaaaggatct
cctagaagattcattggaaacttgtggaagtgtcaaattcttgagctaattctggagttccaga
tttgtcttctaacagtaaggggatccccatcaatttccacctgagatatgctgtggaaatactc
caaccccctgtggagagttttgaatttaggctgagaactgatttatctttgtacagcctcaccag
acagaaatcagactctttgggagtgctcaatggggagagggaagttagagaaattctacaatgg
ctatattccaagttttcctagttgtggccagtgtcttttacaagtatgtttaaaaatactttaa
tatgattaaaatattccagttaatgagagagtttgaagtgagaaggaaaaattcttctaaatca
gttttcaacctttagaactcaataaaatctgaacattcttctaagaaaaatccataggtagtca
atttcaggcagtattgggtctttctaaagtccagtcatagagcccaaattaagagttcctactg
tagacatattatttactttacaacttggatccttggccagagagatgagtgagattttgtatga
aatttaggggtgatttaaggacactggggtgatgacagaagatgtggtgttttcctgtatcctc
ggccaggtgaagcatcagggcctgaacaagaacatcaacctggactctgcggatgggatgccag
tggcaagcactgatcagtggagtgagctgaccgaggcagagcgactccaagagaaccttcaagc
ttatcgtaccttccatgttttgttggccaggctcttagaagaccagcaggtgcattttacccca
accgaaggtgacttccatcaagctatacataccttcttctccaagtcgctgcctttgcatacc
agatagaggagttaatgatactcctggaatacaagatccccgcaatgaggctgatgggatgcc
tattaatgttggagatggtggtctctttgagaagaagctgtggggcctaaaggtgctgcaggag
cttcacagtggacagtaaggtccatccatgaccttcgtttcatttcttctcatcagactggga
tcccagcacgtgggagccattatattgctaacaacaagaaaatgtag
```

Spliced, translated p544, including signal peptide
(SEQ ID NO: 34)

```
mkcswvifflmavvtgvnsaftehspltphrrdlcsrsiwlarkirsdltaltesyvkhqglnk
ninldsadgmpvastdqwselteaerlgenlqayrtfhvllarlledqqvhftptegdfhqaih
tillqvaafayqieelmilleykiprneadgmpinvgdgglfekklwglkvlqelsqwtvrsih
dlrfisshqtgipargshyiannkkm
```

TABLE 7

544 CNTF and 834 protein production from cell lines derived from iterative transfections.

| Cell Line | CNTF PCD | 834 PCD |
|---|---|---|
| 544(834-10-5) - 1 - 1 | 0.200 | 15.02 |
| 544(834-10-5) - 1 - 3 | 0.594 | 21.14 |
| 544(834-10-5) - 1 - 9 | 0.410 | 15.32 |
| 544(834-10-5) - 1 - 35 | 0.401 | 14.57 |
| 544(834-10-5) - 1 - 38 | 0.457 | 18.62 |
| 544(834-10-5) - 1 - 41 | 0.380 | 14.12 |
| 544(834-10-5) - 1 - 44 | 0.360 | 14.47 |
| 544(834-10-5) - 1 - 46 | 0.424 | 15.98 |

Example 10

Soluble PDGFR antagonists

Figure 10:
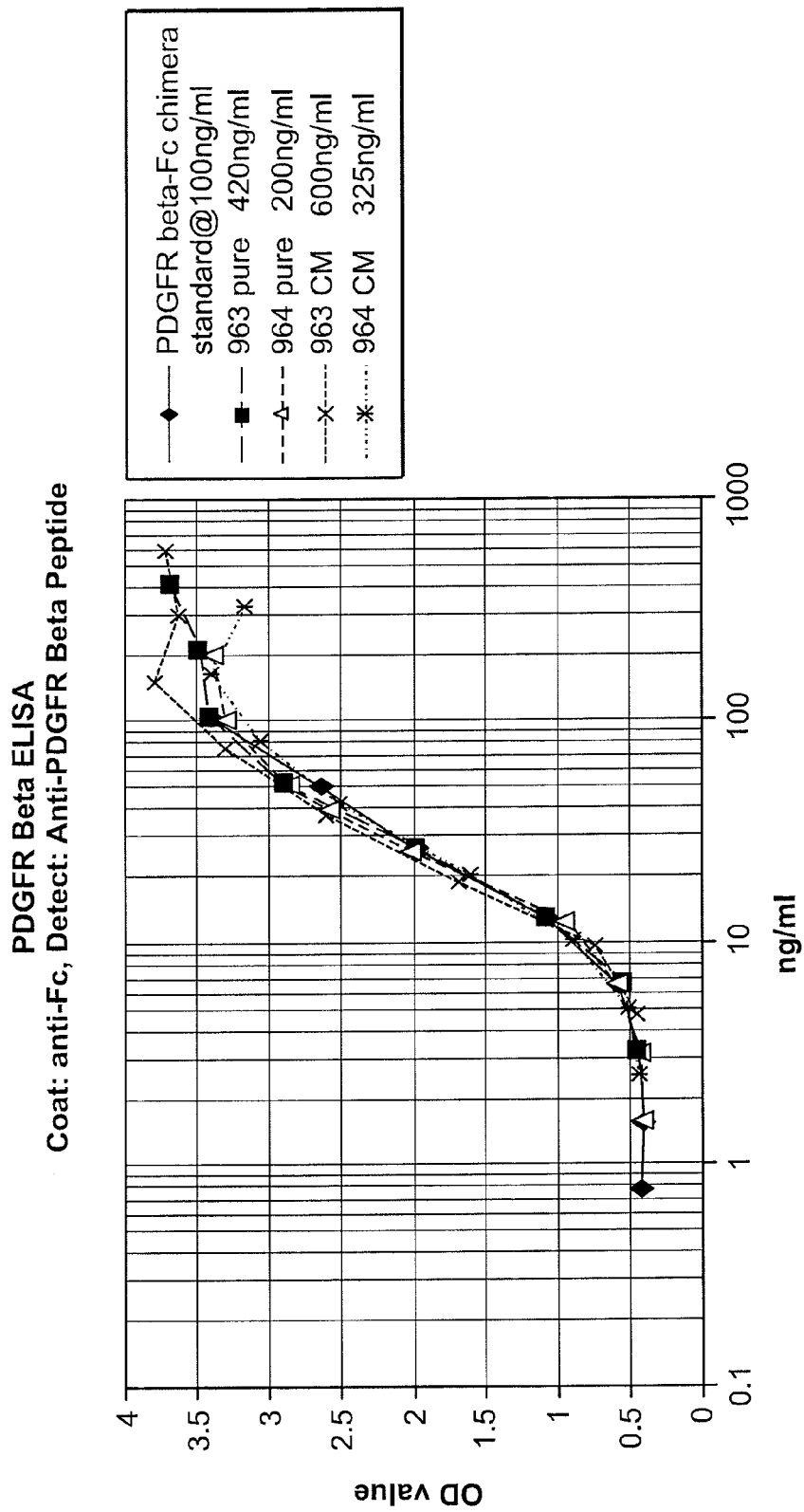
FIG. 10 shows detection ELISA of PDGFR Beta Fc fusion proteins as produced by cells transfected by p963 and p964.
Figure 11:
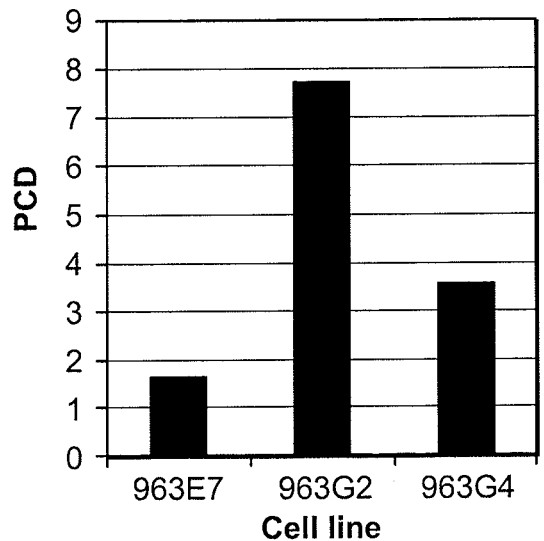
FIG. 11 shows example clonal cell lines producing PDGFR-D1-D5-hIgG1 Fc.

A dual molecule combinatorial ECT therapy may be targeted at angiogenesis, for example by dual devices secreting separate anti-angiogenic factors, or a combination cell line secreting two different molecules. For example, anti-angiogenic antibody-scaffold and/or PDGFR soluble antagonist cell lines were constructed using plasmids p963, p964, p974, p978, and p977, each of which encode PDGFRbeta either as a soluble receptor or as a soluble fusion protein. A PDGFR-Beta specific ELISA was developed in which capture antibody was anti-Fc and detection antibody was an anti-PDGFR Beta antibody (FIG. 10), showing that transient transfection of NTC-200 cells produces immunogenic material corresponding to the predicted structure of p963 PDGFR-IgG1 Fc, and p964 PDGFR-IgG4 Fc.

Example 11

PDGFR-Fc Producing Cell Lines

Using an approach similar to that for generating VEGF antagonist producing cell lines mentioned in the previous Examples, PDGFR antagonist producing cell lines were also generated. As shown in Table 8, clonal selection of p963 resulted in clone 963G2 with a production rate of 7.7 pcd. Further manipulation of the 963G2 by iterative transfection may be used to increase production rate of p963 protein.

TABLE 8

PDGFR-IgG1 Fc producing cell lines

| Cell Line | PDGFR-IgG1 Fc PCD |
|---|---|
| 963G2 | 7.73 |
| 96364 | 3.54 |
| 963E7 | 1.62 |

Example 12

Figure 12:
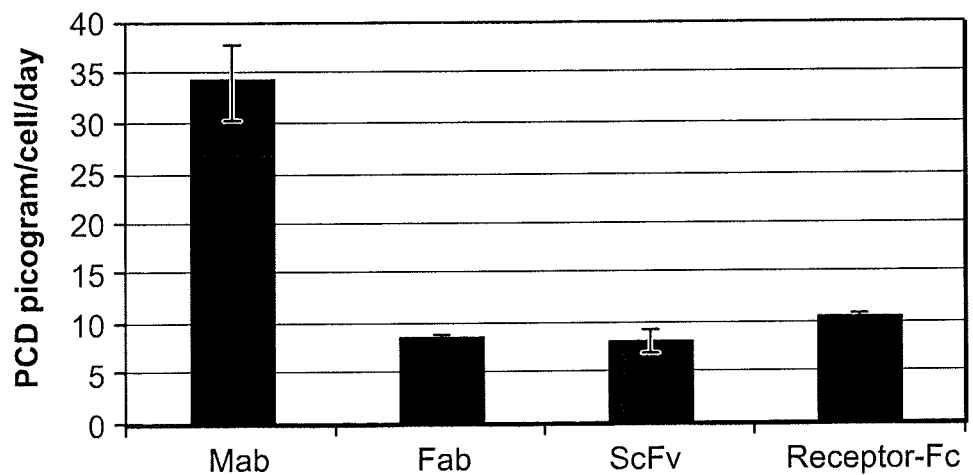
FIG. 12 shows representative cell lines secreting anti-angiogenic molecules, including monoclonal antibody, Fab fragment, Single chain antibody, and receptor Fc.
Figure 13:
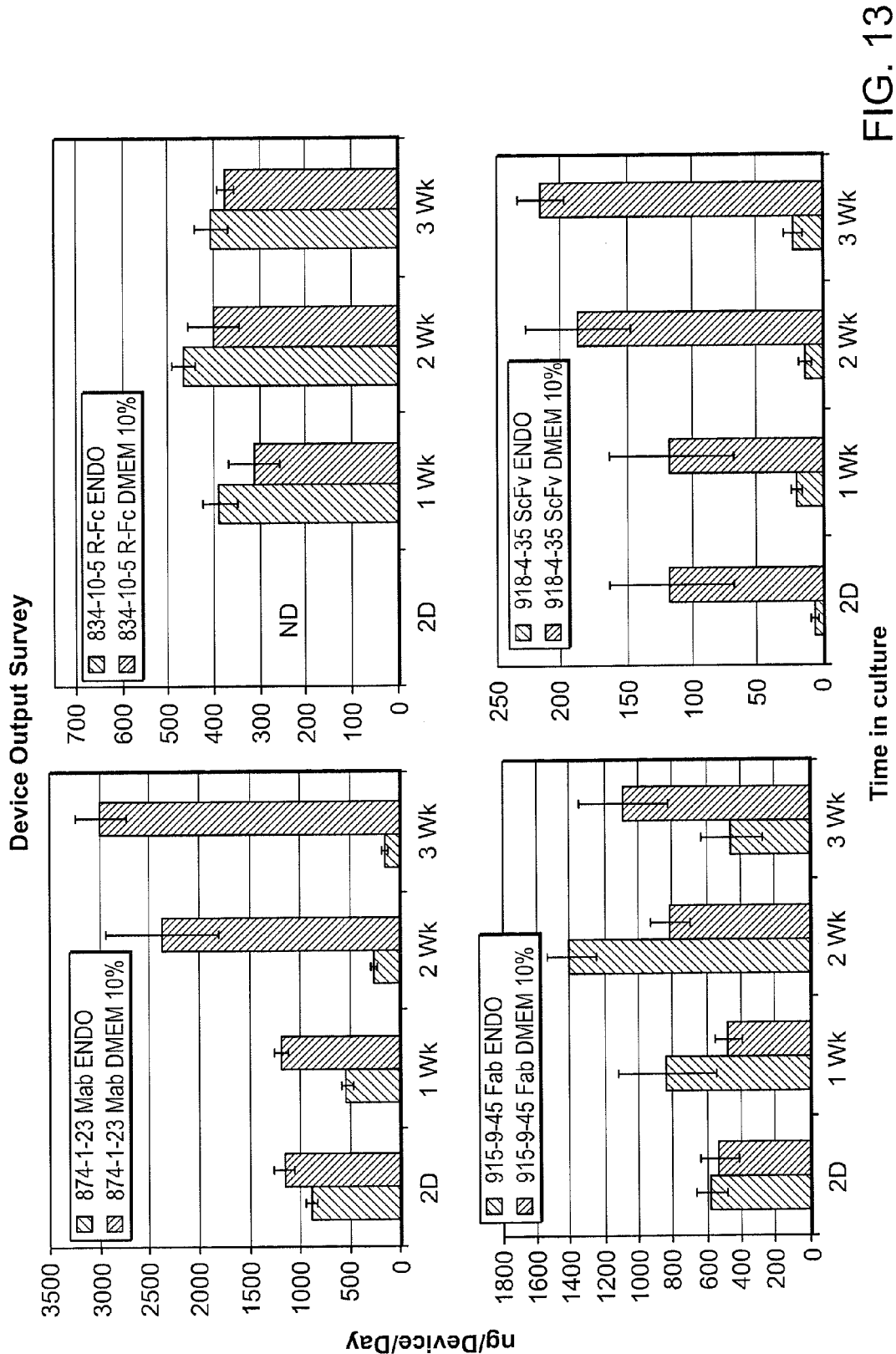
FIG. 13 shows device protein output of representative Mab, ScFv, Fab, and receptor Fc cell lines in vitro ECT format.

Other Anti-angiogenic Antibody Scaffolds in ECT, and Media Influence on Device Output In addition to 834-10-5 VEGFR-Fc antagonist, other cell lines were derived from single transfection and clonal selection. As shown in one instance in FIG. 12, cell lines representing monoclonal antibody (Mab-p874), Fab fragment (Fab-p915), Single Chain Fv (ScFv-p918) and VEGFR-Fc (Receptor-Fc-p834) were generated that produced between 8 pcd to 35 pcd (Mab). When placed into ECT device format, a wide range of recombinant protein output was observed, which was dependent on cell line used. It was also further noted that media played a large role in protein secretion, based on DMEM 10% FBS media and Endothelial serum free media (Endo-Gibco) tested.

As seen in 834-10-5 receptor Fc devices and 913-9-45 Fab devices, little difference in device output was measured based on culture with either endo or DMEM 10% FBS. However, 918-4-35 ScFv and 874-1-23 Mab devices were highly sensitive to culture in Endo, and yielded the highest output when cultured in DMEM 10% FBS, up to 3 ug/day/device for Mab.

These results suggest that preconditioning of device with appropriate media may be necessary to optimize the cells prior to implantation into the host, thereby allowing for maximal production rate and survivability.

For example, 874-1-23 devices were conditioned in DMEM 10% FBS for 4 week prior to implantation into rabbit eyes. Rabbits were enucleated one month after implantation and vitreous levels of 874 Mab proteins were assessed by VEGF-Fc ELISA and also by Fc-ELISA. As seen in Table 9, between 400 ng/ml and up to 1.7 µg/ml of 874 Mab protein was detected in rabbit vitreous implanted with ECT device.

TABLE 9

874 Anti-VEGF Mab ECT production in Rabbit vitreous and explants

| Eye # | Vitreous ng/ml vit | Explant ng/dev/day |
|---|---|---|
| 19 | 1710 | 950 |
| 20 | 663 | 526 |
| 21 | 412 | 670 |
| 22 | 615 | 728 |

In addition, 874-1-23 ECT devices were assessed for Mab output in systemic settings with SCID mice. Although 874 is an anti-VEGF antibody, its specificity has been reported against human VEGF, and not rodent VEGF. Hence, the anti-human-angiogenic function of this molecule was inferred to not have adverse physiological effects in a SCID mouse model. For each mouse, four 874-1-23 ECT devices were cultured in DMEM 10% FBS prior to implanting subcutaneously in the backs of SCID mice, with a total of 6 mice tested. After one month, mouse serum was extracted by cardiac puncture, and serum concentration of 874 protein was assessed by VEGF-Fc ELISA.

TABLE 10

Accumulation of 874 Mab protein in SCID mouse serum

| Mouse | 874 Mab Serum Levels ng/ml |
|---|---|
| #1 | 4182 |
| #2 | 18770 |
| #3 | 19172 |
| #4 | 15182 |
| #5 | 2995 |
| #6 | 839 |
| #7 control | 0 |

Therefore, as seen in Table 10, 874-1-23 ECT implants were able to produce up to 19 µg/ml steady state, of 874 Mab as measured by direct binding VEGF-Fc ELISAs. Histological examination of these ECT device sections along with adherent tissues showed numerous newly developed vascularizations in close proximity to the implant. Vascularization of the ECT device surface was achieved and allowed for diffusional recombinant protein uptake and transport into the circulatory system of the animal.

Equivalents

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

We claim:

1. A cell line comprising an ARPE-19 cell genetically engineered to produce a therapeutically effective amount of one or more anti-angiogenic polypeptides or anti-angiogenic molecules, wherein an iterative transfection process is used to genetically engineer the ARPE-19 cell, wherein the iterative transfection comprises one transfection, two sequential transfections, or three sequential transfections and wherein the one or more anti-angiogenic polypeptides or anti-angiogenic molecules is encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO: 13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31 or has an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO: 14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, and SEQ ID NO:32.

2. The cell line of claim 1, wherein the cell line produces between 10,000 and 30,000 ng/day/$10^6$ cells of the one or more anti-angiogenic polypeptides or anti-angiogenic molecules when the iterative transfection is one transfection.

3. The cell line of claim 2, wherein the cell line produces about 15,000 ng/day/$10^6$ cells of the one or more anti-angiogenic polypeptides or anti-angiogenic molecules.

4. The cell line of claim 1, wherein the cell line produces between 30,000 and 50,000 ng/day/$10^6$ cells of the one or more anti-angiogenic polypeptides or anti-angiogenic molecules when the iterative transfection is two transfections.

5. The cell line of claim 4, wherein the cell line produces about 35,000 ng/day/$10^6$ cells of the one or more anti-angiogenic polypeptides or anti-angiogenic molecules.

6. The cell line of claim 1, wherein the cell line produces between 50,000 and 75,000 ng/day/$10^6$ cells of the one or more anti-angiogenic polypeptides or anti-angiogenic molecules when the iterative transfection is three transfections.

7. The cell line of claim 6, wherein the cell line produces about 70,000 ng/day/$10^6$ cells of the one or more anti-angiogenic polypeptides or anti-angiogenic molecules.

8. The cell line of claim 1, wherein the ARPE-19 cell line is genetically engineered using a vector comprising a nucleic acid sequence encoding a soluble VEGF receptor as set forth in SEQ ID NO: 1.

9. The cell line of claim 1, wherein the ARPE-19 cell line is genetically engineered using a vector comprising a nucleic acid sequence encoding a soluble VEGF receptor as set forth in SEQ ID NO: 2.

10. A cell line comprising an ARPE-19 cell genetically engineered to produce a therapeutically effective amount of one or more anti-angiogenic polypeptides or anti-angiogenic molecules, wherein the therapeutically effective amount is at least 10,000 ng/day/$10^6$ cells.

11. An implantable cell culture device, the device comprising:
   a. the cell line of claim 1 or the cell line of claim 10 contained within a core; and
   b. a semi-permeable membrane surrounding the core, wherein the membrane permits the diffusion of the one or more anti-angiogenic polypeptides or anti-angiogenic molecules there through.

12. The device of claim 11, wherein the core contains between 0.5-1.0×$10^6$ ARPE-19 cells.

13. The device of claim 11 wherein the core further comprises a matrix disposed within the semi-permeable membrane.

14. The device of claim 13, wherein the matrix comprises a plurality of monofilaments, wherein said monofilaments are
   a. twisted into a yarn or woven into a mesh or b. twisted into a yarn that is in non-woven stands, and wherein the cells are distributed thereon.

15. The device of claim 14, wherein the monofilaments comprise a biocompatible material selected from the group consisting of acrylic, polyester, polyethylene, polypropylene polyacetonitrile, polyethylene terephthalate, nylon, polyamides, polyurethanes, polybutester, silk, cotton, chitin, carbon, and biocompatible metals.

16. The device of claim 15, wherein the monofilaments comprise polyethylene terephthalate (PET) fibers that comprises between 40-85% of internal volume of the device.

17. The device of claim 11, wherein the device further comprises a tether anchor.

18. The device of claim 17, wherein the tether anchor comprises an anchor loop.

19. The device of claim 18, wherein the anchor loop is adapted for anchoring the device to an ocular structure.

20. The device of claim 11, wherein the device is implanted into the eye or another target region selected from the group consisting of spleen, ear, heart, colon, liver, kidney, breast, joint, bone marrow, subcutaneous, and peritoneal spaces.

21. The device of claim 20, wherein the device is implanted in the vitreous, the aqueous humor, the Subtenon's space, the periocular space, the posterior chamber, or the anterior chamber of the eye.

22. The device of claim 11, wherein the semi-permeable membrane comprises a permselective, immunoprotective membrane.

23. The device of claim 11, wherein the semi-permeable membrane comprises an ultrafiltration membrane or a microfiltration membrane.

24. The device of claim 22 or 23, wherein the semi-permeable membrane has a median pore size of 100 nm.

25. The device of claim 11, wherein the semi-permeable membrane comprises a non-porous membrane material.

26. The device of claim 25, wherein the non-porous membrane material is a hydrogel or a polyurethane.

27. The device of claim 11, wherein the nominal molecular weight cut off (MWCO) of the semi-permeable membrane is 500 kD.

28. The device of claim 11, wherein the semi-permeable membrane is between 90-120 µm thick.

29. The device of claim 11, wherein the length of the device is between 4 mm-11 mm.

30. The device of claim 11, wherein the device has an internal diameter of between 0.9 mm-1.2 mm.

31. The device of claim 11, wherein the ends of the device are sealed using methyl methacrylate.

32. The device of claim 11, wherein at least one additional biologically active molecule is co-delivered from the device.

33. The device of claim 32, wherein the at least one additional biologically active molecule is from a non-cellular source.

34. The device of claim 32, wherein the at least one additional biologically active molecule is from a cellular source.

35. The device of claim 34, wherein the at least one additional biologically active molecule is produced by one or more genetically engineered ARPE-19 cells in the core.

36. The device of claim 11, further comprising one or more additional characteristics selected from the group consisting of:
   a. the core comprises between $0.5-1.0 \times 10^6$ ARPE-19 cells;
   b. length of the device is between 4 mm-11 mm;
   c. the internal diameter of the device is between 0.9 mm-1.2 mm;
   d. the ends of the device are sealed using methyl methacrylate;
   e. the semi-permeable membrane has a median pore size of about 100 nm;
   f. the nominal molecular weight cut off (MWCO) of the semi-permeable membrane is 500 KD;
   g. the semi-permeable membrane is between 90-120 µm thick;
   h. core comprises an internal scaffold, wherein the scaffold comprises polyethylene terephthalate (PET) fibers that comprises between 40-85% of internal volume of the device; and
   i. combinations thereof.

37. The device of claim 36, wherein the one or more additional characteristics comprises 2, 3, 4, 5, 6, 7, or all of additional characteristics a-i.

38. A method for making the implantable cell culture device of claim 11, comprising
   a. genetically engineering at least one ARPE-19 cell to secrete one or more anti-angiogenic polypeptides or anti-angiogenic molecules, and
   b. encapsulating said genetically modified ARPE-19 cells within a semi-permeable membrane, wherein said membrane allows the diffusion of the one or more anti-angiogenic polypeptides or anti-angiogenic molecules there through.

39. The method of claim 38, wherein the one or more anti-angiogenic polypeptides or anti-angiogenic molecules is encoded by a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO: 13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, and SEQ ID NO:31.

* * * * *

UNITED STATES PATENT AND TRADEMARK OFFICE
CERTIFICATE OF CORRECTION

| | |
|---|---|
| PATENT NO. | : 9,149,427 B2 |
| APPLICATION NO. | : 13/308264 |
| DATED | : October 6, 2015 |
| INVENTOR(S) | : Ling et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 16 days.

Signed and Sealed this
Twelfth Day of April, 2016

Michelle K. Lee
*Director of the United States Patent and Trademark Office*

SEQUENCE LISTING

<160> NUMBER OF SEQ ID NOS: 32

<210> SEQ ID NO 1
<211> LENGTH: 1401
<212> TYPE: DNA
<213> ORGANISM: Artificial Sequence
<220> FEATURE:
<223> OTHER INFORMATION: 834 molecule nucleic acid sequence

<400> SEQUENCE: 1

```
atggtcagct actgggacac cggggtcctg ctgtgcgcgc tgctcagctg tctgcttctc      60
acaggatcta gttcaggttc gcgaagtgat acaggtagac ctttcgtaga gatgtacagt     120
gaaatccccg aaattataca catgactgaa ggaagggagc tcgtcattcc ctgccgggtt     180
acgtcaccta acatcactgt tactttaaaa aagtttccac ttgacacttt gatccctgat     240
ggaaaacgca taatctggga cagtagaaag ggcttcatca tatcaaatgc aacgtacaaa     300
gaaatagggc ttctgacctg tgaagcaaca gtcaatgggc atttgtataa gacaaactat     360
ctcacacatc gacaaaccaa tacaatcatc gatgtggttc tgagtccgtc tcatggaatt     420
gaactatctg ttggagaaaa gcttgtctta aattgtacag caagaactga actaaatgtg     480
gggattgact tcaactggga ataccttcct tcgaagcatc agcataagaa acttgtaaac     540
cgagacctaa aaacccagtc tgggagtgag atgaagaaat ttttgagcac cttaactata     600
gatggtgtaa cccggagtga ccaaggattg tacacctgtg cagcatccag tgggctgatg     660
accaagaaga acagcacatt tgtcagggtc catgaaaaag aattcgagcc caaatcttgt     720
gacaaaactc acacatgccc accgtgccca gcacctgaac tcctgggggg accgtcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa a                                              1401
```

<210> SEQ ID NO 2
<211> LENGTH: 467

<212> TYPE: PRT
<213> ORGANISM: Artificial Sequence
<220> FEATURE:
<223> OTHER INFORMATION: 834 molecule amino acid sequence

<400> SEQUENCE: 2

Met Val Ser Tyr Trp Asp Thr Gly Val Leu Leu Cys Ala Leu Leu Ser
1               5                   10                  15

Cys Leu Leu Thr Gly Ser Ser Ser Gly Ser Arg Ser Asp Thr Gly
            20                  25                  30

Arg Pro Phe Val Glu Met Tyr Ser Glu Ile Pro Glu Ile Ile His Met
                35                  40                  45

Thr Glu Gly Arg Glu Leu Val Ile Pro Cys Arg Val Thr Ser Pro Asn
50                  55                  60

Ile Thr Val Thr Leu Lys Lys Phe Pro Leu Asp Thr Leu Ile Pro Asp
65                  70                  75                  80

Gly Lys Arg Ile Ile Trp Asp Ser Arg Lys Gly Phe Ile Ile Ser Asn
                85                  90                  95

Ala Thr Tyr Lys Glu Ile Gly Leu Leu Thr Cys Glu Ala Thr Val Asn
            100                 105                 110

Gly His Leu Tyr Lys Thr Asn Tyr Leu Thr His Arg Gln Thr Asn Thr
        115                 120                 125

Ile Ile Asp Val Val Leu Ser Pro Ser His Gly Ile Glu Leu Ser Val
130                 135                 140

Gly Glu Lys Leu Val Leu Asn Cys Thr Ala Arg Thr Glu Leu Asn Val
145                 150                 155                 160

Gly Ile Asp Phe Asn Trp Glu Tyr Pro Ser Ser Lys His Gln His Lys
                165                 170                 175

Lys Leu Val Asn Arg Asp Leu Lys Thr Gln Ser Gly Ser Glu Met Lys
            180                 185                 190

Lys Phe Leu Ser Thr Leu Thr Ile Asp Gly Val Thr Arg Ser Asp Gln
        195                 200                 205

Gly Leu Tyr Thr Cys Ala Ala Ser Ser Gly Leu Met Thr Lys Lys Asn
210                 215                 220

Ser Thr Phe Val Arg Val His Glu Lys Glu Phe Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 1707
<212> TYPE: DNA
<213> ORGANISM: Artificial Sequence
<220> FEATURE:
<223> OTHER INFORMATION: 838 molecule nucleic acid sequence

<400> SEQUENCE: 3
```

| | | | | | |
|---|---|---|---|---|---|
| atggagagca | aggtgctgct | ggccgtcgcc | ctgtggctct | cgtggagac | ccggccgcc | 60 |
| tctgtgggtt | tgcctagtgt | ttctcttgat | ctgcccaggc | tcagcataca | aaaagacata | 120 |
| cttacaatta | aggctaatac | aactcttcaa | attacttgca | ggggacagag | ggacttggac | 180 |
| tggctttggc | ccaataatca | gagtggcagt | gagcaaaggg | tggaggtgac | tgagtgcagc | 240 |
| gatggcctct | tctgtaagac | actcacaatt | ccaaaagtga | tcgaaatga | cactggagcc | 300 |
| tacaagtgct | tctaccggga | aactgacttg | gcctcggtca | tttatgtcta | tgttcaagat | 360 |
| tacagatctc | catttattgc | ttctgttagt | gaccaacatg | gagtcgtgta | cattactgag | 420 |
| aacaaaaaca | aaactgtggt | gattccatgt | ctcgggtcca | tttcaaatct | caacgtgtca | 480 |
| ctttgtgcaa | gatacccaga | aaagagattt | gttcctgatg | gtaacagaat | ttcctgggac | 540 |
| agcaagaagg | gctttactat | tcccagctac | atgatcagct | atgctggcat | ggtcttctgt | 600 |
| gaagcaaaaa | ttaatgatga | agttaccag | tctattatgt | acatagttgt | cgttgtaggg | 660 |
| tataggattt | atgatgtggt | tctgagtccg | tctcatggaa | ttgaactatc | tgttggagaa | 720 |
| aagcttgtct | taattgtac | agcaagaact | gaactaaatg | tggggattga | cttcaactgg | 780 |
| gaataccctt | cttcgaagca | tcagcataag | aaacttgtaa | accgagacct | aaaaacccag | 840 |
| tctgggagtg | agatgaagaa | attttttgagc | accttaacta | tagatggtgt | aacccggagt | 900 |
| gaccaaggat | tgtacacctg | tgcagcatcc | agtgggctga | tgaccaagaa | gaacagcaca | 960 |
| tttgtcaggg | tccatgaaaa | accttttgtt | gcttttggaa | gtggcgaatt | cgagcccaaa | 1020 |
| tcttgtgaca | aaactcacac | atgcccaccg | tgcccagcac | ctgaactcct | gggggaccg | 1080 |
| tcagtcttcc | tcttcccccc | aaaacccaag | gacaccctca | tgatctcccg | gacccctgag | 1140 |
| gtcacatgcg | tggtggtgga | cgtgagccac | gaagaccctg | aggtcaagtt | caactggtac | 1200 |
| gtggacggcg | tggaggtgca | taatgccaag | acaaagccgc | gggaggagca | gtacaacagc | 1260 |
| acgtaccgtg | tggtcagcgt | cctcaccgtc | ctgcaccagg | actggctgaa | tggcaaggag | 1320 |
| tacaagtgca | aggtctccaa | caaagccctc | ccagccccca | tcgagaaaac | catctccaaa | 1380 |
| gccaaagggc | agccccgaga | accacaggtg | tacaccctgc | ccccatcccg | ggatgagctg | 1440 |
| accaagaacc | aggtcagcct | gacctgcctg | gtcaaaggct | tctatcccag | cgacatcgcc | 1500 |
| gtggagtggg | agagcaatgg | gcagccggag | aacaactaca | agaccacgcc | tcccgtgctg | 1560 |

-continued

```
gactccgacg gctccttctt cctctacagc aagctcaccg tggacaagag caggtggcag    1620
caggggaacg tcttctcatg ctccgtgatg catgaggctc tgcacaacca ctacacgcag    1680
aagagcctct ccctgtctcc gggtaaa                                        1707
```

<210> SEQ ID NO 4
<211> LENGTH: 569
<212> TYPE: PRT
<213> ORGANISM: Artificial Sequence
<220> FEATURE:
<223> OTHER INFORMATION: 838 molecule amino acid sequence

<400> SEQUENCE: 4

```
Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Glu
                325                 330                 335
```

```
Phe Glu Pro Lys Ser Cys Asp Lys Thr His Thr Cys Pro Cys Pro
            340                 345                 350

Ala Pro Glu Leu Leu Gly Gly Pro Ser Val Phe Leu Phe Pro Pro Lys
            355                 360                 365

Pro Lys Asp Thr Leu Met Ile Ser Arg Thr Pro Glu Val Thr Cys Val
370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
                405                 410                 415

Gln Tyr Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
            435                 440                 445

Ala Leu Pro Ala Pro Ile Glu Lys Thr Ile Ser Lys Ala Lys Gly Gln
450                 455                 460

Pro Arg Glu Pro Gln Val Tyr Thr Leu Pro Pro Ser Arg Asp Glu Leu
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
            515                 520                 525

Tyr Ser Lys Leu Thr Val Asp Lys Ser Arg Trp Gln Gln Gly Asn Val
530                 535                 540

Phe Ser Cys Ser Val Met His Glu Ala Leu His Asn His Tyr Thr Gln
545                 550                 555                 560

Lys Ser Leu Ser Leu Ser Pro Gly Lys
                565

<210> SEQ ID NO 5
<211> LENGTH: 819
<212> TYPE: DNA
<213> ORGANISM: Artificial Sequence
<220> FEATURE:
<223> OTHER INFORMATION: 876 molecule nucleic acid sequence

<400> SEQUENCE: 5
atggacatgc gggtgccagc tcagctgctg ggactgctgc tgctgtggct gcccggcacc      60
agatgcgaca tccagctgac ccagtccccc tccagcctgt ccgcctctgt gggcgacaga     120
gtgaccatca cctgttccgc ctcccaggac atcagcaact acctgaactg gtatcagcag     180
aagcccggca aggcccccaa ggtgctgatc tacttcacca gcagcctgca ctccggcgtg     240 ccctccggt tctccggctc cggctccggc accgacttca ccctgaccat ctccagcctg     300
cagcccgagg acttcgccac ctactactgc cagcagtaca gcaccgtgcc ctggaccttc     360
ggccagggca ccaaggtgga aatcaaggga ggtggaggaa gcggtggagg aggtagcgga     420
ggcggcggca gcgaggtgca gctggtggaa tccggcggag actggtgca gcctggcggc     480 tccctgagac tgtcttgcgc cgcctccggc tacgacttca cccactacgg catgaactgg     540
gtccgacagg cccctggcaa gggactggaa tgggtgggct ggatcaacac ctacaccggc     600
gagcccacct acgccgccga cttcaagcgg cggttcacct tcagcctgga caccagcaag     660
agcaccgcct acctgcagat gaactccctg cgggccgagg acaccgccgt gtactactgc     720
```

```
gccaagtacc cctactacta cggcaccagc cactggtact tcgacgtgtg gggccagggc    780
accctggtca ccgtctcctc acaccatcac caccaccac                           819
```

<210> SEQ ID NO 6
<211> LENGTH: 273
<212> TYPE: PRT
<213> ORGANISM: Artificial Sequence
<220> FEATURE:
<223> OTHER INFORMATION: 876 molecule amino acid sequence

<400> SEQUENCE: 6

```
Met Asp Met Arg Val Pro Ala Gln Leu Leu Gly Leu Leu Leu Leu Trp
1               5                   10                  15

Leu Pro Gly Thr Arg Cys Asp Ile Gln Leu Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Tyr Asp Phe Thr His Tyr
                165                 170                 175

Gly Met Asn Trp Val Arg Gln Ala Pro Gly Lys Gly Leu Glu Trp Val
            180                 185                 190

Gly Trp Ile Asn Thr Tyr Thr Gly Glu Pro Thr Tyr Ala Ala Asp Phe
        195                 200                 205

Lys Arg Arg Phe Thr Phe Ser Leu Asp Thr Ser Lys Ser Thr Ala Tyr
    210                 215                 220

Leu Gln Met Asn Ser Leu Arg Ala Glu Asp Thr Ala Val Tyr Tyr Cys
225                 230                 235                 240

Ala Lys Tyr Pro Tyr Tyr Tyr Gly Thr Ser His Trp Tyr Phe Asp Val
                245                 250                 255

Trp Gly Gln Gly Thr Leu Val Thr Val Ser Ser His His His His
            260                 265                 270

His
```

<210> SEQ ID NO 7
<211> LENGTH: 1371
<212> TYPE: DNA
<213> ORGANISM: Artificial Sequence
<220> FEATURE:
<223> OTHER INFORMATION: 873 molecule nucleic acid sequence

<400> SEQUENCE: 7

```
atggtcagct actgggacac cggggtcctg ctgtgcgcgc tgctcagctg tctgcttctc    60
```

```
acaggatcta gttcaggtag tgatacaggt agacctttcg tagagatgta cagtgaaatc    120
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaagggcttc atcatatcaa atgcaacgta caagaaaata    300
gggcttctga cctgtgaagc aacagtcaat gggcatttgt ataagacaaa ctatctcaca    360
catcgacaaa ccaatacaat catcgatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata agaaacttgt aaaccgagac    540 ctaaaaccc agtctgggag tgagatgaag aaatttttga gcaccttaac tatagatggt    600
gtaacccgga gtgaccaagg attgtacacc tgtgcagcat ccagtgggct gatgaccaag    660
aagaacagca catttgtcag ggtccatgaa aaagacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta acagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc ccgagaacc acaggtgtac   1080 accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg t           1371
```

<210> SEQ ID NO 8
<211> LENGTH: 457
<212> TYPE: PRT
<213> ORGANISM: Artificial Sequence
<220> FEATURE:
<223> OTHER INFORMATION: 873 molecule amino acid sequence

<400> SEQUENCE: 8

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125
```

```
Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
450                 455
```

<210> SEQ ID NO 9
<211> LENGTH: 1416
<212> TYPE: DNA
<213> ORGANISM: Artificial Sequence
<220> FEATURE:
<223> OTHER INFORMATION: 874 molecule nucleic acid sequence

<400> SEQUENCE: 9

```
atggactgga cctggtctat cctgttcctg gtggccgctg caaccggcac ctactccgag      60
gtgcagctgg tggaatccgg cggaggactg gtgcagcctg gcggctccct gagactgtct     120
tgcgccgcct ccggctacac cttcaccaac tacggcatga actgggtccg acaggcccct     180
```

```
ggcaagggac tggaatgggt gggctggatc aacacctaca ccggcgagcc cacctacgcc      240
gccgacttca agcggcggtt caccttcagc ctggacacca gcaagagcac cgcctacctg      300
cagatgaact ccctgcgggc cgaggacacc gccgtgtact actgcgccaa gtaccccac       360
tactacggca gcagccactg gtacttcgac gtgtggggcc agggcaccct ggtcaccgtc      420
tcctcagcct ccaccaaggg cccatcggtc ttccccctgg cacctcctc caagagcacc       480
tctgggggca cagcggccct gggctgcctg gtcaaggact acttccccga accggtgacg      540
gtgtcgtgga actcaggcgc cctgaccagc ggcgtgcaca ccttcccggc tgtcctacag      600
tcctcaggac tctactccct cagcagcgtg gtgaccgtgc cctccagcag cttgggcacc      660
cagacctaca tctgcaacgt gaatcacaag cccagcaaca ccaaggtgga caagaaagtt      720
gagcccaaat cttgtgacaa aactcacaca tgcccaccgt gcccagcacc tgaactcctg      780
gggggaccgt cagtcttcct cttccccca aaacccaagg acaccctcat gatctcccgg       840
accccctgagg tcacatgcgt ggtggtggac gtgagccacg aagaccctga ggtcaagttc      900
aactggtacg tggacggcgt ggaggtgcat aatgccaaga caaagccgcg ggaggagcag      960
tacaacagca cgtaccgtgt ggtcagcgtc ctcaccgtcc tgcaccagga ctggctgaat     1020
ggcaaggagt acaagtgcaa ggtctccaac aaagccctcc cagcccccat cgagaaaacc     1080
atctccaaag ccaaagggca gccccgagaa ccacaggtgt acaccctgcc cccatcccgg     1140
gatgagctga ccaagaacca ggtcagcctg acctgcctgg tcaaaggctt ctatcccagc     1200
gacatcgccg tggagtggga gagcaatggg cagccggaga caactacaa gaccacgcct      1260
cccgtgctgg actccgacgg ctccttcttc ctctacagca agctcaccgt ggacaagagc     1320
aggtggcagc aggggaacgt cttctcatgc tccgtgatgc atgaggctct gcacaaccac     1380
tacacgcaga agagcctctc cctgtctccg ggtaaa                              1416

<210> SEQ ID NO 10
<211> LENGTH: 472
<212> TYPE: PRT
<213> ORGANISM: Artificial Sequence
<220> FEATURE:
<223> OTHER INFORMATION: 874 molecule amino acid sequence

<400> SEQUENCE: 10

Met Asp Trp Thr Trp Ser Ile Leu Phe Leu Val Ala Ala Ala Thr Gly
1               5                   10                  15

Thr Tyr Ser Glu Val Gln Leu Val Glu Ser Gly Gly Gly Leu Val Gln
                20                  25                  30

Pro Gly Gly Ser Leu Arg Leu Ser Cys Ala Ala Ser Gly Tyr Thr Phe
            35                  40                  45

Thr Asn Tyr Gly Met Asn Trp Val Arg Gln Ala Pro Gly Lys Gly Leu
        50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro His Tyr Tyr Gly Ser Ser His Trp Tyr
        115                 120                 125

Phe Asp Val Trp Gly Gln Gly Thr Leu Val Thr Val Ser Ser Ala Ser
    130                 135                 140
```

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 11
<211> LENGTH: 708
<212> TYPE: DNA
<213> ORGANISM: Artificial Sequence
<220> FEATURE:
<223> OTHER INFORMATION: 875 molecule nucleic acid sequence

<400> SEQUENCE: 11
atggacatgc gggtgccagc tcagctgctg ggactgctgc tgctgtggct gcccggcacc      60
agatgcgaca tccagatgac ccagtccccc tccagcctgt ccgcctctgt gggcgacaga     120
gtgaccatca cctgttccgc ctcccaggac atcagcaact acctgaactg gtatcagcag     180

```
aagcccggca aggcccccaa ggtgctgatc tacttcacca gcagcctgca ctccggcgtg      240
ccctcccggt tctccggctc cggctccggc accgacttca ccctgaccat ctccagcctg      300
cagcccgagg acttcgccac ctactactgc agcagtaca gcaccgtgcc ctggaccttc       360
ggccagggca ccaaggtgga aatcaagcgg accgtggccg ctcccctccgt gttcatcttc     420 ccacccctccg acgagcagct gaagtccggc accgcctccg tcgtctgcct gctgaacaac    480
ttctaccccc gcgaggccaa ggtgcagtgg aaggtggaca acgccctgca gtccggcaac     540
tcccaggaat ccgtcaccga gcaggactcc aaggacagca cctactccct gtcctccacc     600
ctgaccctgt ccaaggccga ctacgagaag cacaaggtgt acgcctgcga agtgacccac    660
cagggcctgt ccagccccgt gaccaagtcc ttcaaccggg gcgagtgc                  708
```

<210> SEQ ID NO 12
<211> LENGTH: 236
<212> TYPE: PRT
<213> ORGANISM: Artificial Sequence
<220> FEATURE:
<223> OTHER INFORMATION: 875 molecule amino acid sequence

<400> SEQUENCE: 12

```
Met Asp Met Arg Val Pro Ala Gln Leu Leu Gly Leu Leu Leu Leu Trp
1               5                   10                  15

Leu Pro Gly Thr Arg Cys Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 13
<211> LENGTH: 750
<212> TYPE: DNA
<213> ORGANISM: Artificial Sequence
<220> FEATURE:

<223> OTHER INFORMATION: 915 molecule nucleic acid sequence

<400> SEQUENCE: 13

```
atggactgga cctggtctat cctgttcctg gtggccgctg caaccggcac ctactccgag      60
gtgcagctgg tggaatccgg cggaggactg gtgcagcctg gcggctccct gagactgtct     120
tgcgccgcct ccggctacga cttcacccac tacggcatga actgggtccg acaggcccct     180
ggcaagggac tggaatgggt gggctggatc aacacctaca ccggcgagcc cacctacgcc     240
gccgacttca gcggcggtt caccttcagc ctggacacca gcaagagcac cgcctacctg     300
cagatgaact ccctgcgggc cgaggacacc gccgtgtact actgcgccaa gtaccccctac    360
tactacggca ccagccactg gtacttcgac gtgtggggcc agggcaccct ggtcaccgtc     420
tcctcagcct ccaccaaggg cccatcggtc ttccccctgg cccctcctc caagagcacc      480
tctggggca gcggccct gggctgcctg gtcaaggact acttccccga accggtgacg         540
gtgtcgtgga actcaggcgc cctgaccagc ggcgtgcaca ccttcccggc tgtcctacag      600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacctg                                     750
```

<210> SEQ ID NO 14
<211> LENGTH: 250
<212> TYPE: PRT
<213> ORGANISM: Artificial Sequence
<220> FEATURE:
<223> OTHER INFORMATION: 915 molecule amino acid sequence

<400> SEQUENCE: 14

```
Met Asp Trp Thr Trp Ser Ile Leu Phe Leu Val Ala Ala Thr Gly
1               5                  10                  15

Thr Tyr Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Asp Phe
        35                  40                  45

Thr His Tyr Gly Met Asn Trp Val Arg Gln Ala Pro Gly Lys Gly Leu
    50                  55                  60

Glu Trp Val Gly Trp Ile Asn Thr Tyr Thr Gly Glu Pro Thr Tyr Ala
65                  70                  75                  80

Ala Asp Phe Lys Arg Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Tyr Pro Tyr Tyr Tyr Gly Thr Ser His Trp Tyr
        115                 120                 125

Phe Asp Val Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205
```

Ser Val Val Thr Val Pro Ser Ser Leu Gly Thr Gln Thr Tyr Ile
            210                 215                 220

Cys Asn Val Asn His Lys Pro Ser Asn Thr Lys Val Asp Lys Lys Val
225                 230                 235                 240

Glu Pro Lys Ser Cys Asp Lys Thr His Leu
            245                 250

<210> SEQ ID NO 15
<211> LENGTH: 708
<212> TYPE: DNA
<213> ORGANISM: Artificial Sequence
<220> FEATURE:
<223> OTHER INFORMATION: 914 molecule nucleic acid sequence

<400> SEQUENCE: 15

```
atggacatgc gggtgccagc tcagctgctg ggactgctgc tgctgtggct gcccggcacc    60
agatgcgaca tccagctgac ccagtccccc tccagcctgt ccgcctctgt gggcgacaga   120
gtgaccatca cctgttccgc ctcccaggac atcagcaact acctgaactg gtatcagcag   180
aagcccggca aggcccccaa ggtgctgatc tacttcacca gcagcctgca ctccggcgtg   240
ccctcccggt tctccggctc cggctccggc accgacttca ccctgaccat ctccagcctg   300
cagcccgagg acttcgccac ctactactgc cagcagtaca gcaccgtgcc ctggaccttc   360
ggccagggca ccaaggtgga aatcaagcgg accgtggccg ctcccctccgt gttcatcttc   420
ccaccctccg acgagcagct gaagtccggc accgcctccg tcgtctgcct gctgaacaac   480
ttctacccc gcgaggccaa ggtgcagtgg aaggtggaca cgccctgca gtccggcaac   540
tcccaggaat ccgtcaccga gcaggactcc aaggacagca cctactccct gtcctccacc   600
ctgaccctgt ccaaggccga ctacgagaag cacaaggtgt acgcctgcga agtgacccac   660
cagggcctgt ccagccccgt gaccaagtcc ttcaaccggg gcgagtgc              708
```

<210> SEQ ID NO 16
<211> LENGTH: 236
<212> TYPE: PRT
<213> ORGANISM: Artificial Sequence
<220> FEATURE:
<223> OTHER INFORMATION: 914 molecule amino acid sequence

<400> SEQUENCE: 16

Met Asp Met Arg Val Pro Ala Gln Leu Leu Gly Leu Leu Leu Leu Trp
1               5                   10                  15

Leu Pro Gly Thr Arg Cys Asp Ile Gln Leu Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 17
<211> LENGTH: 1416
<212> TYPE: DNA
<213> ORGANISM: Artificial Sequence
<220> FEATURE:
<223> OTHER INFORMATION: 916 molecule nucleic acid sequence

<400> SEQUENCE: 17
atggactgga cctggtctat cctgttcctg gtggccgctg caaccggcac ctactccgag     60
gtgcagctgg tggaatccgg cggaggactg gtgcagcctg gcggctccct gagactgtct    120
tgcgccgcct ccggctacga cttcacccac tacggcatga ctgggtccg acaggcccct    180 ggcaagggac tggaatgggt gggctggatc aacacctaca ccggcgagcc cacctacgcc    240
gccgacttca gcggcggttt caccttcagc ctggacacca gcaagagcac cgcctacctg    300
cagatgaact ccctgcgggc cgaggacacc gccgtgtact actgcgccaa gtacccctac    360
tactacggca ccagccactg gtacttcgac gtgtggggcc agggcaccct ggtcaccgtc    420
tcctcagcct ccaccaaggg cccatcggtc ttccccctgg cacccctcc caagagcacc    480 tctgggggca gcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagccccat cgagaaaacc   1080 atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416

<210> SEQ ID NO 18

```
<211> LENGTH: 472
<212> TYPE: PRT
<213> ORGANISM: Artificial Sequence
<220> FEATURE:
<223> OTHER INFORMATION: 916 molecule amino acid sequence

<400> SEQUENCE: 18
```

| | | | | | | | | | | | | | | | |
|---|---|---|---|---|---|---|---|---|---|---|---|---|---|---|---|
| Met | Asp | Trp | Thr | Trp | Ser | Ile | Leu | Phe | Leu | Val | Ala | Ala | Ala | Thr | Gly |
| 1 | | | | 5 | | | | | 10 | | | | | 15 | |
| Thr | Tyr | Ser | Glu | Val | Gln | Leu | Val | Glu | Ser | Gly | Gly | Gly | Leu | Val | Gln |
| | | | 20 | | | | | 25 | | | | | 30 | | |
| Pro | Gly | Gly | Ser | Leu | Arg | Leu | Ser | Cys | Ala | Ala | Ser | Gly | Tyr | Asp | Phe |
| | | | | 35 | | | | | 40 | | | | | 45 | |
| Thr | His | Tyr | Gly | Met | Asn | Trp | Val | Arg | Gln | Ala | Pro | Gly | Lys | Gly | Leu |
| | 50 | | | | | 55 | | | | | 60 | | | | |
| Glu | Trp | Val | Gly | Trp | Ile | Asn | Thr | Tyr | Thr | Gly | Glu | Pro | Thr | Tyr | Ala |
| 65 | | | | | 70 | | | | | 75 | | | | | 80 |
| Ala | Asp | Phe | Lys | Arg | Arg | Phe | Thr | Phe | Ser | Leu | Asp | Thr | Ser | Lys | Ser |
| | | | | 85 | | | | | 90 | | | | | 95 | |
| Thr | Ala | Tyr | Leu | Gln | Met | Asn | Ser | Leu | Arg | Ala | Glu | Asp | Thr | Ala | Val |
| | | | 100 | | | | | 105 | | | | | 110 | | |
| Tyr | Tyr | Cys | Ala | Lys | Tyr | Pro | Tyr | Tyr | Tyr | Gly | Thr | Ser | His | Trp | Tyr |
| | | | | 115 | | | | | 120 | | | | | 125 | |
| Phe | Asp | Val | Trp | Gly | Gln | Gly | Thr | Leu | Val | Thr | Val | Ser | Ser | Ala | Ser |
| | | 130 | | | | | 135 | | | | | 140 | | | |
| Thr | Lys | Gly | Pro | Ser | Val | Phe | Pro | Leu | Ala | Pro | Ser | Ser | Lys | Ser | Thr |
| 145 | | | | | 150 | | | | | 155 | | | | | 160 |
| Ser | Gly | Gly | Thr | Ala | Ala | Leu | Gly | Cys | Leu | Val | Lys | Asp | Tyr | Phe | Pro |
| | | | | 165 | | | | | 170 | | | | | 175 | |
| Glu | Pro | Val | Thr | Val | Ser | Trp | Asn | Ser | Gly | Ala | Leu | Thr | Ser | Gly | Val |
| | | | 180 | | | | | 185 | | | | | 190 | | |
| His | Thr | Phe | Pro | Ala | Val | Leu | Gln | Ser | Ser | Gly | Leu | Tyr | Ser | Leu | Ser |
| | | | | 195 | | | | | 200 | | | | | 205 | |
| Ser | Val | Val | Thr | Val | Pro | Ser | Ser | Ser | Leu | Gly | Thr | Gln | Thr | Tyr | Ile |
| | | 210 | | | | | 215 | | | | | 220 | | | |
| Cys | Asn | Val | Asn | His | Lys | Pro | Ser | Asn | Thr | Lys | Val | Asp | Lys | Lys | Val |
| 225 | | | | | 230 | | | | | 235 | | | | | 240 |
| Glu | Pro | Lys | Ser | Cys | Asp | Lys | Thr | His | Thr | Cys | Pro | Pro | Cys | Pro | Ala |
| | | | | 245 | | | | | 250 | | | | | 255 | |
| Pro | Glu | Leu | Leu | Gly | Gly | Pro | Ser | Val | Phe | Leu | Phe | Pro | Pro | Lys | Pro |
| | | | 260 | | | | | 265 | | | | | 270 | | |
| Lys | Asp | Thr | Leu | Met | Ile | Ser | Arg | Thr | Pro | Glu | Val | Thr | Cys | Val | Val |
| | | 275 | | | | | 280 | | | | | 285 | | | |
| Val | Asp | Val | Ser | His | Glu | Asp | Pro | Glu | Val | Lys | Phe | Asn | Trp | Tyr | Val |
| | 290 | | | | | 295 | | | | | 300 | | | | |
| Asp | Gly | Val | Glu | Val | His | Asn | Ala | Lys | Thr | Lys | Pro | Arg | Glu | Glu | Gln |
| 305 | | | | | 310 | | | | | 315 | | | | | 320 |
| Tyr | Asn | Ser | Thr | Tyr | Arg | Val | Val | Ser | Val | Leu | Thr | Val | Leu | His | Gln |
| | | | | 325 | | | | | 330 | | | | | 335 | |
| Asp | Trp | Leu | Asn | Gly | Lys | Glu | Tyr | Lys | Cys | Lys | Val | Ser | Asn | Lys | Ala |
| | | | 340 | | | | | 345 | | | | | 350 | | |
| Leu | Pro | Ala | Pro | Ile | Glu | Lys | Thr | Ile | Ser | Lys | Ala | Lys | Gly | Gln | Pro |
| | | | 355 | | | | | 360 | | | | | 365 | | |
| Arg | Glu | Pro | Gln | Val | Tyr | Thr | Leu | Pro | Pro | Ser | Arg | Asp | Glu | Leu | Thr |
| | | | 370 | | | | | 375 | | | | | 380 | | |

-continued

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 19
<211> LENGTH: 801
<212> TYPE: DNA
<213> ORGANISM: Artificial Sequence
<220> FEATURE:
<223> OTHER INFORMATION: 913 molecule nucleic acid sequence

<400> SEQUENCE: 19

```
atggacatgc gggtgccagc tcagctgctg ggactgctgc tgctgtggct gcccggcacc     60
agatgcgaca tccagctgac ccagtccccc tccagcctgt ccgcctctgt gggcgacaga    120
gtgaccatca cctgttccgc ctcccaggac atcagcaact acctgaactg gtatcagcag    180
aagcccggca aggccccccaa ggtgctgatc tacttcacca gcagcctgca ctccggcgtg    240
ccctcccggt tctccggctc cggctccggc accgacttca ccctgaccat ctccagcctg    300
cagcccgagg acttcgccac ctactactgc cagcagtaca gcaccgtgcc ctggaccttc    360
ggccagggca ccaaggtgga aatcaaggga ggtggaggaa gcggtggagg aggtagcgga    420
ggcggcggca gcgaggtgca gctggtggaa tccggcggag actggtgca gcctggcggc    480
tccctgagac tgtcttgcgc cgcctccggc tacgacttca cccactacgg catgaactgg    540
gtccgacagg cccctggcaa gggactgaa tgggtgggct ggatcaacac ctacaccggc    600
gagcccacct acgccgccga cttcaagcgg cggttcacct tcagcctgga caccagcaag    660
agcaccgcct acctgcagat gaactccctg cgggccgagg acaccgccgt gtactactgc    720
gccaagtacc cctactacta cggcaccagc cactggtact cgacgtgtg gggccaggc    780
accctggtca ccgtctcctc a    801
```

<210> SEQ ID NO 20
<211> LENGTH: 267
<212> TYPE: PRT
<213> ORGANISM: Artificial Sequence
<220> FEATURE:
<223> OTHER INFORMATION: 913 molecule amino acid sequence

<400> SEQUENCE: 20

Met Asp Met Arg Val Pro Ala Gln Leu Leu Gly Leu Leu Leu Leu Trp
1               5                   10                  15

Leu Pro Gly Thr Arg Cys Asp Ile Gln Leu Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

| | | | | | | | | | | | | |
|---|---|---|---|---|---|---|---|---|---|---|---|---|
|Ala|Pro|Lys|Val|Leu|Ile|Tyr|Phe|Thr|Ser|Ser|Leu|His|Ser|Gly|Val|
|65| | | |70| | | |75| | | |80| | | |

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
                100                 105                 110

Tyr Ser Thr Val Pro Trp Thr Phe Gly Gln Gly Thr Lys Val Glu Ile
            115                 120                 125

Lys Gly Gly Gly Ser Gly Gly Gly Ser Gly Gly Gly Gly Ser
130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Tyr Asp Phe Thr His Tyr
            165                 170                 175

Gly Met Asn Trp Val Arg Gln Ala Pro Gly Lys Gly Leu Glu Trp Val
            180                 185                 190

Gly Trp Ile Asn Thr Tyr Thr Gly Glu Pro Thr Tyr Ala Ala Asp Phe
            195                 200                 205

Lys Arg Arg Phe Thr Phe Ser Leu Asp Thr Ser Lys Ser Thr Ala Tyr
210                 215                 220

Leu Gln Met Asn Ser Leu Arg Ala Glu Asp Thr Ala Val Tyr Tyr Cys
225                 230                 235                 240

Ala Lys Tyr Pro Tyr Tyr Gly Thr Ser His Trp Tyr Phe Asp Val
            245                 250                 255

Trp Gly Gln Gly Thr Leu Val Thr Val Ser Ser
            260                 265

```
<210> SEQ ID NO 21
<211> LENGTH: 1377
<212> TYPE: DNA
<213> ORGANISM: Artificial Sequence
<220> FEATURE:
<223> OTHER INFORMATION: 917 molecule nucleic acid sequence

<400> SEQUENCE: 21
atggtcagct actgggacac cggggtcctg ctgtgcgcgc tgctcagctg tctgcttctc      60
acaggatcta gttcaggttc gcgaagtgat acaggtagac ctttcgtaga gatgtacagt     120 gaaatcccg aaattataca catgactgaa ggaagggagc tcgtcattcc ctgccggggtt     180 acgtcaccta acatcactgt tactttaaaa agtttccac ttgacacttt gatccctgat      240
ggaaaacgca taatctggga cagtagaaag ggcttcatca tatcaaatgc aacgtacaaa     300
gaaatagggc ttctgacctg tgaagcaaca gtcaatgggc atttgtataa gacaaactat     360
ctcacacatc gacaaaccaa tacaatcatc gatgtggttc tgagtccgtc tcatggaatt     420
gaactatctg ttggagaaaa gcttgtctta aattgtacag caagaactga actaaatgtg     480
gggattgact tcaactggga ataccttcct tcgaagcatc agcataagaa acttgtaaac     540
cgagacctaa aaccccagtc tgggagtgag atgaagaaat ttttgagcac cttaactata     600
gatggtgtaa cccggagtga ccaaggattg tacacctgtg cagcatccag tgggctgatg     660
accaagaaga cagcacatt tgtcagggtc catgaaaaag acaaaactca cacatgccca     720
ccgtgcccag cacctgaact cctgggggga ccgtcagtct tcctcttccc cccaaaaccc     780
aaggacaccc tcatgatctc ccggacccct gaggtcacat gcgtggtggt ggacgtgagc     840
cacgaagacc ctgaggtcaa gttcaactgg tacgtggacg gcgtggaggt gcataatgcc     900
```

-continued

```
aagacaaagc cgcgggagga gcagtacaac agcacgtacc gtgtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gcagccccg  agaaccacag   1080 gtgtacaccc tgcccccatc ccgggatgag ctgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggt     1377
```

<210> SEQ ID NO 22
<211> LENGTH: 459
<212> TYPE: PRT
<213> ORGANISM: Artificial Sequence
<220> FEATURE:
<223> OTHER INFORMATION: 917 molecule amino acid sequence

<400> SEQUENCE: 22

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Arg Ser Asp Thr Gly
            20                  25                  30

Arg Pro Phe Val Glu Met Tyr Ser Glu Ile Pro Glu Ile Ile His Met
        35                  40                  45

Thr Glu Gly Arg Glu Leu Val Ile Pro Cys Arg Val Thr Ser Pro Asn
    50                  55                  60

Ile Thr Val Thr Leu Lys Lys Phe Pro Leu Asp Thr Leu Ile Pro Asp
65                  70                  75                  80

Gly Lys Arg Ile Ile Trp Asp Ser Arg Lys Gly Phe Ile Ile Ser Asn
                85                  90                  95

Ala Thr Tyr Lys Glu Ile Gly Leu Leu Thr Cys Glu Ala Thr Val Asn
            100                 105                 110

Gly His Leu Tyr Lys Thr Asn Tyr Leu Thr His Arg Gln Thr Asn Thr
        115                 120                 125

Ile Ile Asp Val Val Leu Ser Pro Ser His Gly Ile Glu Leu Ser Val
    130                 135                 140

Gly Glu Lys Leu Val Leu Asn Cys Thr Ala Arg Thr Glu Leu Asn Val
145                 150                 155                 160

Gly Ile Asp Phe Asn Trp Glu Tyr Pro Ser Ser Lys His Gln His Lys
                165                 170                 175

Lys Leu Val Asn Arg Asp Leu Lys Thr Gln Ser Gly Ser Glu Met Lys
            180                 185                 190

Lys Phe Leu Ser Thr Leu Thr Ile Asp Gly Val Thr Arg Ser Asp Gln
        195                 200                 205

Gly Leu Tyr Thr Cys Ala Ala Ser Ser Gly Leu Met Thr Lys Lys Asn
    210                 215                 220

Ser Thr Phe Val Arg Val His Glu Lys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285
```

```
Asn Trp Tyr Val Asp Gly Val Glu Val His Asn Ala Lys Thr Lys Pro
        290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ala Pro Ile Glu Lys Thr Ile Ser Lys Ala
            340                 345                 350
Lys Gly Gln Pro Arg Glu Pro Gln Val Tyr Thr Leu Pro Pro Ser Arg
        355                 360                 365
Asp Glu Leu Thr Lys Asn Gln Val Ser Leu Thr Cys Leu Val Lys Gly
    370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
        435                 440                 445
Tyr Thr Gln Lys Ser Leu Ser Leu Ser Pro Gly
    450                 455
```

```
<210> SEQ ID NO 23
<211> LENGTH: 2265
<212> TYPE: DNA
<213> ORGANISM: Artificial Sequence
<220> FEATURE:
<223> OTHER INFORMATION: 964 molecule nucleic acid sequence

<400> SEQUENCE: 23
atgcggcttc cgggtgcgat gccagctctg gccctcaaag gcgagctgct gttgctgtct      60
ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acgggagata ctacttttgc     300
acccacaatg actcccgtgg actggagacc gatgagcgga acggctcta catctttgtg      360 ccagatccca ccgtgggctt cctccctaat gatgccgagg aactattcat ctttctcacg     420
gaaataactg agatcaccat tccatgccga gtaacagacc cacagctggt ggtgacactg     480
cacgagaaga agggggacgt tgcactgcct gtccccctatg atcaccaacg tggcttttct    540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggtccgcca gggtgagaac atcaccctca tgtgcattgt gatcgggaat     720
gaggtggtca cttcgagtg acataccccc gcaaagaaa gtgggcggct ggtggagccg      780
gtgactgact cctcttgga tatgccttac acatccgct ccatcctgca catccccagt       840
gccgagttag aagactcggg gacctacacc tgcaatgtga cggagagtgt gaatgaccat     900
caggatgaaa aggccatcaa catcaccgtg gttgagagcg gctacgtgcg gctcctggga     960
gaggtgggca cactacaatt tgctgagctg catcggagcc ggacactgca ggtagtgttc    1020
gaggcctacc caccgcccac tgtcctgtgg ttcaaagaca accgcaccct gggcgactcc    1080
```

```
agcgctggcg aaatcgccct gtccacgcgc aacgtgtcgg agacccggta tgtgtcagag    1140
ctgacactgg ttcgcgtgaa ggtggcagag gctggccact acaccatgcg ggccttccat    1200
gaggatgctg aggtccagct ctccttccag ctacagatca atgtccctgt ccgagtgctg    1260
gagctaagtg agagccaccc tgacagtggg aacagacaca tccgctgtcg tggccggggc    1320
atgccccagc cgaacatcat ctggtctgcc tgcagagacc tcaaaaggtg tccacgtgag    1380
ctgccgccca cgctgctggg aacagttcc gaagaggaga ccagctgga gactaacgtg     1440 acgtactggg aggaggagca ggagtttgag gtggtgagca cactgcgtct gcagcacgtg    1500
gatcggccac tgtcggtgcg ctgcacgctg cgcaacgctg tgggccagga cacgcaggag    1560
gtcatcgtgg tgccacactc cttgcccttc aagcccccat gcccatcatg cccagcacct    1620
gagttcctgg gggaccatc agtcttcctg ttccccccaa aacccaagga cactctcatg     1680
atctcccgga cccctgaggt cacgtgcgtg gtggtggacg tgagccagga agaccccgag    1740
gtccagttca actggtacgt ggatggcgtg gaggtgcata atgccaagac aaagccgcgg    1800
gaggagcagt tcaacagcac gtaccgtgtg gtcagcgtcc tcaccgtcct gcaccaggac    1860
tggctgaacg gcaaggagta caagtgcaag gtctccaaca aaggcctccc cgtcctccatc   1920 gagaaaacca tctccaaagc caaagggcag ccccgagagc cacaggtgta caccctgccc    1980
ccatcccagg aggagatgac caagaaccag gtcagcctga cctgcctggt caaaggcttc    2040
taccccagcg acatcgccgt ggagtgggag agcaatgggc agccggagaa caactacaag    2100
accacgcctc ccgtgctgga ctccgacggc tccttcttcc tctacagcag gctaaccgtg    2160
gacaagagca ggtggcagga ggggaatgtc ttctcatgct ccgtgatgca tgaggctctg    2220
cacaaccact acacacagaa gagcctctcc ctgtctctgg gtaaa                     2265
```

<210> SEQ ID NO 24
<211> LENGTH: 755
<212> TYPE: PRT
<213> ORGANISM: Artificial Sequence
<220> FEATURE:
<223> OTHER INFORMATION: 964 molecule amino acid sequence

<400> SEQUENCE: 24

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
```

```
            145                 150                 155                 160
His Glu Lys Lys Gly Asp Val Ala Leu Pro Val Pro Tyr Asp His Gln
                    165                 170                 175

Arg Gly Phe Ser Gly Ile Phe Glu Asp Arg Ser Tyr Ile Cys Lys Thr
                    180                 185                 190

Thr Ile Gly Asp Arg Glu Val Asp Ser Asp Ala Tyr Tyr Val Tyr Arg
                    195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                    245                 250                 255

Leu Val Glu Pro Val Thr Asp Phe Leu Leu Asp Met Pro Tyr His Ile
                    260                 265                 270

Arg Ser Ile Leu His Ile Pro Ser Ala Glu Leu Glu Asp Ser Gly Thr
                    275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                    325                 330                 335

Gln Val Val Phe Glu Ala Tyr Pro Pro Pro Thr Val Leu Trp Phe Lys
                    340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
            370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                    405                 410                 415

Val Arg Val Leu Glu Leu Ser Glu Ser His Pro Asp Ser Gly Glu Gln
                    420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Glu Gln Glu Phe Glu Val Val Ser Thr Leu Arg
                    485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Pro Pro Cys Pro Ser Cys Pro Ala Pro Glu Phe Leu Gly
            530                 535                 540

Gly Pro Ser Val Phe Leu Phe Pro Pro Lys Pro Lys Asp Thr Leu Met
545                 550                 555                 560

Ile Ser Arg Thr Pro Glu Val Thr Cys Val Val Val Asp Val Ser Gln
                    565                 570                 575
```

```
Glu Asp Pro Glu Val Gln Phe Asn Trp Tyr Val Asp Gly Val Glu Val
                580                 585                 590

His Asn Ala Lys Thr Lys Pro Arg Glu Glu Gln Phe Asn Ser Thr Tyr
            595                 600                 605

Arg Val Val Ser Val Leu Thr Val Leu His Gln Asp Trp Leu Asn Gly
        610                 615                 620

Lys Glu Tyr Lys Cys Lys Val Ser Asn Lys Gly Leu Pro Ser Ser Ile
625                 630                 635                 640

Glu Lys Thr Ile Ser Lys Ala Lys Gly Gln Pro Arg Glu Pro Gln Val
                645                 650                 655

Tyr Thr Leu Pro Pro Ser Gln Glu Glu Met Thr Lys Asn Gln Val Ser
            660                 665                 670

Leu Thr Cys Leu Val Lys Gly Phe Tyr Pro Ser Asp Ile Ala Val Glu
        675                 680                 685

Trp Glu Ser Asn Gly Gln Pro Glu Asn Asn Tyr Lys Thr Thr Pro Pro
690                 695                 700

Val Leu Asp Ser Asp Gly Ser Phe Phe Leu Tyr Ser Arg Leu Thr Val
705                 710                 715                 720

Asp Lys Ser Arg Trp Gln Glu Gly Asn Val Phe Ser Cys Ser Val Met
                725                 730                 735

His Glu Ala Leu His Asn His Tyr Thr Gln Lys Ser Leu Ser Leu Ser
            740                 745                 750

Leu Gly Lys
        755

<210> SEQ ID NO 25
<211> LENGTH: 2295
<212> TYPE: DNA
<213> ORGANISM: Artificial Sequence
<220> FEATURE:
<223> OTHER INFORMATION: 963 molecule nucleic acid sequence

<400> SEQUENCE: 25
atgcggcttc cgggtgcgat gccagctctg cccctcaaag gcgagctgct gttgctgtct     60
ctcctgttac ttctggaacc acagatctct cagggcctgg tcgtcacacc cccggggcca    120
gagcttgtcc tcaatgtctc cagcaccttc gttctgacct gctcgggttc agctccggtg    180
gtgtgggaac ggatgtccca ggagcccca caggaaatgg ccaaggccca ggatggcacc    240
ttctccagcg tgctcacact gaccaacctc actgggctag acacgggaga atacttttgc    300
acccacaatg actcccgtgg actggagacc gatgagcgga acggctcta catctttgtg    360 ccagatccca ccgtgggctt cctccctaat gatgccgagg aactattcat ctttctcacg    420
gaaataactg agatcaccat tccatgccga gtaacagacc acagctggt ggtgacactg    480 cacgagaaga aggggacgt tgcactgcct gtccctatg atcaccaacg tggcttttct    540
ggtatctttg aggacagaag ctacatctgc aaaaccacca ttggggacag ggaggtggat    600
tctgatgcct actatgtcta cagactccag gtgtcatcca tcaacgtctc tgtgaacgca    660
gtgcagactg tggtccgcca gggtgagaac atcaccctca tgtgcattgt gatcgggaat    720
gaggtggtca cttcgagtg gacatacccc cgcaaagaaa gtgggcggct ggtggagccg    780
gtgactgact tcctcttgga tatgccttac acatccgct ccatcctgca catccccagt    840
gccgagttag aagactcggg gacctacacc tgcaatgtga cggagagtgt gaatgaccat    900
caggatgaaa aggccatcaa catcaccgtg gttgagagcg gctacgtgcg gctcctggga    960
```

```
gaggtgggca cactacaatt tgctgagctg catcggagcc ggacactgca ggtagtgttc    1020
gaggcctacc caccgcccac tgtcctgtgg ttcaaagaca accgcaccct gggcgactcc    1080
agcgctggcg aaatcgccct gtccacgcgc aacgtgtcgg agacccggta tgtgtcagag    1140
ctgacactgg ttcgcgtgaa ggtggcagag gctggccact acaccatgcg ggccttccat    1200
gaggatgctg aggtccagct ctccttccag ctacagatca atgtccctgt ccgagtgctg    1260
gagctaagtg agagccaccc tgacagtggg aacagacag tccgctgtcg tggccggggc    1320
atgccccagc cgaacatcat ctggtctgcc tgcagagacc tcaaaaggtg tccacgtgag    1380
ctgccgccca cgctgctggg aacagttcc gaagaggaga gccagctgga gactaacgtg    1440
acgtactggg aggaggagca ggagtttgag gtggtgagca cactgcgtct gcagcacgtg    1500
gatcggccac tgtcggtgcg ctgcacgctg cgcaacgctg tgggccagga cacgcaggag    1560
gtcatcgtgg tgccacactc cttgcccttc aaggaccccg agcccaaatc ttgtgacaaa    1620
actcacacat gcccaccgtg cccagcacct gaactcctgg ggggaccgtc agtcttcctc    1680
ttccccccaa aacccaagga caccctcatg atctcccgga cccctgaggt cacatgcgtg    1740
gtggtggacg tgagccacga agaccctgag gtcaagttca actggtacgt ggacggcgtg    1800
gaggtgcata atgccaagac aaagccgcgg gaggagcagt acaacagcac gtaccgtgtg    1860
gtcagcgtcc tcaccgtcct gcaccaggac tggctgaatg gcaaggagta caagtgcaag    1920
gtctccaaca aagccctccc agcccccatc gagaaaacca tctccaaagc caaagggcag    1980
ccccgagaac acaggtgta caccctgccc ccatcccggg atgagctgac caagaaccag    2040
gtcagcctga cctgcctggt caaaggcttc tatcccagcg acatcgccgt ggagtgggag    2100
agcaatgggc agccggagaa caactacaag accacgcctc ccgtgctgga ctccgacggc    2160
tccttcttcc tctacagcaa gctcaccgtg gacaagagca ggtggcagca ggggaacgtc    2220
ttctcatgct ccgtgatgca tgaggctctg cacaaccact acacgcagaa gagcctctcc    2280
ctgtctccgg gtaaa                                                    2295
```

<210> SEQ ID NO 26
<211> LENGTH: 765
<212> TYPE: PRT
<213> ORGANISM: Artificial Sequence
<220> FEATURE:
<223> OTHER INFORMATION: 963 molecule amino acid sequence

<400> SEQUENCE: 26

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125
```

```
Pro Asn Asp Ala Glu Glu Leu Phe Ile Phe Leu Thr Glu Ile Thr Glu
    130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
            260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
    290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Pro Thr Val Leu Trp Phe Lys
            340                 345                 350
Asp Asn Arg Thr Leu Gly Asp Ser Ser Ala Gly Glu Ile Ala Leu Ser
        355                 360                 365
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
            420                 425                 430
Thr Val Arg Cys Arg Gly Arg Gly Met Pro Gln Pro Asn Ile Ile Trp
        435                 440                 445
Ser Ala Cys Arg Asp Leu Lys Arg Cys Pro Arg Glu Leu Pro Pro Thr
    450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
Leu Gln His Val Asp Arg Pro Leu Ser Val Arg Cys Thr Leu Arg Asn
            500                 505                 510
Ala Val Gly Gln Asp Thr Gln Glu Val Ile Val Val Pro His Ser Leu
        515                 520                 525
Pro Phe Lys Asp Pro Glu Pro Lys Ser Cys Asp Lys Thr His Thr Cys
    530                 535                 540
```

| | | | | | | | | | | | | | | | |
|---|---|---|---|---|---|---|---|---|---|---|---|---|---|---|---|
| Pro | Pro | Cys | Pro | Ala | Pro | Glu | Leu | Leu | Gly | Gly | Pro | Ser | Val | Phe | Leu |
| 545 | | | | 550 | | | | | 555 | | | | | 560 | |

Phe Pro Pro Lys Pro Lys Asp Thr Leu Met Ile Ser Arg Thr Pro Glu
          565                 570                 575

Val Thr Cys Val Val Val Asp Val Ser His Glu Asp Pro Glu Val Lys
        580                 585                 590

Phe Asn Trp Tyr Val Asp Gly Val Glu Val His Asn Ala Lys Thr Lys
            595                 600                 605

Pro Arg Glu Glu Gln Tyr Asn Ser Thr Tyr Arg Val Val Ser Val Leu
    610                 615                 620

Thr Val Leu His Gln Asp Trp Leu Asn Gly Lys Glu Tyr Lys Cys Lys
625                 630                 635                 640

Val Ser Asn Lys Ala Leu Pro Ala Pro Ile Glu Lys Thr Ile Ser Lys
                645                 650                 655

Ala Lys Gly Gln Pro Arg Glu Pro Gln Val Tyr Thr Leu Pro Pro Ser
            660                 665                 670

Arg Asp Glu Leu Thr Lys Asn Gln Val Ser Leu Thr Cys Leu Val Lys
        675                 680                 685

Gly Phe Tyr Pro Ser Asp Ile Ala Val Glu Trp Glu Ser Asn Gly Gln
690                 695                 700

Pro Glu Asn Asn Tyr Lys Thr Thr Pro Pro Val Leu Asp Ser Asp Gly
705                 710                 715                 720

Ser Phe Phe Leu Tyr Ser Lys Leu Thr Val Asp Lys Ser Arg Trp Gln
                725                 730                 735

Gln Gly Asn Val Phe Ser Cys Ser Val Met His Glu Ala Leu His Asn
            740                 745                 750

His Tyr Thr Gln Lys Ser Leu Ser Leu Ser Pro Gly Lys
        755                 760                 765

<210> SEQ ID NO 27
<211> LENGTH: 1656
<212> TYPE: DNA
<213> ORGANISM: Artificial Sequence
<220> FEATURE:
<223> OTHER INFORMATION: 974 molecule nucleic acid sequence

<400> SEQUENCE: 27

```
atgcggcttc cgggtgcgat gccagctctg gccctcaaag cgagctgct gttgctgtct      60 ctcctgttac ttctggaacc acagatctct cagggcctgg tcgtcacacc cccggggcca     120
gagcttgtcc tcaatgtctc cagcaccttc gttctgacct gctcgggttc agctccggtg     180
gtgtgggaac ggatgtccca ggagccccca caggaaatgg ccaaggccca ggatggcacc     240
ttctccagcg tgctcacact gaccaacctc actgggctag acacgggaga atacttttgc     300
acccacaatg actcccgtgg actggagacc gatgagcgga acggctcta catctttgtg      360 ccagatccca ccgtgggctt cctccctaat gatgccgagg aactattcat ctttctcacg     420
gaaataactg agatcaccat tccatgccga gtaacagacc acagctggt ggtgacactg      480 cacgagaaga aggggacgt tgcactgcct gtccctatg atcaccaacg tggcttttct      540
ggtatctttg aggacagaag ctacatctgc aaaaccacca ttggggacag ggaggtggat     600
tctgatgcct actatgtcta cagactccag gtgtcatcca tcaacgtctc tgtgaacgca     660
gtgcagactg tggtccgcca gggtgagaac atcaccctca tgtgcattgt gatcgggaat     720
gaggtggtca acttcgagtg gacatacccc cgcaaagaaa gtgggcggct ggtggagccg     780
gtgactgact tcctcttgga tatgccttac acatccgct ccatcctgca catccccagt     840
```

```
gccgagttag aagactcggg gacctacacc tgcaatgtga cggagagtgt gaatgaccat    900
caggatgaaa aggccatcaa catcaccgtg gttgagagcg gctacgtgcg gctcctggga    960
gagcccaaat cttgtgacaa aactcacaca tgcccaccgt gcccagcacc tgaactcctg   1020
gggggaccgt cagtcttcct cttccccccca aaacccaagg acaccctcat gatctcccgg   1080
accccctgagg tcacatgcgt ggtggtggac gtgagccacg aagaccctga ggtcaagttc   1140
aactggtacg tggacggcgt ggaggtgcat aatgccaaga caaagccgcg ggaggagcag   1200
tacaacagca cgtaccgtgt ggtcagcgtc ctcaccgtcc tgcaccagga ctggctgaat   1260
ggcaaggagt acaagtgcaa ggtctccaac aaagccctcc cagcccccat cgagaaaacc   1320
atctccaaag ccaaagggca gccccgagaa ccacaggtgt acaccctgcc cccatcccgg   1380
gatgagctga ccaagaacca ggtcagcctg acctgcctgg tcaaaggctt ctatcccagc   1440
gacatcgccg tggagtggga gagcaatggg cagccggaga caactacaa gaccacgcct   1500
cccgtgctgg actccgacgg ctccttcttc ctctacagca agctcaccgt ggacaagagc   1560
aggtggcagc aggggaacgt cttctcatgc tccgtgatgc atgaggctct gcacaaccac   1620
tacacgcaga agagcctctc cctgtctccg ggtaaa                             1656
```

<210> SEQ ID NO 28
<211> LENGTH: 552
<212> TYPE: PRT
<213> ORGANISM: Artificial Sequence
<220> FEATURE:
<223> OTHER INFORMATION: 974 molecule amino acid sequence

<400> SEQUENCE: 28

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
```

| | 210 | | | 215 | | | 220 | | |
|---|---|---|---|---|---|---|---|---|---|
Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
            245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Pro Lys Ser Cys Asp Lys Thr His Thr Cys Pro Pro Cys Pro Ala
                325                 330                 335

Pro Glu Leu Leu Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
        355                 360                 365

Val Asp Val Ser His Glu Asp Pro Glu Val Lys Phe Asn Trp Tyr Val
370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
        435                 440                 445

Arg Glu Pro Gln Val Tyr Thr Leu Pro Pro Ser Arg Asp Glu Leu Thr
    450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
        515                 520                 525

Ser Cys Ser Val Met His Glu Ala Leu His Asn His Tyr Thr Gln Lys
    530                 535                 540

Ser Leu Ser Leu Ser Pro Gly Lys
545                 550

<210> SEQ ID NO 29
<211> LENGTH: 1593
<212> TYPE: DNA
<213> ORGANISM: Artificial Sequence
<220> FEATURE:
<223> OTHER INFORMATION: 978 molecule nucleic acid sequence

<400> SEQUENCE: 29
atgcggcttc cgggtgcgat gccagctctg gccctcaaag gcgagctgct gttgctgtct     60
ctcctgttac ttctggaacc acagatctct cagggcctgg tcgtcacacc cccggggcca    120

```
gagcttgtcc tcaatgtctc cagcaccttc gttctgacct gctcgggttc agctccggtg      180
gtgtgggaac ggatgtccca ggagccccca caggaaatgg ccaaggccca ggatggcacc      240
ttctccagcg tgctcacact gaccaacctc actgggctag acacgggaga atacttttgc      300
acccacaatg actcccgtgg actggagacc gatgagcgga acggctcta catctttgtg       360 ccagatccca ccgtgggctt cctccctaat gatgccgagg aactattcat ctttctcacg      420
gaaataactg agatcaccat tccatgccga gtaacagacc cacagctggt ggtgacactg      480
cacgagaaga aggggacgt tgcactgcct gtcccctatg atcaccaacg tggcttttct       540
ggtatctttg aggacagaag ctacatctgc aaaaccacca ttggggacag ggaggtggat      600
tctgatgcct actatgtcta cagactccag gtgtcatcca tcaacgtctc tgtgaacgca      660
gtgcagactg tggtccgcca gggtgagaac atcaccctca tgtgcattgt gatcgggaat      720
gaggtggtca acttcgagtg gacataccc cgcaaagaaa gtgggcggct ggtggagccg       780
gtgactgact tcctcttgga tatgccttac cacatccgct ccatcctgca catccccagt      840
gccgagttag aagactcggg gacctacacc tgcaatgtga cggagagtgt gaatgaccat      900
caggatgaaa aggccatcaa catcaccgtg gttgagagcg gctacgtgcg gctcctggga      960
gaggtgggca cactacaatt tgctgagctg catcggagcc ggacactgca ggtagtgttc      1020
gaggcctacc accgcccac tgtcctgtgg ttcaaagaca accgcaccct gggcgactcc      1080
agcgctggcg aaatcgccct gtccacgcgc aacgtgtcgg agaccggta tgtgtcagag      1140 ctgacactgg ttcgcgtgaa ggtggcagag ctggccact acaccatgcg ggccttccat       1200
gaggatgctg aggtccagct ctccttccag ctacagatca atgtccctgt ccagtgctg      1260 gagctaagtg agagccaccc tgacagtggg aacagacag tccgctgtcg tggccggggc       1320
atgccccagc cgaacatcat ctggtctgcc tgcagagacc tcaaaaggtg tccacgtgag     1380
ctgccgccca cgctgctggg aacagttcc gaagaggaga gccagctgga gactaacgtg      1440
acgtactggg aggaggagca ggagtttgag gtggtgagca cactgcgtct gcagcacgtg      1500
gatcggccac tgtcggtgcg ctgcacgctg cgcaacgctg tgggccagga cacgcaggag      1560
gtcatcgtgg tgccacactc cttgcccttc aag                                    1593
```

<210> SEQ ID NO 30
<211> LENGTH: 531
<212> TYPE: PRT
<213> ORGANISM: Artificial Sequence
<220> FEATURE:
<223> OTHER INFORMATION: 978 molecule amino acid sequence

<400> SEQUENCE: 30

```
Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
```

```
                100                 105                 110
Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
        180                 185                 190

Thr Ile Gly Asp Arg Glu Val Asp Ser Asp Ala Tyr Val Tyr Arg
        195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
        290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
        370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
        500                 505                 510

Ala Val Gly Gln Asp Thr Gln Glu Val Ile Val Val Pro His Ser Leu
        515                 520                 525
```

Pro Phe Lys
    530

<210> SEQ ID NO 31
<211> LENGTH: 1737
<212> TYPE: DNA
<213> ORGANISM: Artificial Sequence
<220> FEATURE:
<223> OTHER INFORMATION: 977 molecule nucleic acid sequence

<400> SEQUENCE: 31

| | | | | | |
|---|---|---|---|---|---|
| atggggcagt | gcaggaaaag | tggcactatg | aaccctgcag | ccctagacaa | ttgtactaac | 60 |
| cttcttctct | ttcctctcct | gacaggttgg | tgtacagtag | cttccaagta | ctccaccatg | 120 |
| cggcttccgg | gtgcgatgcc | agctctggcc | ctcaaaggcg | agctgctgtt | gctgtctctc | 180 |
| ctgttacttc | tggaaccaca | gatctctcag | ggcctggtcg | tcacaccccc | ggggccagag | 240 |
| cttgtcctca | atgtctccag | cacctttcgtt | ctgacctgct | cgggttcagc | tccggtggtg | 300 |
| tgggaacgga | tgtcccagga | gcccccacag | gaaatggcca | aggcccagga | tggcaccttc | 360 |
| tccagcgtgc | tcacactgac | caacctcact | gggctagaca | cgggagaata | cttttgcacc | 420 |
| cacaatgact | cccgtggact | ggagaccgat | gagcggaaac | ggctctacat | ctttgtgcca | 480 |
| gatcccaccg | tgggcttcct | ccctaatgat | gccgaggaac | tattcatctt | tctcacggaa | 540 |
| ataactgaga | tcaccattcc | atgccgagta | acagacccac | agctggtggt | gacactgcac | 600 |
| gagaagaaag | ggacgttgc | actgcctgtc | ccctatgatc | accaacgtgg | cttttctggt | 660 |
| atctttgagg | acagaagcta | catctgcaaa | accaccattg | gggacaggga | ggtggattct | 720 |
| gatgcctact | atgtctacag | actccaggtg | tcatccatca | acgtctctgt | gaacgcagtg | 780 |
| cagactgtgg | tccgccaggg | tgagaacatc | accctcatgt | gcattgtgat | cgggaatgag | 840 |
| gtggtcaact | tcgagtggac | ataccccgc | aaagaaagtg | ggcggctggt | ggagccggtg | 900 |
| actgacttcc | tcttggatat | gccttaccac | atccgctcca | tcctgcacat | ccccagtgcc | 960 |
| gagttagaag | actcggggac | ctacacctgc | aatgtgacgg | agagtgtgaa | tgaccatcag | 1020 |
| gatgaaaagg | ccatcaacat | caccgtggtt | gagagcggct | acgtgcggct | cctgggagag | 1080 |
| gtgggcacac | tacaatttgc | tgagctgcat | cggagccgga | cactgcaggt | agtgttcgag | 1140 |
| gcctacccac | cgcccactgt | cctgtggttc | aaagacaacc | gcaccctggg | cgactccagc | 1200 |
| gctggcgaaa | tcgccctgtc | cacgcgcaac | gtgtcggaga | cccggtatgt | gtcagagctg | 1260 |
| acactggttc | gcgtgaaggt | ggcagaggct | ggccactaca | ccatgcgggc | cttccatgag | 1320 |
| gatgctgagg | tccagctctc | cttccagcta | cagatcaatg | tccctgtccg | agtgctggag | 1380 |
| ctaagtgaga | gccaccctga | cagtgggaa | cagacagtcc | gctgtcgtgg | ccggggcatg | 1440 |
| ccccagccga | acatcatctg | gtctgcctgc | agagacctca | aaaggtgtcc | acgtgagctg | 1500 |
| ccgcccacgc | tgctggggaa | cagttccgaa | gaggagagcc | agctggagac | taacgtgacg | 1560 |
| tactgggagg | aggagcagga | gttgagggtg | gtgagcacac | tgcgtctgca | gcacgtggat | 1620 |
| cggccactgt | cggtgcgctg | cacgctgcgc | aacgctgtgg | gccaggacac | gcaggaggtc | 1680 |
| atcgtggtgc | cacactcttt | gcccttcaag | cggggcagcc | accaccacca | ccaccac | 1737 |

<210> SEQ ID NO 32
<211> LENGTH: 579
<212> TYPE: PRT
<213> ORGANISM: Artificial Sequence
<220> FEATURE:
<223> OTHER INFORMATION: 977 molecule amino acid sequence

```
<400> SEQUENCE: 32

Met Gly Gln Cys Arg Lys Ser Gly Thr Met Asn Pro Ala Ala Leu Asp
1               5                   10                  15

Asn Cys Thr Asn Leu Leu Leu Phe Pro Leu Leu Thr Gly Trp Cys Thr
            20                  25                  30

Val Ala Ser Lys Tyr Ser Thr Met Arg Leu Pro Gly Ala Met Pro Ala
        35                  40                  45

Leu Ala Leu Lys Gly Glu Leu Leu Leu Ser Leu Leu Leu Leu
    50                  55                  60

Glu Pro Gln Ile Ser Gln Gly Leu Val Val Thr Pro Gly Pro Glu
65              70                  75                  80

Leu Val Leu Asn Val Ser Ser Thr Phe Val Leu Thr Cys Ser Gly Ser
                85                  90                  95

Ala Pro Val Val Trp Glu Arg Met Ser Gln Glu Pro Pro Gln Glu Met
                100                 105                 110

Ala Lys Ala Gln Asp Gly Thr Phe Ser Ser Val Leu Thr Leu Thr Asn
            115                 120                 125

Leu Thr Gly Leu Asp Thr Gly Glu Tyr Phe Cys Thr His Asn Asp Ser
    130                 135                 140

Arg Gly Leu Glu Thr Asp Glu Arg Lys Arg Leu Tyr Ile Phe Val Pro
145                 150                 155                 160

Asp Pro Thr Val Gly Phe Leu Pro Asn Asp Ala Glu Glu Leu Phe Ile
                165                 170                 175

Phe Leu Thr Glu Ile Thr Glu Ile Thr Ile Pro Cys Arg Val Thr Asp
                180                 185                 190

Pro Gln Leu Val Val Thr Leu His Glu Lys Lys Gly Asp Val Ala Leu
            195                 200                 205

Pro Val Pro Tyr Asp His Gln Arg Gly Phe Ser Gly Ile Phe Glu Asp
    210                 215                 220

Arg Ser Tyr Ile Cys Lys Thr Thr Ile Gly Asp Arg Glu Val Asp Ser
225                 230                 235                 240

Asp Ala Tyr Tyr Val Tyr Arg Leu Gln Val Ser Ser Ile Asn Val Ser
                245                 250                 255

Val Asn Ala Val Gln Thr Val Val Arg Gln Gly Glu Asn Ile Thr Leu
            260                 265                 270

Met Cys Ile Val Ile Gly Asn Glu Val Val Asn Phe Glu Trp Thr Tyr
    275                 280                 285

Pro Arg Lys Glu Ser Gly Arg Leu Val Glu Pro Val Thr Asp Phe Leu
    290                 295                 300

Leu Asp Met Pro Tyr His Ile Arg Ser Ile Leu His Ile Pro Ser Ala
305                 310                 315                 320

Glu Leu Glu Asp Ser Gly Thr Tyr Thr Cys Asn Val Thr Glu Ser Val
                325                 330                 335

Asn Asp His Gln Asp Glu Lys Ala Ile Asn Ile Thr Val Val Glu Ser
            340                 345                 350

Gly Tyr Val Arg Leu Leu Gly Glu Val Gly Thr Leu Gln Phe Ala Glu
    355                 360                 365

Leu His Arg Ser Arg Thr Leu Gln Val Val Phe Glu Ala Tyr Pro Pro
    370                 375                 380

Pro Thr Val Leu Trp Phe Lys Asp Asn Arg Thr Leu Gly Asp Ser Ser
385                 390                 395                 400

Ala Gly Glu Ile Ala Leu Ser Thr Arg Asn Val Ser Glu Thr Arg Tyr
```

-continued

```
                        405                 410                 415
Val Ser Glu Leu Thr Leu Val Arg Val Lys Val Ala Glu Ala Gly His
            420                 425                 430

Tyr Thr Met Arg Ala Phe His Glu Asp Ala Glu Val Gln Leu Ser Phe
        435                 440                 445

Gln Leu Gln Ile Asn Val Pro Val Arg Val Leu Glu Leu Ser Glu Ser
    450                 455                 460

His Pro Asp Ser Gly Glu Gln Thr Val Arg Cys Arg Gly Arg Gly Met
465                 470                 475                 480

Pro Gln Pro Asn Ile Ile Trp Ser Ala Cys Arg Asp Leu Lys Arg Cys
                485                 490                 495

Pro Arg Glu Leu Pro Pro Thr Leu Leu Gly Asn Ser Ser Glu Glu Glu
            500                 505                 510

Ser Gln Leu Glu Thr Asn Val Thr Tyr Trp Glu Glu Glu Gln Glu Phe
            515                 520                 525

Glu Val Val Ser Thr Leu Arg Leu Gln His Val Asp Arg Pro Leu Ser
    530                 535                 540

Val Arg Cys Thr Leu Arg Asn Ala Val Gly Gln Asp Thr Gln Glu Val
545                 550                 555                 560

Ile Val Val Pro His Ser Leu Pro Phe Lys Arg Gly Ser His His His
                565                 570                 575

His His His
```